United States Patent
Maeda et al.

(10) Patent No.: US 9,937,152 B2
(45) Date of Patent: Apr. 10, 2018

(54) DERIVATIVE OF STYRENE-MALEIC ACID COPOLYMER

(71) Applicant: Hiroshi Maeda, Kumamoto (JP)

(72) Inventors: Hiroshi Maeda, Kumamoto (JP); Hideaki Nakamura, Kumamoto (JP); Jun Fang, Kumamoto (JP)

(73) Assignee: Hiroshi Maeda, Kumamoto (JP)

( * ) Notice: Subject to any disclaimer, the term of this patent is extended or adjusted under 35 U.S.C. 154(b) by 0 days.

(21) Appl. No.: 15/037,723

(22) PCT Filed: Nov. 19, 2014

(86) PCT No.: PCT/JP2014/080688
§ 371 (c)(1),
(2) Date: Jul. 1, 2016

(87) PCT Pub. No.: WO2015/076312
PCT Pub. Date: May 28, 2015

(65) Prior Publication Data
US 2016/0317672 A1 Nov. 3, 2016

(30) Foreign Application Priority Data
Nov. 19, 2013 (JP) ................. 2013-239222

(51) Int. Cl.
C08F 222/06 (2006.01)
C08F 8/44 (2006.01)
(Continued)

(52) U.S. Cl.
CPC ............ *A61K 31/409* (2013.01); *A61K 31/69* (2013.01); *A61K 31/704* (2013.01); *A61K 47/58* (2017.08);
(Continued)

(58) Field of Classification Search
None
See application file for complete search history.

(56) References Cited

U.S. PATENT DOCUMENTS 3,368,987 A 2/1968 Pollart et al.
3,472,820 A 10/1969 Kalopissis et al.
(Continued)

FOREIGN PATENT DOCUMENTS

CA 1 241 640 9/1988
EP 0 136 791 4/1985
(Continued)

OTHER PUBLICATIONS

Elvira et al., "Covalent Polymer-Drug Conjugates", Molecules 2005, 10(1), pp. 114-125.*
(Continued)

*Primary Examiner* — Ernst V Arnold
*Assistant Examiner* — Kyung S Chang
(74) *Attorney, Agent, or Firm* — Wenderoth, Lind & Ponack, L.L.P.

(57) ABSTRACT

The present invention provides a group of novel SMA derivatives and a covalent conjugate of the derivatives and an active substance. More specifically, the present invention provides: an SMA derivative which contains (i) a styrene-maleic acid copolymer (SMA) and (ii) a side chain (b) that contains a functional group (a) selected from among —NH2, —SH, —OH, —COOH, —NH—(C=NH)—NH$_2$ and —C(CH$_2$—OH)$_3$ and introduced into a carboxyl group of a maleic acid residue of the SMA via an amide bond or an ester bond, and wherein when a plurality of side chain (b) is introduced into the SMA, the side chains (b) may be identical or different from each other; and a conjugate of this SMA derivative and an active substance.

8 Claims, 12 Drawing Sheets

(51) Int. Cl.
| | |
|---|---|
| C08F 8/42 | (2006.01) |
| C08F 8/34 | (2006.01) |
| C08F 8/12 | (2006.01) |
| C08F 8/32 | (2006.01) |
| C08F 8/30 | (2006.01) |
| A61K 38/00 | (2006.01) |
| C07K 14/575 | (2006.01) |
| A61K 31/409 | (2006.01) |
| A61K 31/69 | (2006.01) |
| A61K 31/704 | (2006.01) |
| C08F 220/04 | (2006.01) |
| A61K 47/58 | (2017.01) |

(52) U.S. Cl.
CPC ............... *C08F 8/12* (2013.01); *C08F 8/30* (2013.01); *C08F 8/32* (2013.01); *C08F 8/34* (2013.01); *C08F 8/42* (2013.01); *C08F 8/44* (2013.01); *C08F 220/04* (2013.01); *C08F 222/06* (2013.01); *A61K 38/00* (2013.01); *C07K 14/575* (2013.01); *C08F 2800/10* (2013.01)

(56) References Cited

U.S. PATENT DOCUMENTS

| | | |
|---|---|---|
| 3,679,640 A | 7/1972 | Moore et al. |
| 4,182,752 A | 1/1980 | Maeda et al. |
| 4,732,933 A | 3/1988 | Maeda et al. |
| 4,762,885 A | 8/1988 | Maeda et al. |
| 4,782,113 A | 11/1988 | Maeda et al. |
| 8,128,959 B2 | 3/2012 | Maeda et al. |
| 2005/0032929 A1 | 2/2005 | Greener |
| 2005/0201974 A1 | 9/2005 | Schestopol et al. |
| 2008/0299557 A1 | 12/2008 | Himmelreich et al. |
| 2010/0184955 A1* | 7/2010 | Kim ............... A61K 47/48176 530/362 |
| 2014/0294735 A1* | 10/2014 | Maeda ............... A61B 1/043 424/9.61 |

FOREIGN PATENT DOCUMENTS

| | | | |
|---|---|---|---|
| JP | 43-6233 | 3/1968 | |
| JP | 47-611 | 1/1972 | |
| JP | 53-117095 | 10/1978 | |
| JP | 4-279527 | 10/1992 | |
| JP | 2005-503474 | 2/2005 | |
| JP | 2007-517776 | 7/2007 | |
| JP | 4522452 | 8/2010 | |
| WO | WO 2013/035750 A1 * | 3/2013 | ............. A61B 1/043 |

OTHER PUBLICATIONS

International Search Report dated Feb. 24, 2015 in International Application No. PCT/JP2014/080688.
International Preliminary Report on Patentability dated May 24, 2016 in International Application No. PCT/JP2014/080688.
H. Maeda, J. Takeshita and R. Kanamaru: "A Lipophilic Derivative of Neocarzinostatin" A polymer conjugation of an antitumor protein antibiotic, Int. J. Peptide Protein Res., 14, pp. 81-87 (1979).
H. Maeda: "SMANCS and polymer-conjugated macromolecular drugs: advantages in cancer chemotherapy", Adv. Drug Delivery Reviews, 46, pp. 169-185 (2001).
K. Greish. H. Maeda, Drug Delivery System vol. 18, No. 3, pp. 254 (2003).
M. Regehly, K. Greish, F. Rancan, H. Maeda, F. Böhm and B. Röder: "Water-Soluble Polymer Conjugates of ZnPP for Photodynamic Tumor Therapy", Bioconj. Chem., 18, pp. 494-499 (2007).
K. Greish, T. Sawa, J. Fang, T. Akaike and H. Maeda: "SMA—doxorubicin, a new polymeric micellar drug for effective targeting to solid tumours", J. Cont. Release, 97, pp. 219-230 (2004).
K. Greish, A. Nagamitsu, J. Fang and H. Maeda: "Copoly (styrene-maleic-acid)-Pirarubicin Micelles: High Tumor Targeting Efficiency with Little Toxicity", Bioconj. Chem., 16, pp. 230-236 (2005).
A. K. Iyer, K. Greish, J. Fang, R. Murakami and H. Maeda: "High-loading nanosized micelles of copoly (styrene-maleic acid)-zinc protoporphyrin for targeted delivery of a potent heme oxygenase inhibitor", Biomaterials, 28, pp. 1871-1881(2007).
A. K. Iyer, K. Greish, T. Seki, S. Okazaki, J. Fang, K. Takeshita and H. Maeda: "Polymeric micelles of zinc protoporphyrin for tumjor targeted delivery based on EPR effect and sinlet oxyen genereation", J Drug Targeting, 15, pp. 496-506 (2007).
H. Maeda, H. Nakamura, J. Fang: "The EPR effect for macromolecular drug delivery to solid tumors: Improvement of tumor uptake, lowering of systemic toxicity, and distinct tumor imaging in vivo", Adv. Drug Deliver. Rev. 65, pp. 71-79 (2013).
Y. Matsumura and H. Maeda: "A New Concept for Macromolecular Therapeutics in Cancer Chemotherapy: Mechanism of Tumoritropic Accumulation of Proteins and the Antitumor Agent SMANCS", Cancer Res., 46, pp. 6387-6392 (1986).
H. Maeda: "Macromolecular therapeutics in cancer treatment: the EPR effect and beyond", J. Control. Release, 164, pp. 138-144 (2012).
H. Maeda, T. Sawa, and T. Konno: "Mechanism of tumor-targeted delivery of macromolecular drugs, including the EPR effect in solid tumor and clinical overview of the prototype polymeric drug SMANCS", J. Cont. Release, 74, pp. 47-61 (2001).
H. Maeda, J. Takeshita, R. Kanamaru, H. Sato, J. Khatoh and H. Sato: "Antimetastatic and Antitumor Activity of a Derivative of Neocarzinostatin: An Organic Solvent- and Water-Soluble Polymer-Conjugated Protein", Gann, 70, pp. 601-606 (1979).
T. Oda, T. Morinaga and H. Maeda: "Stimulation of Macrophage by Polyanions and Its Conjugated Proteins and Effect on Cell Membrane", Proc. Soc. Exp. Biol. Med., 181, pp. 9-17 (1986).
J. Fang, K. Greish, H. Qin, H. Nakamura, M. Takeya, and H. Maeda: "HSP32 (HO-1) inhibitor, copoly(styrene-maleic acid)-zinc protoporphyrin IX, a water-soluble micelle as anticancer agent: In vitro and in vivo anticancer effect", Eur. J. Pharm. Biopharma. 81, pp. 540-547 (2012).
H. Herrmann, M. Kneidinger, S. Cerny-Reiterer, T. Rülicke, M. Willmann,K.V. Gleixner, K. Blatt, G. Hörmann, B. Peter, P. Samorapoompichit, W. Pickl, G. Y. Bharate, M. Mayerhofer, W. R. Sperr, H. Maeda, P. Valent: "The Hsp32 Inhibitors SMA-ZnPP and PEG-ZnPP Exert Major Growth-Inhibitory Effects on $CD34^+$/$CD38^+$ and $CD34^+$/$CD38^-$ AML Progenitor Cells", Current Cancer Drug Targets.12(1), pp. 51-63 (2012).
S. Yamamoto, Y. Kaneo, H. Maeda: "Styrene maleic acid anhydride copolymer (SMA) for the encapsulation of sparingly water-soluble drugs in nanoparticles", J. Drug Del. Sci. Tech., 23, pp. 231-237 (2013).
H. Yin, J. Fang, L. Liao, H. Nakamura, and H. Maeda: "Styrene-maleic acid copolymer-encapsulated CORM2, a water-soluble carbon monoxide (CO) donor with a constant CO-releasing property, exhibits therapeutic potential for inflammatory bowel disease", J. Control. Release 187, pp. 14-21 (2014).
K. Tsukigawa, L. Liao, H. Nakamura, J. Fang, K. Greish, M. Otagiri, H. Maeda: "Synthesis and therapeutic effect of styrene-maleic acid copolymer conjugated pirarubicin", Cancer Sci. 106, pp. 270-278 (2015).
J. Daruwalla, K. Greish, C. Malcontenti-Wilson, V. Muralidharan, H. Maeda, C. Christophi: "Styrene maleic acid copolymer-pirarubicin induces tumor-selective oxidative stress and decreases tumor hypoxia as possible treatment of colorectal cancer liver metastases", Surgery 158, pp. 236-247 (2015).
A. Saisyo, H. Nakamura, J. Fang, K. Greish, H. Furukawa, H. Maeda: "pH-sensitive polymeric cisplatin-ion complex with styrene-maleic acid copolymer exhibits tumor-selective drug delivery and antitumor activity as a result of the enhanced permeability and retention effect", Colloids and Surfaces B: Biointerfaces 138, pp. 128-137 (2016).
N. N. Parayath, H. Nehoff, P. Müller, S. Taurin, K. Greish: "Styrene maleic acid micelles as a nanocarrier system for oral anticancer drug delivery—dual uptake through enterocytes and M-cells", Int J Nanomedicine, 10, pp. 4653-4667 (2015).

(56) References Cited

OTHER PUBLICATIONS

Partial Supplementary European Search Report dated Jul. 21, 2017 issued in corresponding European Patent Application No. 14864695.3.

Examination report dated Aug. 7, 2017 issued in corresponding Australian Patent Application No. 2014354087.

* cited by examiner

[Figure 1]
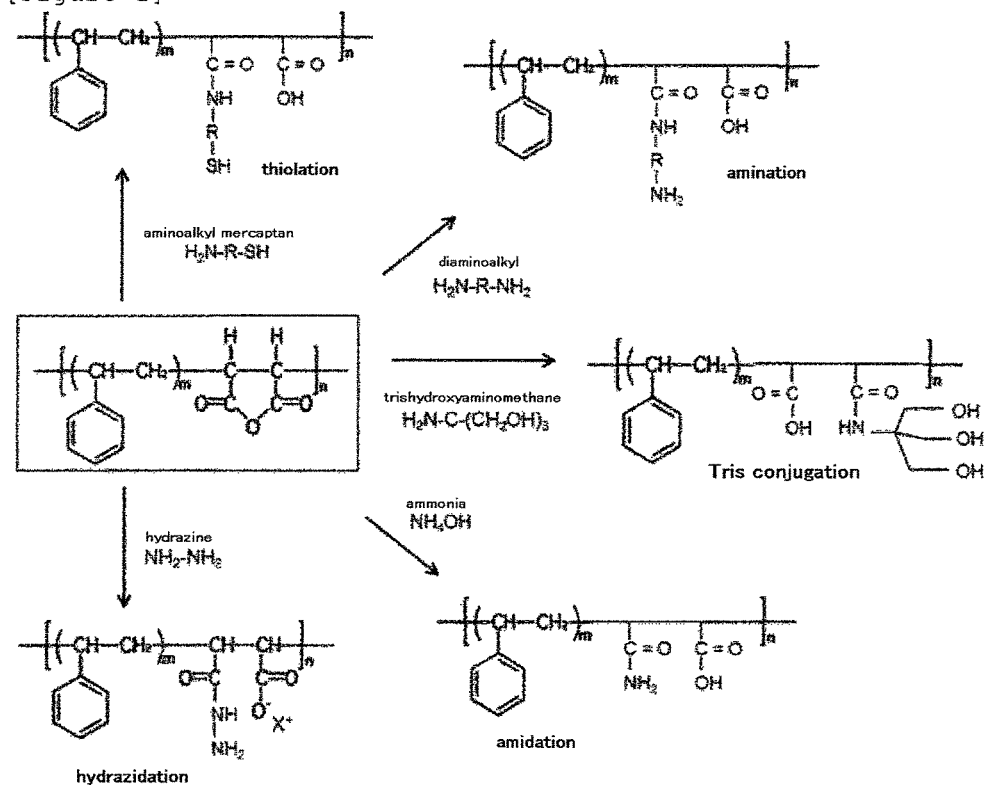
[Figure 2]
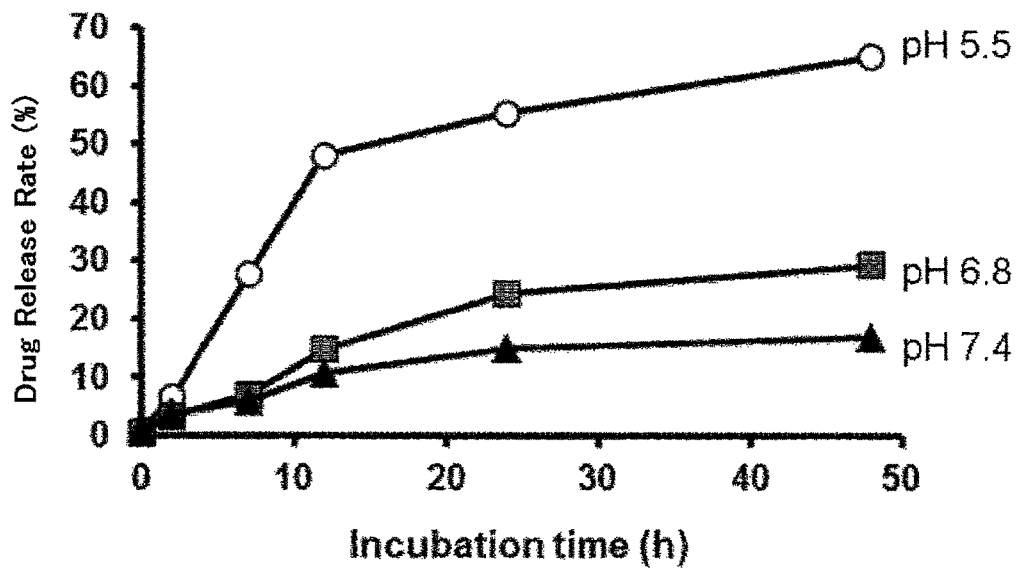

Raman Absorption Spectra

[Figure 5]
In vivo antitumor activity of SMA-THP in mice
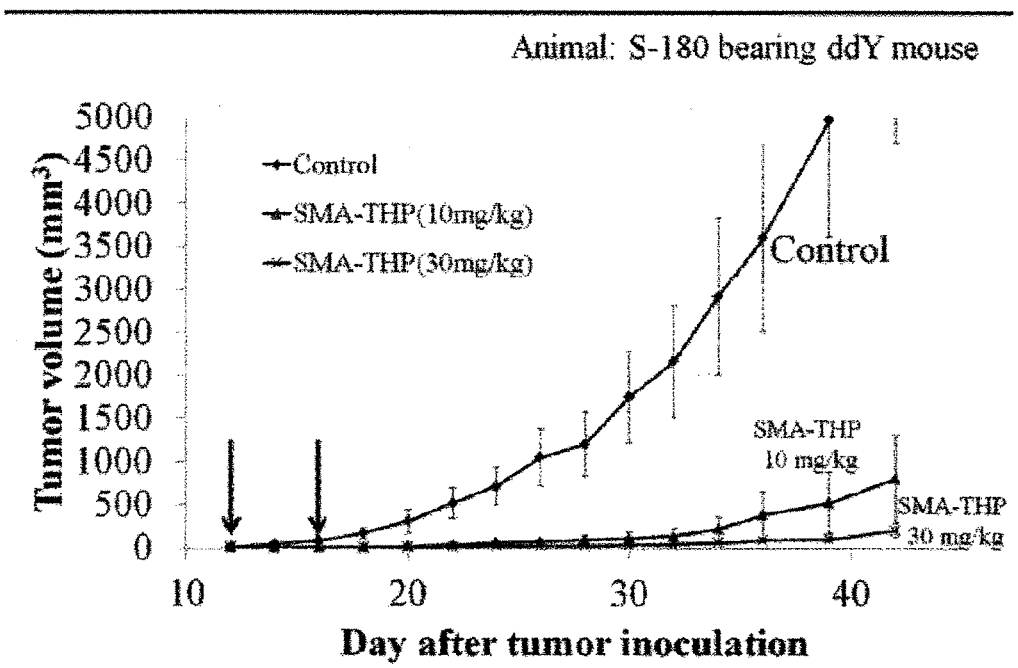

[Figure 6]
Survival rate after the starting the treatment of mouse S-180
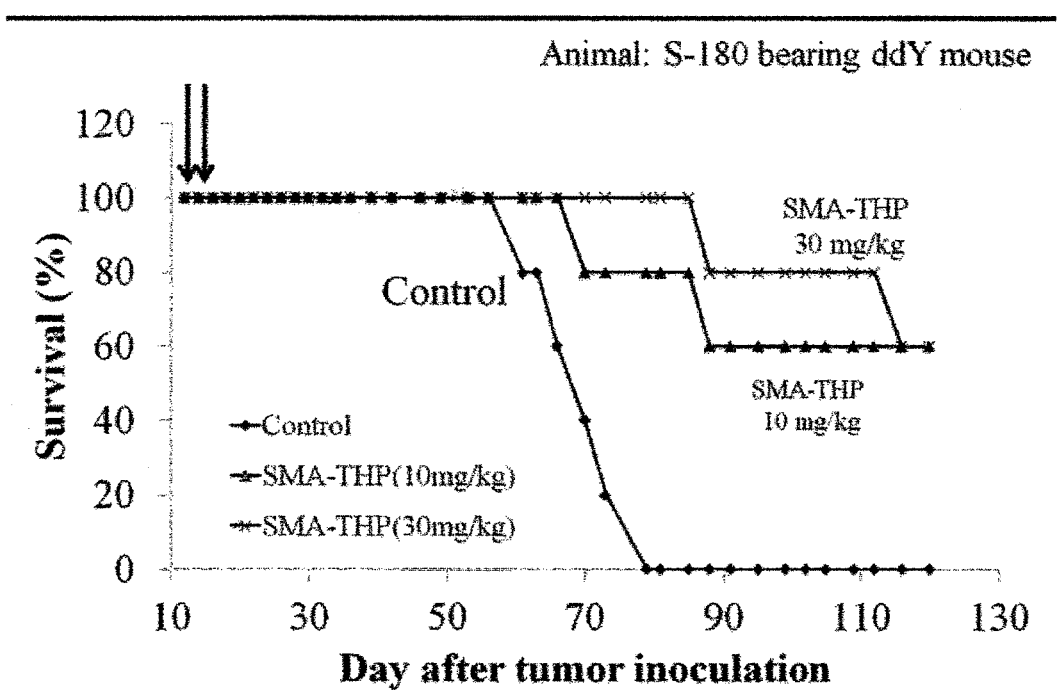

DERIVATIVE OF STYRENE-MALEIC ACID COPOLYMER

TECHNICAL FIELD

The present patent application claims the priority of Japanese Patent Application No. 2013-239222, the entire contents of which are incorporated by reference herein.

The present invention relates to a styrene-maleic acid copolymer derivative, a conjugate of said derivative and an active substance and a method for preparing the same.

BACKGROUND ART

The present inventors (Maeda et al.) have found that styrene-maleic acid (or maleic anhydride) copolymers (hereinafter, referred to as "SMA") may be an excellent carrier for pharmaceuticals due to the remarkable amphiphilicity. Accordingly, the present inventors developed SMANCS, a useful macromolecular-conjugated carcinostatic agent (that was approved by the Japanese Ministry of Health, Labour and Welfare in 1993; see U.S. Pat. No. 4,182,752; U.S. Pat. No. 4,732,933; CA Patent No. 1241640; EP Patent No. 0136791; H. Maeda et al., Int. J. Peptide & Protein Res 14, 81-87, 1979; H. Maeda, Adv. Drug Deliv. Rev. 46, 169-185, 2001; and K. Greish, H. Maeda, Drug Delivery System, vol. 18, No. 3, p 254, May 2003 (Abstract of presentation at the Japan Society of Drug Delivery System Annual Meeting)).

SMANCS comprises two SMA chains cross-linked to a small protein, neocarzinostatin (NCS; molecular weight (MW): 12 KDa) by reacting two free amino groups in neocarzinostatin (Ala 1 and Lys 20) with a maleic anhydride residue in the SMA chain (comprising 20 to 45% of maleic anhydride residues, wherein the SMA retains a partial half butyl ester). This reaction is for cross-linking NCS, which is only soluble in water, to a maleic anhydride residue in the SMA chain by forming amide bonds in an alkaline aqueous reaction system. This reaction is expected to comprise hydrolysis of maleic anhydride residues in the SMA chain at alkaline pH in the presence of water molecules at a concentration of 55 M and formation of amide bonds between the maleic anhydride residue and amino groups of NCS (2 molecules) on the coexisting NCS molecule at micromolar range of concentrations. In this reaction, most of the maleic anhydride are exhausted and degraded due to the hydrolysis with largely excessive water, thus a largely excessive amount of SMA is required. It results in the difficulties in the separation and purification of the reaction products [Problem 1].

Maleic anhydride in SMA is hardly soluble, in water, but gradually become water-soluble as the ring of the maleic anhydrides is opened by hydrolysis. However, the reaction of SMA with aromatic (aryl) amines, diethylaminated derivatives of protoporphyrin described below, or amino groups on certain peptides proceeds slowly and thus the yield efficiency of the product (complex) is relatively low [Problem 2].

Small-molecule compounds cross-linked to SMA chains as described above form macromolecular compounds (SMA complexes) comprising copolymers (SMA) of hydrophobic units and hydrophilic units as components and thus easily form micelles by themselves. In brief, it has been found that the SMA conjugates are advantageous in that they form self-association type micelles. As an example of the micelles, the present inventors have successfully synthesized micelles composed of complexes of protoporphyrin (protoporphyrin IX, hereinafter referred to as "PP") and SMA (K. Greish, H. Maeda, Drug Delivery System, vol. 18, No. 3, p254, May 2003; M. Regehly et al., Bioconj. Chem. (2007) vol. 18, 1031-1038; K. Greish, T. Sawa, et al., J. Cont. Release (2004) 97, 219-230; K. Greish, A. Nagamitsu et al., Bioconj. Chem. 16, 230-236, 2005; A. Iyer et al., Biomaterials (2007) vol. 10, 1871-1881; and A. Iyer, K. Greish, T. Seki, S. Okazaki, J. Fang, K. Takeshita, H. Maeda, J. Drug Target 2007, 15, 496-506).

It has been found that PP forms disc-shaped conjugates (aggregates) and the conjugates often form conjugate micelles comprising SMA as a component and conjugating small molecular drugs via a non-covalent bond when the above reaction for binding PP to SMA is performed in an aqueous solution (JP Patent No. 4522452). The SMA-PP conjugate micelles apparently distribute uniformly and normally although they conjugate PP as a noncovalent association. The PP association itself behaves as a micelle of SMA polymers in the aqueous solution. However, it has been found that micelles comprising SMA conjugated to PP via a covalent bond (covalent conjugate) are also formed and coexist (be mixed) with the above micelles comprising the non-covalent conjugated PP in the aqueous solution, and it is thus difficult to separate and purify each micelles [Problem 3].

Therefore, the micelles prepared as described above comprise a mixture of micelles of non-covalent SMA-PP conjugates and micelles of covalent SMA-PP conjugates. When the mixture is administered intravenously, PP in the non-covalent conjugates (micelles) is dissociated from the SMA micelles and released solely. The released PP weakly binds to serum proteins or becomes free PP and thus distributes in liver and/or spleen with high possibilities. It has been found that the decreased amount of PP is moved and accumulated into the targeted lesions, such as tumor sites due to the EPR (Enhanced Permeability and Retention) effect, which is inherent to macromolecular micelles and nanomedicines and thus the risk of hepatic dysfunction is increased (see Cancer Res. 1986, H. Maeda, Adv. Drug Deliv. Rev. 65, 71-79, 2013; H. Maeda, J. Cont. Release 164, 138-144, 2012; and H. Maeda et al., J. Cont. Release 74, 47-61, 2001) [Problem 4].

Further, the conventional SMA micelles are polyanionic and thus the surfaces of the superfine particles have relatively negative charges of −48 to −50 mV. It has been revealed that most of SMA derivatives and micelle particles comprising them accumulate into liver and/or spleen due to the strong negativity (strong negative charge).

Methods for inhibiting the distribution (accumulation) of SMA-derivatives into liver and/or spleen have not been developed so far.

PRIOR ART DOCUMENTS

Patent Documents

Patent Document 1: U.S. Pat. No. 4,182,752
Patent Document 2: U.S. Pat. No. 4,732,933
Patent Document 3: CA Patent No. 1241640
Patent Document 4: EP Patent No. 0136791
Patent Document 5: JP Patent No. 4522452

Non-Patent Documents

Non-Patent Document 1: H. Maeda et al., Int. J. Peptide & Protein Res 14, 81-87, 1979
Non-Patent Document 2: H. Maeda, Adv. Drug Deliv. Rev. 46, 169-185, 2001

Non-Patent Document 3: K. Greish, H. Maeda, Drug Delivery System, vol. 18, No. 3, p254, May 2003 (Abstract of presentation at the Japan society of Drug Delivery System annual meeting)
Non-Patent Document 4: M. Regehly et al., Bioconj. Chem. (2007) vol. 18, 1031-1038.
Non-Patent Document 5: K. Greish, T. Sawa, et al., J. Cont. Release (2004) 97, 219-230
Non-Patent Document 6: K. Greish, A. Nagamitsu et al., Bioconj. Chem. 16, 230-236, 2005
Non-Patent Document 7: A. Iyer et al., Biomaterials (2007) vol. 10, 1871-1881.
Non-Patent Document 8: A. Iyer, K. Greish, T. Seki, S. Okazaki, J. Fang, K. Takeshita, H. Maeda, J. Drug Target 2007, 15, 496-506
Non-Patent Document 9: Cancer Res. 1986, H. Maeda, Adv. Drug Deliv. Rev. 65, 71-79, 2013
Non-Patent Document 10: H. Maeda, J. Cont. Release 164, 138-144, 2012
Non-Patent Document 11: H. Maeda et al., J. Cont. Release 74, 47-61, 2001)

SUMMARY OF THE INVENTION

Problems to be Solved by the Invention

The object of the present invention is to solve the above problems with the conventional SMA-active substance (e.g., drugs such as PP) complexes and to provide a novel SMA derivative capable of providing micelles composed of covalent conjugates of SMA chain and active substance as a single component without comprising impurities such as associations of hydrophobic substances including PP, and noncovalent conjugates such as noncovalent SMA-PP conjugates; a covalent conjugate of said derivative and an active substance; and a method for preparing the same.

Means for Solving the Problem

The present inventors have rigorously investigated to solve the above problems and found that preparing specific derivatives of SMA and binding an active substance covalently to the derivatives make the surface charge almost neutral and lowers the hydrophobicity, which provides a medicament (macromolecular bound nanomedicine) with suppressed accumulation in liver and/or spleen, enhanced EPR effect, and improved water-solubility and higher directivity to tumor sites or inflammatory sites.

The present invention includes the followings:

[1] A styrene-maleic acid copolymer (SMA) derivative comprising:
(i) a styrene-maleic acid copolymer (SMA); and
(ii) a side chain (b) containing a functional group (a) selected from —$NH_2$, —SH, —OH, —COOH, —NH—(C=NH)—$NH_2$ and —C($CH_2$—OH)$_3$, which is introduced into the carboxyl group in the maleic anhydride residue in SMA via an amide bond or an ester bond, wherein when a plurality of side chains (b) are introduced to SMA, the side chains (b) may be identical or different (see, for example, FIG. 1).

[2] The SMA derivative according to the above [1], wherein the side chain (b) is represented by the following formula [A]:

—C(=O)—NH—$R^1$—$R^2$      [A]

wherein $R^1$ is a group selected from a single bond, an alkylene group, —NH—, —CO—, —(C=NH)—, —N=C($CH_3$)—, —(C=NH)—NH—, and a combination thereof, wherein the alkylene group is optionally substituted by a hydroxyl group and a carboxyl group;

$R^2$ is a group selected from a hydrogen atom, —$NH_2$, —SH, —OH, —COOH, —NH—(C=NH)—$NH_2$ and —C($CH_2$—OH)$_3$, provided that when $R^2$ is a hydrogen atom, $R^1$ is a single bond;

wherein when the SMA derivative includes a plurality of groups represented by the formula [A], each $R^1$ and $R^2$ may be identical or different.

[3] The SMA derivative according to the above [2], wherein $R^1$ in the formula [A] is selected from a single bond, —$CH_2$—, —($CH_2$)$_2$—, —($CH_2$)$_3$—, —CH(COOH)—$CH_2$—, —$CH_2$—CH(COOH)—, —$CH_2$—CH(OH)—$CH_2$—, —($CH_2$)$_4$—, —CH(COOH)—($CH_2$)$_3$—, —($CH_2$)$_3$—CH(COOH)—, —($CH_2$)$_3$—CO—CH(COOH)—, —$CH_2$—CO—($CH_2$)$_2$—, —N=C($CH_3$)—($CH_2$)$_2$—, —($CH_2$)$_5$—, —CH(COOH)—($CH_2$)$_4$—, —($CH_2$)$_4$—CH(COOH)—, —($CH_2$)$_4$—NH—(C=NH)—, —(C=NH)—NH—($CH_2$)$_4$—, —CH(COOH)—($CH_2$)$_3$—NH—(C=NH)—, —(C=NH)—NH—($CH_2$)$_3$—CH(COOH)— and —($CH_2$)$_6$—, and those comprising a ketone group on the α, β, γ, or δ carbon atom in the carboxyl groups in the above groups.

[4] The SMA derivative according to the above [2] or [3], wherein —$R^1$—$R^2$ in the formula [A] is selected from the following groups:
(1) a hydrogen atom;
(2) —$NH_2$;
(3) —($CH_2$)$_2$—SH;
(4) —CH(COOH)—$CH_2$—SH;
(5) —($CH_2$)$_{1-6}$—$NH_2$;
(6) —$CH_2$—CH(OH)—$CH_2$—$NH_2$;
(7) —CH(COOH)—($CH_2$)$_4$—$NH_2$;
(8) —($CH_2$)$_{1-4}$—CH(COOH)—$NH_2$;
(9) —($CH_2$)$_{1-4}$—NH—(C=NH)—$NH_2$;
(10) —(C=NH)—NH—($CH_2$)$_{1-4}$—$NH_2$;
(11) —CH(COOH)—($CH_2$)$_3$—NH—(C=NH)—$NH_2$;
(12) —(C=NH)—NH—($CH_2$)$_3$—CH(COOH)—$NH_2$;
(13) —C($CH_2$OH)$_3$;
(14) —($CH_2$)$_{1-4}$—NH—CO—NH—$NH_2$;
(15) —($CH_2$)$_{1-4}$—CO—$CH_2$—$NH_2$;
(16) —$CH_2$—CO—($CH_2$)$_4$—$NH_2$;
(17) —$CH_2$—CO—($CH_2$)$_2$—OH;
(18) —($CH_2$)$_{1-4}$—CO—CHOH—COOH;
(19) —$CH_2$—CO—($CH_2$)$_2$—COOH;
(20) —N=C($CH_3$)—($CH_2$)$_2$—COOH;
(21) —($CH_2$)$_3$—$NH_2$; and
(22) —($CH_2$)$_3$—OH.

[5] A conjugate comprising the SMA derivative according to any one of the above [1] to [4] and an active substance covalently bound directly or indirectly to the SMA derivative.

[6] The conjugate according to the above [5] comprising the SMA derivative according to any one of the above [1] to [4] and an active substance covalently bound directly or indirectly to at least one functional group (a) in the side chain (b) or moiety different from the side chain (b) in the SMA derivative.

[7] The conjugate according to the above [5] or [6] wherein the bond between the SMA derivative and the active substance is selected from an amide bond, an ester bond, a hydrazone bond and a disulfide bond.

[8] The conjugate according to any one of the above [5] to [7], wherein the bond between the functional group (a) in the side chain (b) in the SMA derivative and the active substance is a bond via a linking group —R³—R⁴— as represented by the following formula [B]:

Active substance-R³—R⁴—R²ᵃ-SMA derivative    [B], wherein R³ is a group selected from —NH—, —O—, a carbonyl group, an alkylene group and a combination thereof;
R⁴ is a group selected from —C(CH₃)=N— and —C(benzyl)=N—; and
R²ᵃ is —NH—.

[9] The conjugate according to the above [8] wherein the linking group —R³—R⁴— in the formula [B] is a group selected from the following groups:
(1)    —NH—(CH₂)₂—NH—C(=O)—(CH₂)₂—C(CH₃)=N—, and
(2) —NH—CH₂—C(=O)—(CH₂)₂—C(benzyl)=N—.

[10] The conjugate according to any one of the above [5] to [9], wherein the active substance is an anticancer agent, an antibiotic or a peptide hormone.

[11] The conjugate according to the above [10], wherein the anticancer agent is selected from the group consisting of pirarubicin, protoporphyrin, zinc protoporphyrin, boronomercaptate, boronocysteine, epirubicin, aclarubicin and doxorubicin.

[12] A medicament comprising the conjugate according to any one of the above [5] to [11].

[13] The medicament according to the above [12], which is a carcinostatic agent.

[14] A pharmaceutical composition comprising the conjugate according to any one of the above [5] to [11] and a pharmaceutically acceptable carrier.

[15] A use of the conjugate according to any one of the above [5] to [11] as a medicament.

[16] A use of the conjugate according to any one of the above [5] to [11] for manufacturing a pharmaceutical composition.

[17] A method for treating or preventing diseases, comprising administering the conjugate according to any one of the above [5] to [11] to a patient.

Effect of the Invention

The SMA derivative of the present invention with basic moieties added to the SMA chain and micelles formed from the derivatives have lower negative surface charge. For example, the zeta potential of the original SMA surface of −48 mV to −50 mV may be reduced to about −40 to −5 mV by deriveratization. Further, the carboxyl groups in maleic acids in SMA are neutralized by an amide bond even in the absence of basic components. Further, when the derivative comprises ester bonds derived from alcohol, etc., the negative charge may be reduced (see Table 4 below). When the derivative comprises a hydrophilic group such as a tris group, the hydrophicity is also reduced. Therefore, the derivative of the present invention may be used for preparing a conjugate advantageously useful as a medicament as described below.

The conjugate of the present invention is a covalent conjugate of the SMA derivative with a novel structure and an active substance, and
(1) is a macromolecular with a diameter of 10 nm to 3000 nm in an aqueous solution and exhibits EPR effect;
(2) releases the drug at a low acidic pH in tumors locally (see FIG. 2) or under a reducing condition and thus allows the original low molecular drug to diffuse into tumors locally and to be incorporated rapidly by tumor cells; and
(3) exhibits increased tumor-selective efficacy.

Further, the conjugate of the present invention
(4) can provide an innovative nanomedicine carcinostatic agent because the conjugate (macromolecule) and micelles formed by the conjugates have less negative surface charge, especially when basic moieties are added to the SMA chain, thereby suppressing the non-specific binding to liver and/or spleen; they maintain a high concentration in blood and accomplish a high concentration in tumors due to the enhanced EPR effect, caused by the improved water-solubility; and they have reduced toxicity due to suppressed accumulation in normal tissues.

BRIEF EXPLANATION OF THE DRAWINGS

FIG. 1 shows a reaction scheme for synthesizing the novel SMA derivatives of the present invention (hydrazinated SMA, amidated SMA, tris-SMA, aminated SMA and thiolated SMA) from the styrene-maleic anhydride copolymers (SMA).

FIG. 2 shows the releasing rate of THP (pirarubicin) from SMA-hydrazone-THP under each different pH conditions.

FIG. 3A: SMA-maleic anhydride copolymers (unreacted material);
FIG. 3B: hydrazinated SMA derivative, the reaction product prepared with 2 molar excess amount of hydrazine in a water system in Example 2;
FIG. 3C: the reaction product prepared with 5 molar excess amount of hydrazine in Example 2;
FIG. 3D: amidated SMA derivative, the reaction product prepared with 50 molar excess amount of ammonia in Example 12;
FIG. 3E: tris-SMA derivative, the reaction product prepared with 5 molar excess amount of L- cysteine in dimethylformamide (DMF) in Example 27;
FIG. 3F: cysteine-SMA derivative, the reaction product preapred with 5 molar excess L- cysteine in DMF in Example 18;
FIG. 3G: SMA-hydrazyl-THP (pirarubicin) obtained in Example 6;
and
FIG. 3H: hydrazine hydrate (unreacted material).

FIG. 4A: control cysteine; the spectrum has a remarkable SH peak;
FIG. 4B: cysteine-SMA derivative obtained in Example 18;
and
FIG. 4C: control cystine; the spectrum has a significant S-S peak.

FIG. 5 is a graph showing the antitumor effect of SMA-THP in S-180 mice.

FIG. 6 shows survival rates after starting the treatment of mouse S-180 with SMA-THP.

DESCRIPTION OF THE EMBODIMENTS

Figure 3A:
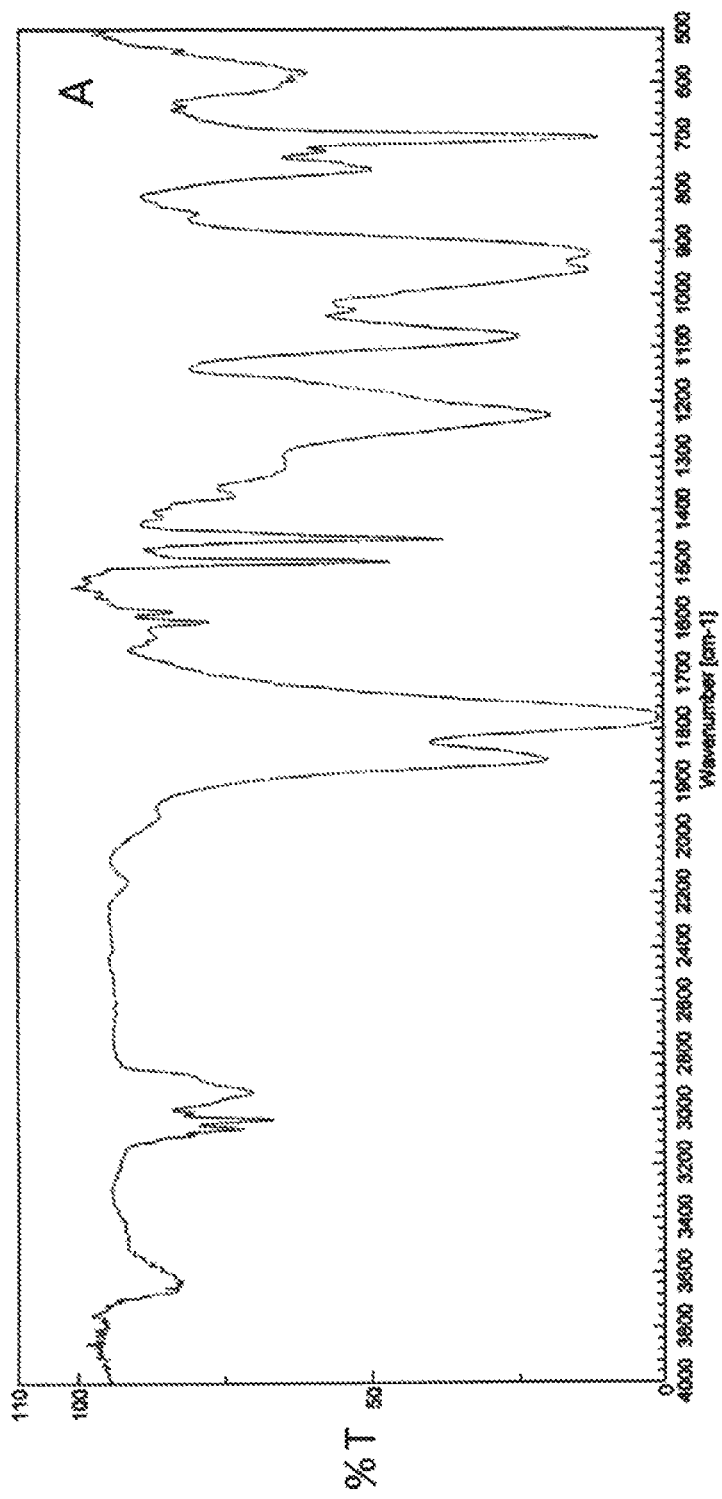
FIGS. 3A-3H shows the infrared absorption spectra/KBr of the following substances.
Figure 3B:
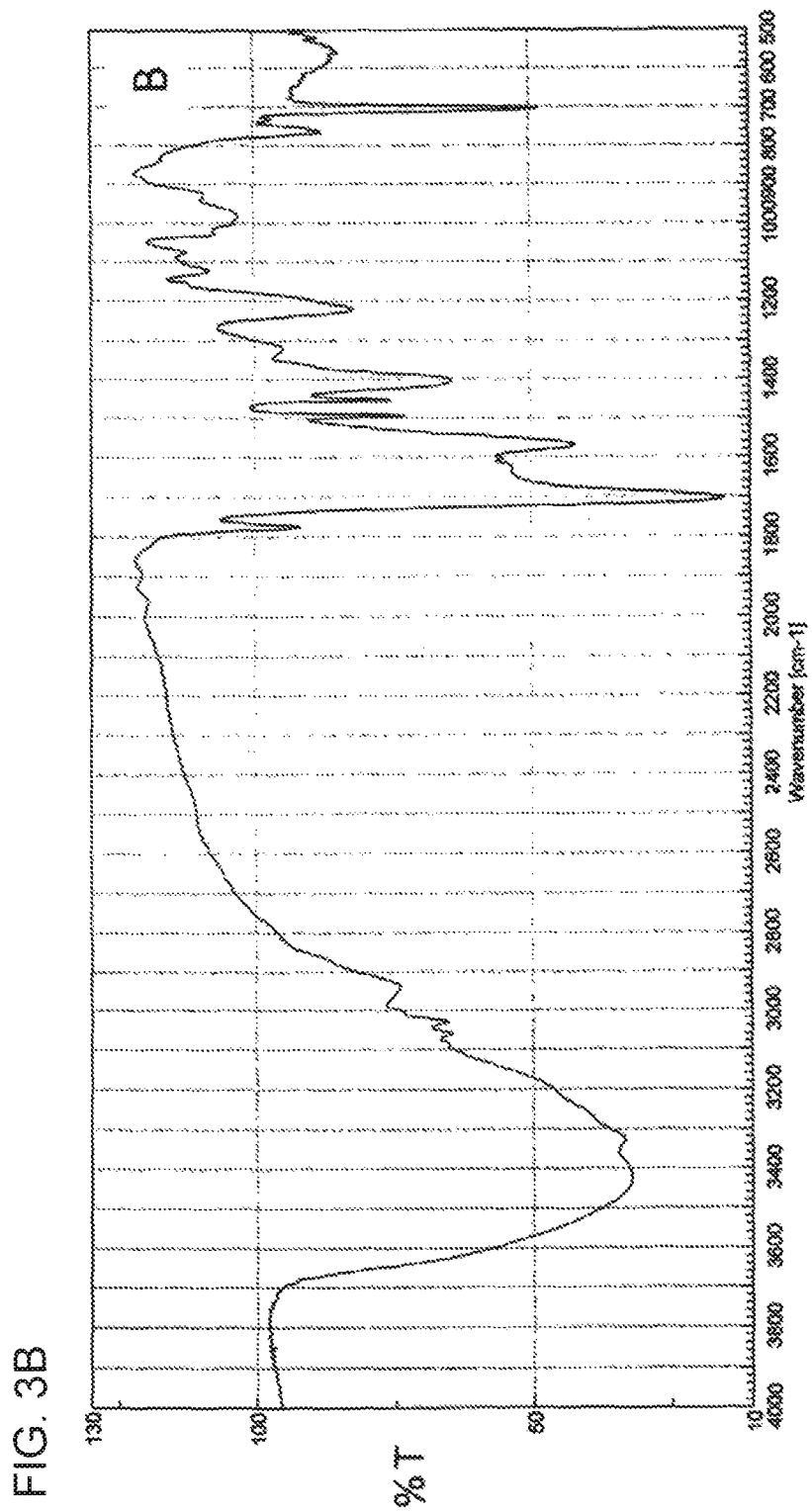
Figure 3C:
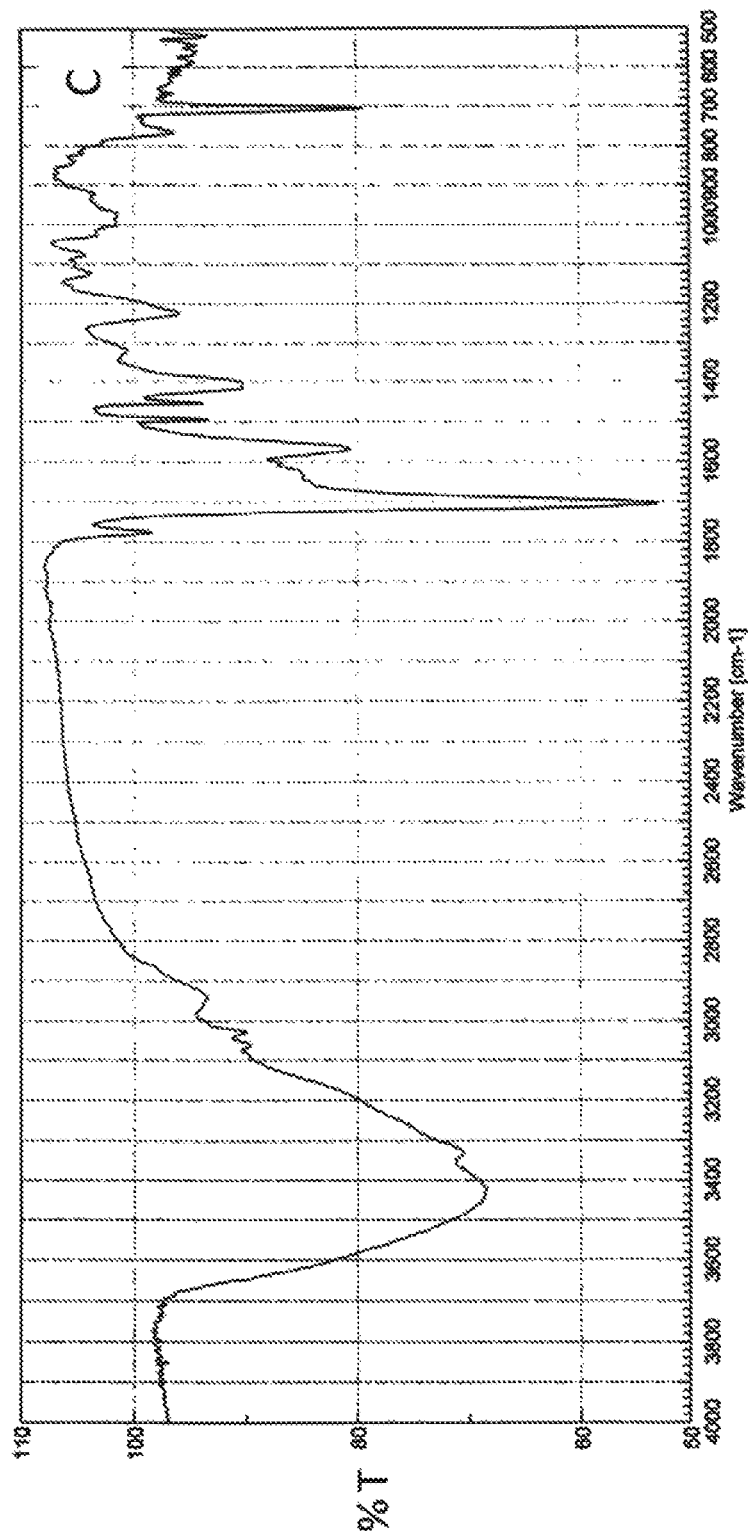
Figure 3D:
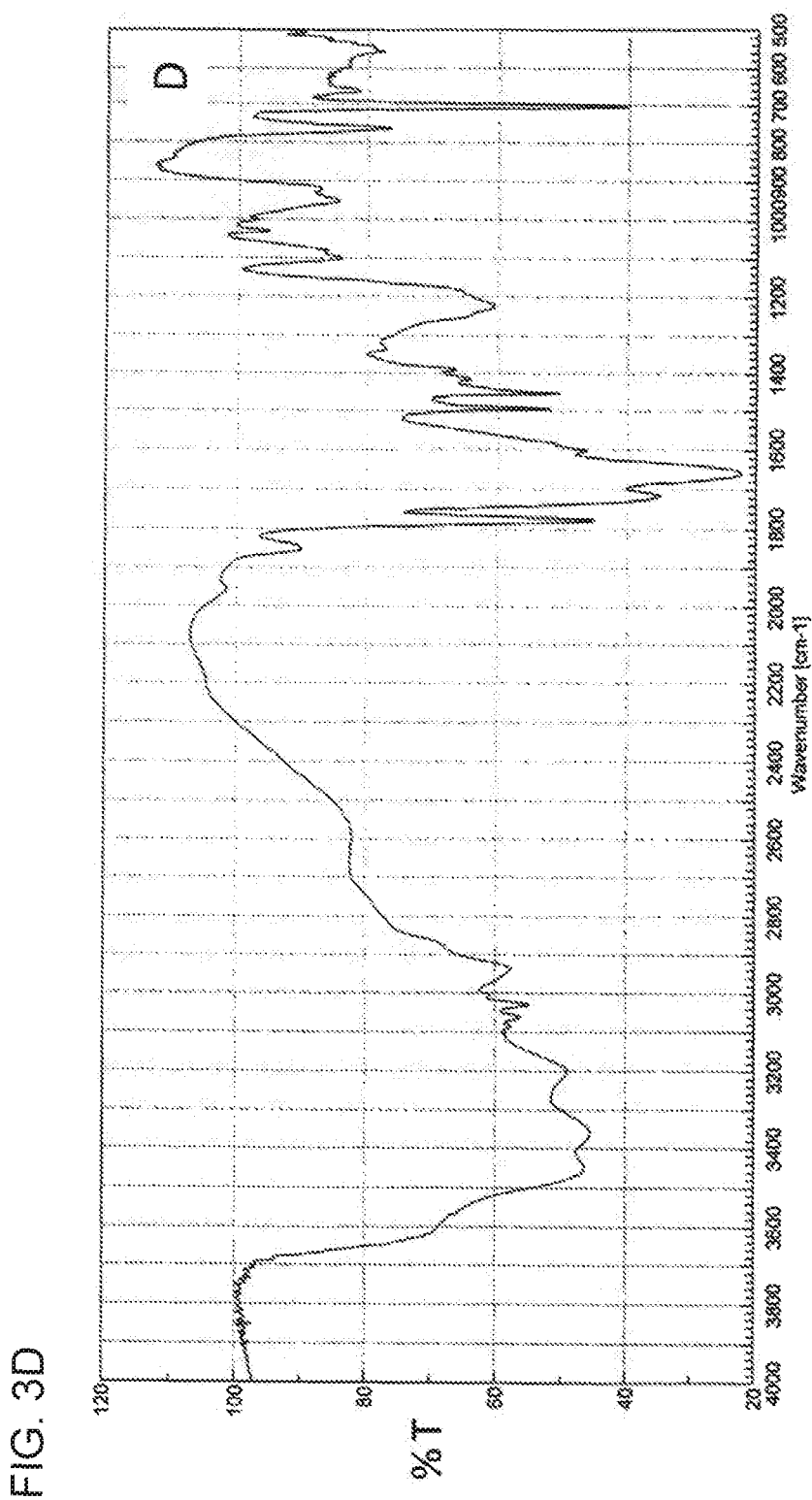
Figure 3E:
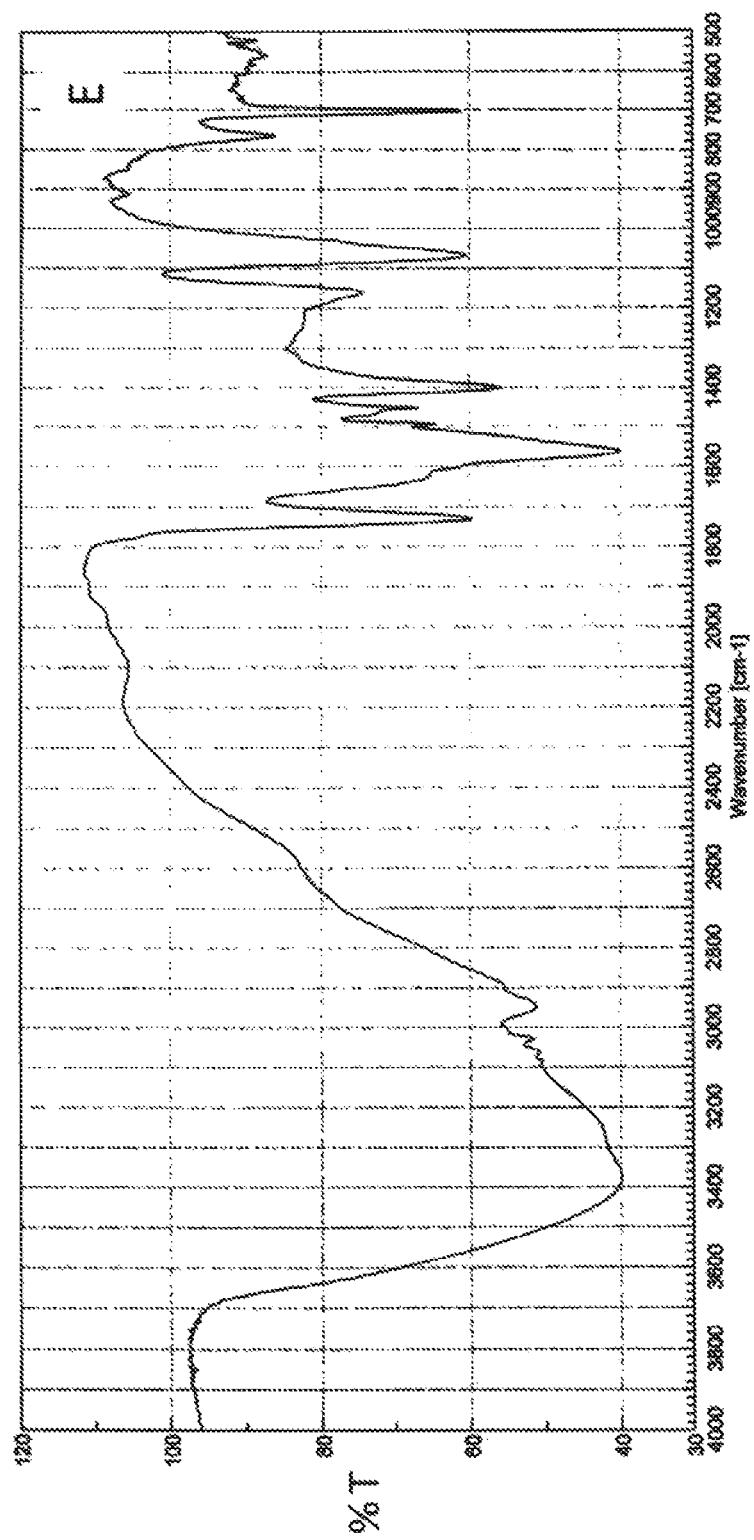
Figure 3F:
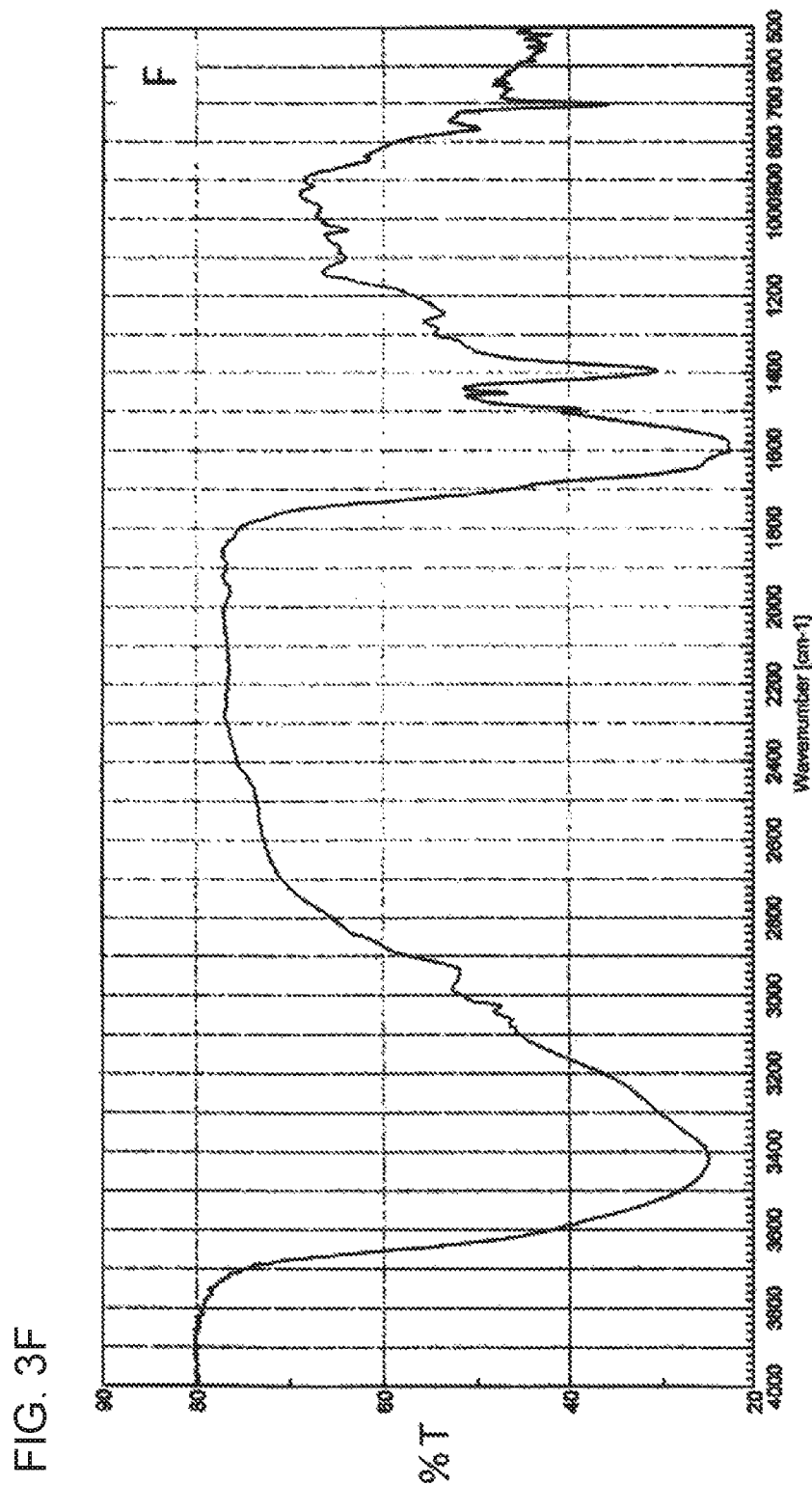
Figure 3G:
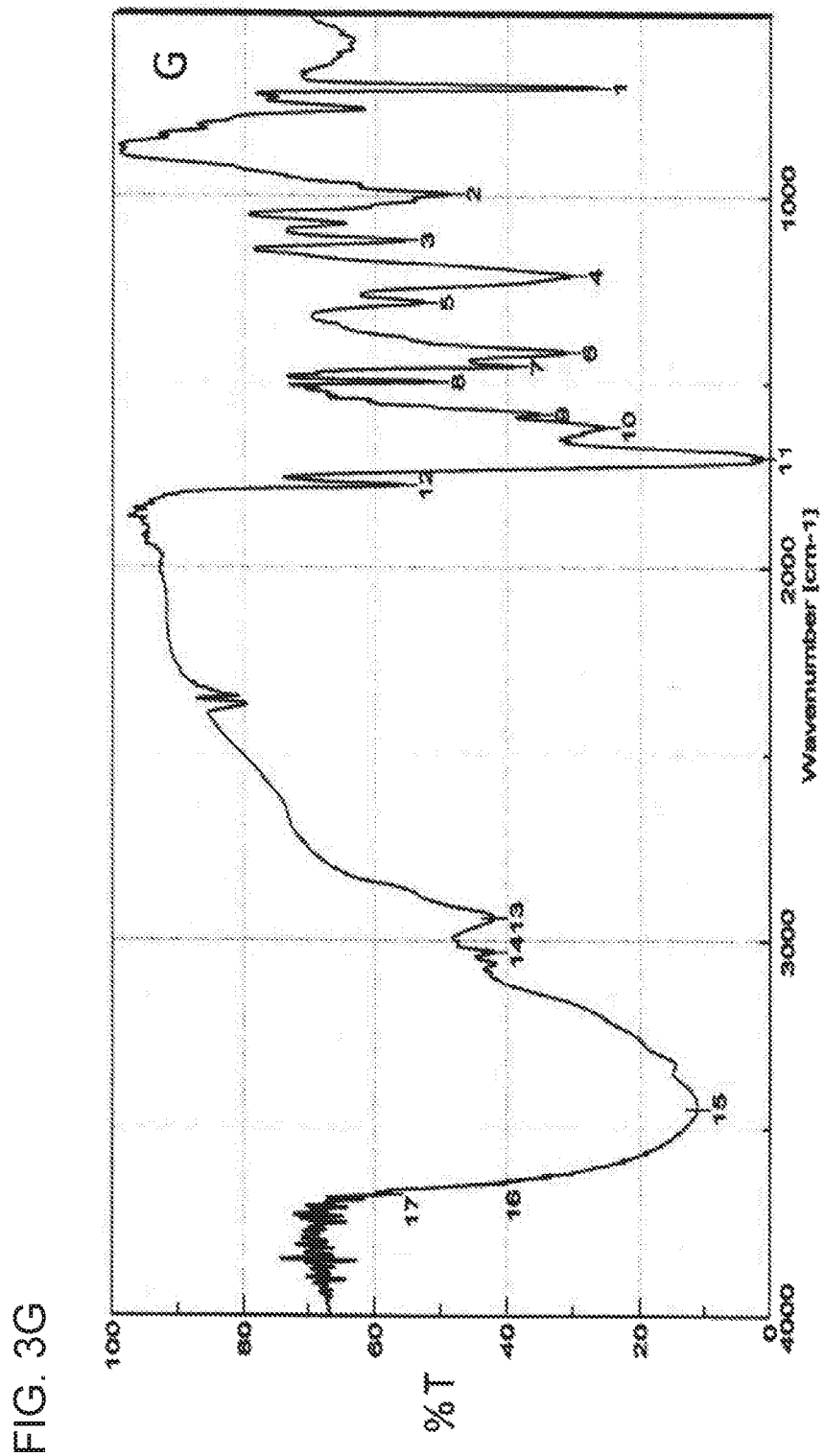
Figure 3H:
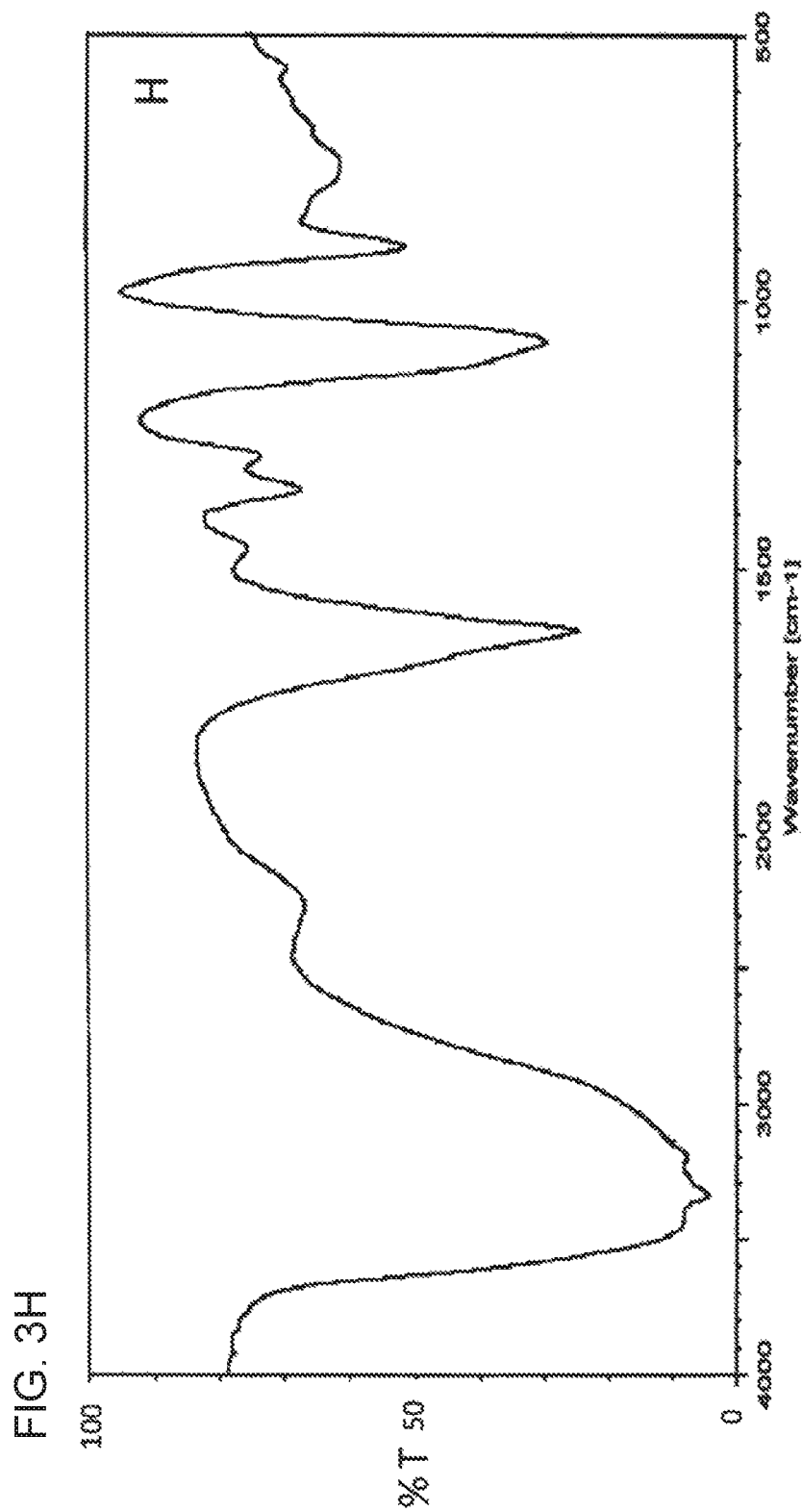

The present invention provides a styrene-maleic acid copolymer (SMA) derivative comprising SMA and a side chain (b) containing a functional group (a) selected from —NH₂, —SH, —OH, —COOH, —NH—(C=NH)—NH₂ and —C(CH₂—OH)₂, wherein the side chain (b) is introduced into the carboxyl group in the maleic residue in SMA via amide bond or ester bond. When a plurality of side chains (b) are introduced, the side chains may be identical or different.

In an embodiment, the side chain (b) comprises a functional group (a) selected from —NH$_2$, —SH, —NH—(C═NH)—NH$_2$ and —C(CH$_2$—OH)$_3$, which is introduced into the carboxyl group in the maleic acid residue in SMA via amide bond.

The SMA derivatives of the present invention may be obtained by the use of a modifier, such as ammonia, hydrazine, 2-aminoethanethiol, cysteine, diaminoalkyl (for example, diaminoethane, diaminopropane and diaminohexane), diaminopropanol, aminopropanol, lysine, guanidylbutylamine, arginine, tris(hydroxymethyl)aminomethane, keto acid (for example, levulininc acid, δ-aminolevulinic acid) or a salt thereof (such as a salt of alkali metal including sodium).

A plurality of modifier may be used simultaneously or sequentially. For example, a hydrazino group may be added to SMA by modifying the carboxyl group in SMA with hydrazine, and then levulinic acid may be further added to SMA by reacting said hydrazino group (or amino group) with the ketone group in the levulinic acid.

The side chain (b) in the SMA derivative of the present invention is preferably represented by the formula [A]:

—C(═O)—NH—R$^1$—R$^2$ [A]

wherein, R$^1$ is a group selected from a single bond, an alkylene group, —NH—, —CO—, —(C═NH)—, —N═C(CH$_3$)—, —(C═NH)—NH— and a combination thereof, wherein the alkylene group is optionally substituted by a hydroxyl group or a carboxyl group;

R$^2$ is a group selected from hydrogen atom, —NH$_2$, —SH, —OH, —COOH, —NH—(C═NH)—NH$_2$ and —C(CH$_2$—OH)$_3$, provided that when R$^2$ is hydrogen atom, R$^1$ is a single bond. When the SMA derivative has a plurality of groups represented by the formula [A], each R$^1$ and R$^2$ may be identical or different.

Examples of the above alkylene group include a linear or branched alkylene group having 1 to 20 carbon atoms, such as methylene, trimethylene, tetramethylene, pentamethylene, hexamethylene, heptamethylene, octamethylene, and the like. Preferred is a linear or branched alkylene group having 1 to 6 carbon atoms, such as methylene, dimethylene, trimethylene, tetramethylene, pentamethylene, hexamethylene and the like. Particularly preferred is a linear or branched alkylene group having 1 to 4 carbon atoms, such as methylene, dimethylene, trimethylene, tetramethylene and the like.

Said alkylene group may be substituted with a hydroxyl group, a carboxyl group, and the like.

In an embodiment, R$^1$ in the above formula [A] is a group selected from a single bond, an alkylene group, —(C═NH)—NH— and a combination thereof, and R$^2$ is a group selected from a hydrogen atom, —NH$_2$, —SH, —NH—(C═NH)—NH$_2$ and —C(CH$_2$—OH)$_3$.

In the above formula [A], R$^1$ is preferably selected from a single bond, —CH$_2$—, —(CH$_2$)$_2$—, —(CH$_2$)$_3$—, —CH(COOH)—CH$_2$—, —CH$_2$—CH(COOH)—, —CH$_2$—CH(OH)—CH$_2$—, —(CH$_2$)$_4$—, —CH(COOH)—(CH$_2$)(CH$_2$)$_3$—CH(COOH)—, —(CH$_2$)$_3$—CO—CH(COOH)—, —CH$_2$—CO—(CH$_2$)$_2$—, —N═C(CH$_3$)—(CH$_2$)$_2$—, —(CH$_2$)$_5$—, —CH(COOH)—(CH$_2$)$_4$—, —(CH$_2$)$_4$—CH(COOH)—, —(CH$_2$)$_4$—NH—(C═NH)—, —(C═NH)—NH—(CH$_2$)$_4$—, —CH(COOH)—(CH$_2$)$_3$—NH—(C═NH)—, —(C═NH)—NH—(CH$_2$)$_3$—CH(COOH)—, —(CH$_2$)$_6$— and those with a ketone group on the α, β, γ, or δ-carbon atom in the carboxyl group in the above groups.

In an embodiment, R$^1$ in the above formula [A] is a single bond, —(CH$_2$)$_2$—, —CH(COOH)—CH$_2$—, —CH$_2$—CH(COOH)—, —CH$_2$—CH(OH)—CH$_2$—, —(CH$_2$)$_4$—, —CH(COOH)—(CH$_2$)$_3$—, —(CH$_2$)$_3$—CH(COOH)—, —(CH$_2$)$_5$—, —CH(COOH)—(CH$_2$)$_4$—, —(CH$_2$)$_4$—CH(COOH)—, —(CH$_2$)$_4$—NH—(C═NH)—, —(C═NH)—NH—(CH$_2$)$_4$—, —CH(COOH)—(CH$_2$)$_3$—NH—(C═NH)—, —(C═NH)—NH—(CH$_2$)$_3$—CH(COOH)— or —(CH$_2$)$_6$—.

In the above formula [A], —R$^1$—R$^2$ is preferably selected from the following groups:
(1) a hydrogen atom (for example, obtained by the use of ammonia as a modifier);
(2) —NH$_2$ (for example, obtained by the use of hydrazine as a modifier);
(3) —(CH$_2$)$_2$—SH (for example, obtained by the use of 2-aminoethanethiol as a modifier);
(4) —CH(COOH)—CH$_2$—SH (for example, obtained by the use of cysteine as a modifier);
(5) —(CH$_2$)$_{1-6}$—NH$_2$ (for example, obtained by the use of diaminoethane or diaminohexane as a modifier);
(6) —CH$_2$—CH(OH)—CH$_2$—NH$_2$ (for example, obtained by the use of diaminopropanol as a modifier);
(7) —CH(COOH)—(CH$_2$)$_4$—NH$_2$ (for example, obtained by the use of lysine as a modifier);
(8) —(CH$_2$)$_{1-4}$—CH(COOH)—NH$_2$ (for example, obtained by the use of lysine as a modifier);
(9) —(CH$_2$)$_{1-4}$—NH—(C═NH)—NH$_2$ (for example, obtained predominantly by the use of guanidylbutylamine as a modifier);
(10) —(C═NH)—NH—(CH$_2$)$_{1-4}$—NH$_2$ (for example, obtained by the use of guanidylbutylamine as a modifier);
(11) —CH(COOH)—(CH$_2$)$_3$—NH—(C═NH)—NH$_2$ (for example, obtained predominantly by the use of arginine as a modifier);
(12) —(C═NH)—NH—(CH$_2$)$_3$—CH(COOH)—NH$_2$ (for example, obtained by the use of arginine as a modifier);
(13) —C(CH$_2$—OH)$_3$ (for example, obtained by the use of tris(hydroxymethyl)aminomethane as a modifier);
(14) —(CH$_2$)$_{1-4}$—NH—CO—NH—NH$_2$ (for example, obtained predominantly by the use of δ-keto acid and the like as a modifier);
(15) —(CH$_2$)$_{1-4}$—CO—CH$_2$—NH$_2$;
(16) —CH$_2$—CO—(CH$_2$)$_4$—NH$_2$;
(17) —CH$_2$—CO—(CH$_2$)—OH;
(18) —(CH$_2$)$_{1-4}$—CO—CHOH—COOH and the like (for example, obtained by the use of keto acid such as δ-aminolevulinate as a modifier);
(19) —CH$_2$—CO—(CH$_2$)$_2$—COOH (for example, obtained by the use of δ-aminolevulinic acid or a salt thereof as a modifier);
(20) —N═C(CH$_3$)—(CH$_2$)$_2$—COOH (for example, obtained by the use of levulinic acid or a salt thereof as a modifier);
(21) —(CH$_2$)$_3$—NH$_2$ (for example, obtained by the use of diaminopropane as a modifier); and
(22) —(CH$_2$)$_3$—OH (for example, obtained by the use of diaminopropanol as a modifier).

More preferably, —R$^1$—R$^2$ is selected from the following groups:
(1) a hydrogen atom (for example, obtained by the use of ammonia as a modifier);
(2) —NH$_2$ (for example, obtained by the use of hydrazine as a modifier);
(3) —(CH$_2$)$_2$—SH (for example, obtained by the use of 2-aminoethanethiol as a modifier);
(4) —CH(COOH)—CH$_2$—SH (for example, obtained by the use of cysteine as a modifier);

(5) —C(CH$_2$—OH)$_3$ (for example, obtained predominantly by the use of tris(hydroxymethyl)aminomethane as a modifier);
(6) —(CH$_2$)$_{1-4}$—NH—CO—NH—NH$_2$ (for example, obtained by the use of δ-keto acid and the like as a modifier);
(7) —(CH$_2$)$_3$—NH$_2$ (for example, obtained by the use of diaminopropane as a modifier); and
(8) —(CH$_2$)$_3$—OH (for example, obtained by the use of diaminopropanol as a modifier).

In an embodiment, —R$^1$—R$^2$ in the above formula [A] is preferably selected from the following groups:
(1) a hydrogen atom (for example, obtained by the use ammonia as a modifier);
(2) —NH$_2$ (for example, obtained by the use of hydrazine as a modifier);
(3) —(CH$_2$)$_2$—SH (for example, obtained by the use of 2-aminoethanethiol as a modifier);
(4) —CH(COOH)—CH$_2$—SH (for example, obtained by the use cysteine as a modifier);
(5) —(CH$_2$)$_2$—NH$_2$ (for example, obtained by the use of diaminoethane as a modifier);
(6) —CH$_2$—CH(OH)—CH$_2$—NH$_2$ (for example, obtained by the use of diaminopropanol as a modifier);
(7) —(CH$_2$)$_6$—NH$_2$ (for example, obtained by the use of diaminohexane as a modifier);
(8) —CH(COOH)—(CH$_2$)$_4$—NH$_2$ (for example, obtained predominantly by the use of lysine as a modifier);
(9) —(CH$_2$)$_4$—CH(COOH)—NH$_2$ (for example, obtained by the use of lysine as a modifier);
(10) —(CH$_2$)$_4$—NH—(C=NH)—NH$_2$ (for example, obtained predominantly by the use of guanidylbutylamine as a modifier);
(11) —(C=NH)—NH—(CH$_2$)$_4$—NH$_2$ (for example, obtained by the use of guanidylbutylamine as a modifier);
(12) —CH(COOH)—(CH$_2$)$_3$—NH—(C=NH)—NH$_2$ (for example, obtained predominantly by the use of arginine as a modifier);
(13) —(C=NH)—NH—(CH$_2$)$_3$—CH(COOH)—NH$_2$ (for example, obtained by the use of arginine as a modifier); and
(14) —C(CH$_2$OH)$_3$ (for example, obtained by the use of tris(hydroxymethyl)aminomethane as a modifier).

In an embodiment, —R$^1$—R$^2$ is more preferably selected from the followings:
(1) a hydrogen atom (for example, obtained by the use of ammonia as a modifier);
(2) —NH$_2$ (for example, obtained by the use of hydrazine as a modifier);
(3) —(CH$_2$)$_2$—SH (for example, obtained by the use of 2-aminoethanethiol as a modifier);
(4) —CH(COOH)—CH$_2$—SH (for example, obtained by the use of cysteine as a modifier); and
(5) —C(CH$_2$OH)$_3$ (for example, obtained by the use of tris(hydroxymethyl)aminomethane as a modifier).

The "styrene-maleic acid (including maleic anhydride) copolymer" (SMA) herein is a copolymer comprising a unit derived from styrene (a styrene residue) and a unit derived from maleic acid or maleic anhydride (a maleic acid or maleic anhydride residue) as repeating units, for example, as shown in the formula [1] below (the formula comprises a maleic anhydride residue). SMA may be obtained in the market, or synthesized by known procedures. The polymerized form of styrene and maleic acid or maleic anhydride is not particularly limited and may be any form of random polymerization, block polymerization and graft polymerization.

The ratio of styrene residue:maleic acid residue is most preferably 1:1, while any ratio such as 3:1 to 1:10 may be used. For example, SMA with a ratio of 2:1 from Polyscience may be used. SMA is generally obtained by copolymerization of styrene and maleic anhydride. In this case, the moiety from the maleic anhydride group is a cyclic acid anhydride and can be used as is, or as free acid obtained by hydrolysis before use. In the present invention, maleic anhydride is preferably used for derivatizing SMA.

A reaction solvent which may be used in the copolymerization includes, not particularly limited to, dimethylformamide (DMF), tetrahydrofuran (THF), dimethyl sulfoxide (DMSO), water, dimethylacetamide (DMAC), methyl cellosolv, ethyl acetate ester, acetone, acetonitrile and the like. In some cases, the solvent includes, but not limited to, methanol, ethanol, butanol and propanol.

The molecular weight of the above SMA may vary depending on the polymerization degree. For example, the SMA used in the present invention preferably comprises repeat units with a polymerization degree (n) of about 3 to 250 with a molecular weight of about 500 to 50,000 as shown in the formula [1]. Examples of SMA include SMA Resins (trade name) from Sartomer (USA).

At least one acid group such as a carboxyl group or basic group such as an amino group in the maleic acid residues or the side chains (b) in the SMA derivative of the present invention may form a salt. The salt is preferably a pharmaceutically acceptable salt, including salts with inorganic bases (for example, ammonium salt; salts with alkali metals such as sodium, potassium and lithium; salts with alkaline earth metals such as calcium and magnesium; aluminium salts); salts with organic bases (for example, salts with alkyl amines such as methylamine, dimethylamine, trimethylamine and triethylamine; salts with cycloalkylamines such as dicyclohexylamine; salts with alkanol amines such as ethanolamine, diethanolamine and triethanolamine; salts with amino acids such as α-amino acids and δ-aminolevulinic acid; salts with heterocyclic amines such as pyridine and picoline; salts with alkylenediamide derivatives, such as N,N-dibenzylethylenediamine). These salts may be prepared by known procedures.

At least one carboxyl group or hydroxyl group in the maleic acid residues or the side chains (b) in the SMA derivative of the present invention may form an ester. Examples of the ester include those formed with alkyl groups having 1 to 4 carbon atoms (such as methyl group, ethyl group, propyl group and butyl group) and those formed with acyl groups having 1 to carbon atoms (such as acetyl group, propionyl group and δ-aminolevulinic acid). These esters may be synthesized by known procedures. Further, the SMA derivatives may be prepared from the SMA with at least one carboxyl group esterified by an alkyl group or an acyl group in the maleic acid residues as mentioned above.

When a plurality of side chains (b) are introduced to the SMA derivative of the present invention, the functional groups (a) in the side chains (b) may be identical or different. For example, the SMA derivative of the present invention may contain —NH$_2$, —SH and/or —NH—(C=NH)—NH$_2$ in addition to —C(CH$_2$—OH)$_3$.

The SMA derivative of the present invention may be prepared through reactions with modifiers for introducing various functional groups (a) into the above maleic acid (or maleic anhydride) residue in the SMA.

As examples of the SMA derivative of the present invention, the methods for preparing (1) hydrazinated SMA, (2)

amidated SMA, (3) thiolated SMA, (4) aminated SMA, (5) tris-SMA and (6) aminolevulinate SMA will be illustrated below (see FIG. 1).

(1) Hydrazinated SMA

A hydrazinated SMA derivative (hydrazinated SMA) may be prepared by reacting SMA with a hydrazinating agent. Examples of the hydrazinating agent include hydrazine monohydrate, which is generally referred to as hydrazine.

SMA may be hydrazinated, for example, according to the following reaction scheme.

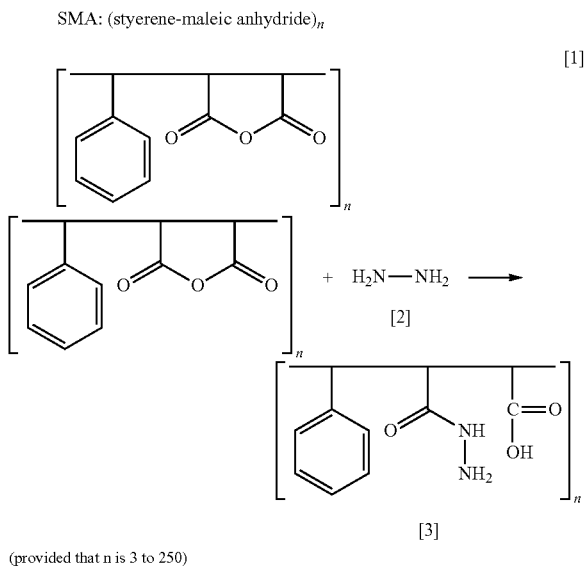

(provided that n is 3 to 250)

For example, a hydrazinated SMA with hydrazinated maleic anhydride residues [3] may be prepared by the reaction of the maleic anhydride residues in the styrene-maleic anhydride copolymer having about 3 to 250 repeat units [1] with hydrazine [2].

After the above reaction, the maleic anhydride residues in SMA become monocarboxylic acid, instead of dicarboxylic acid generated via alkaline hydrolysis in an aqueous reaction system, which reduces the negative charge by half. When the amount of hydrazine used in the reaction is less than the equivalent amount of maleic anhydride, unreacted maleic anhydride residues may be maintained in various ratios depending on the amount of hydrazine. The remaining maleic anhydride residues may be used for cross-linking to another functional compound comprising amino group.

The amount of the hydrazine used in the above reaction is, for example, 1 to 20 equivalents, preferably 2 to 3 equivalents based on the amount of the maleic anhydride residues in SMA chain. In general, the use of not less than 2 mole equivalents of the hydrazine based on the maleic anhydride residues provides a SMA derivative in which all maleic anhydride residues are hydrazinated.

The above reaction may be performed in an aqueous system or in an organic solvent system.

When the above reaction is performed in an aqueous solution system, an aqueous solution comprising a certain amount of hydrazine is prepared. To the solution is added a certain amount of SMA and the reaction is performed under stirring.

The concentration of the hydrazine aqueous solution in this reaction is not particularly limited. For example, to 20 ml of water are added 0.1 to 1 ml, preferably 0.15 ml (3 mmol) of hydrazine monohydrate and 0.1 to 2 g, preferably 0.3 g (1.3 mmol) of SMA anhydride, and then a mixture is reacted at room temperature. The reaction mixture is at first a suspension and gradually becomes a solution to provide a hydrazinated SMA-maleic acid during the reaction, preferably 24 hours later. When the equiv. mole equivalent of hydrazine is added to the reaction in an amount less than that of maleic anhydride, unreacted maleic anhydride remains. In this case, the reaction is performed for 1 to 10 hours, preferably 2 to 3 hours. The reaction may be performed in an organic solvent such as dimethylformamide (DMF) instead of in water. When the reaction is performed in an organic solvent system, a certain amount of SMA is dissolved in the organic solvent to obtain a solution, and then the solution is added with a certain amount of hydrazine and reacted under stirring. In this case, examples of the solvent include DMF, dimethyl sulfoxide (DMSO) and dimethylacetamide ($DMA_c$), preferably DMF. The above reaction temperature is not particularly limited to room temperature, but may be, for example, 16° C. to 70° C., preferably 25° C. to 37° C. The reaction time is not particularly limited, but may be, for example, 2 to 50 hours, preferably 10 to 20 hours.

After the completion of the reaction, according to the conventional method, water is added to the DMF solution to be not less than 50% of water, and then the obtained solution is dialyzed/concentrated against 5% amount of aqueous sodium bicarbonate followed by distilled water and lyophilized. The product may be concentrated and filtered through a molecular membrane (Cut-off: MW 2000 or 5000) to remove unreacted hydrazine, degradates and other salts, or adjusted the pH to 4 or less with hydrochloric acid to provide precipitates, or lyophilzed from the aqueous solution, to obtain a white powder of hydrazinated SMA.

Further, hydrazinated SMA may be prepared by similar reactions with other hydrazinating agents.

(2) Amidated SMA

Amidated SMA derivative (amidated SMA) may be prepared by reacting SMA with an amidating agent. Examples of the amidating agents include concentrated aqueous ammonia (28 to 29% $NH_3$), liquid ammonia (100% $NH_3$), preferably, concentrated aqueous ammonia.

For example, SMA may be amidated according to the following reaction scheme:

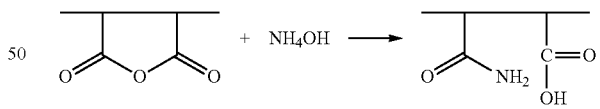

For example, concentrated aqueous ammonia (represented as $NH_4OH$ in the above reaction formula) is added to a suspension of SMA in water for the ammonolysis of the maleic anhydride residues in SMA. This reaction provides amidated SMA.

The amount of the ammonia used in the above reaction is, for example, 1 to 100 equivalents, preferably 10 to 20 equivalents based on the maleic anhydride residues. In general, 5 equivalents or more of ammonia based on the maleic anhydride residues may amidate 90% or more of the maleic anhydride residues in SMA. When it is necessary to retain untreated maleic anhydride residues, the amount of the ammonia used in the reaction is 1 mole equivalent or less, preferably 0.5 mole equivalents.

The above reaction may be performed in an aqueous solution system or in an organic solvent system.

When the above reaction is performed in an aqueous system, generally, a certain amount of SMA is suspended in water, and to the suspension is added a certain amount of concentrated aqueous ammonia, and then the mixture is reacted under stirring. The amount of SMA used in this reaction is not particularly limited but, for example, 500 mg to 10 g, preferably 500 mg to 3 g per 1 l of water. The reaction temperature is not particularly limited but, for example, 10° C. to 70° C., preferably 30° C. to 60° C. The reaction time is not particularly limited but, for example, 3 to 48 hours, preferably 20 to 40 hours. The pH of this reaction system is 10 or more.

The reaction is generally performed for about 40 hours for the complete ring opening of maleic anhydride residues. The reaction is performed for 5 to 10 hours, for example, for leaving 1 to 4 of 8 maleic anhydride residues unreacted. The reaction time, temperature and the amount of ammonia may vary as required.

When the reaction is performed in an organic solvent system, a certain amount of SMA is generally dissolved in the organic solvent, and then concentrated aqueous ammonia is added to the solution and the mixture is reacted under stirring. Examples of the organic solvents which may be used in this reaction include dimethylformamide (DMF), which is used in a similar manner to water.

As another amidating agent, 100 ml of liquid ammonia cooled to −60° C. is placed in a 300 ml beaker, and then 1.0 to 30 g, preferably 3 g or more of SMA powders are gradually added to the liquid ammonia under stirring to obtain a clear solution. The concentration of the SMA solution is not particularly limited but, for example, 1 to 30%, preferably 10 to 20%. The reaction temperature is not particularly limited but, for example, 20 to 80° C., preferably 30 to 50° C. The reaction is not limited but, for example, for safe experimental operations, 10 to 24 hours, preferably for 5 to 6 hours under a temperature of −30° C. to −60° C. where ammonia exists in a liquid form, preferably about −30° C. under boiling.

After the completion of the reaction, the reaction liquid is applied to filtration, dialysis, concentration and the like. Unreacted ammonia may be removed by evaporation at −33° C. The residue is then dissolved in about 200 ml of distilled water under stirring. Then, 0.1 M hydrochloric acid is added under stirring to remove the unreacted SMA, SMA with low amidation degree, degradation products and other salts remaining in the fraction by precipitating them at pH 5 to 5.0 by fractional precipitation. The remaining solution is dialyzed with neutral distilled water, and lyophilized to obtain amidated SMA.

The amidated SMA may be also prepared by a similar procedure with other amidating agents.

(3) Thiolated SMA

Thiolated SMA derivative (thiolated SMA) may be prepared by reacting SMA with a thiolating agent (the reaction scheme is shown in the FIG. 1). Examples of the thiolating agent include aminoalkyl mercaptan (for example, 2-aminoethanethiol), cysteine (particularly, L-cysteine), (reduced) glutathione, preferably 2-aminoethanethiol and L-cysteine.

For example, when the thiolating agent is L-cysteine, a thiolated SMA may be obtained by, for example, dissolving SMA in an organic solvent such as dimethylformamide (DMF), adding L-cysteine to the solution, and then reacting the maleic anhydride residues with amino groups in L-cysteine.

The amount of L-cysteine used in the above reaction is, for example, 1 to 30, preferably 2 to 10 molar excess equivalents based on the maleic anhydride residues.

The above reaction may be performed in an organic solvent system or a weak alkaline aqueous solution system.

In general, a certain amount of SMA is dissolved in an organic solvent to obtain a solution of SMA. To the solution is added a certain amount of aminoalkyl mercaptane compound (the compound represented as $H_2N$—R—SH in FIG. 1, wherein R is any alkyl group; or the formula itself represents an organic acid (a fatty acid) with a SH group on the ω terminal, for example, L-cysteine) and then the mixture is reacted under stirring. Examples of the organic solvent used in this reaction include dimethylformamide (DMF), dimethylacetamide (DMAC) and tetrahydrofuran (THF), preferably DMF and DMAC. This reaction may be also performed in a solution with pH of 8 or more (sodium bicarbonate buffer).

The amount of SMA dissolved in 15 ml of DMF is not particularly limited but, for example, 0.05 g to 1.5 g, preferably 200 to 300 mg. The reaction temperature is not particularly limited but, for example, 10 to 60° C., preferably 20 to 50° C. The reaction time is not particularly limited but, for example, 5 to 64 hours, preferably 10 to 24 hours.

As required, a catalyst may be used in the above reaction. For example, 0.5 ml of triethylamine (TEA) may be added to the reaction liquid as a catalyst to promote the reaction under stirring.

After the completion of the reaction, the reaction liquid may be filtered, dialyzed and/or concentrated according to the conventional methods to remove unreacted cysteine, unreacted SMA, degradates and other salts, and then dried as required to obtain a thiolated SMA.

The thiolated SMA may be prepared by similar reactions with other thiolating agents.

(4) Aminated SMA

Aminated SMA derivative (aminated SMA) may be prepared by reacting SMA with an aminating agent. Examples of the aminating agent include diaminoalkyl (for example, diaminoethane), guanidylbutylamine and L-lysine, preferably diaminoethane, diaminopropanol and diaminopropane.

For example, aminated SMA may be prepared by reacting SMA with an aminating agent in an organic solvent such as dimethylformamide, tetrahydrofuran, dimethyl sulfoxide in a similar manner to the above reaction for thiolating SMA.

When the amidating agent is L-lysine, guanidylated SMA with stronger basicity may be obtained. When L-arginine is used instead of L-lysine, guanidylated SMA with further stronger basicity may be obtained.

(5) Tris-SMA

SMA derivatives modified by tris(hydroxymethyl)aminomethane (hereinafter, referred to as "tris"; Tris-SMA) may be prepared by reacting SMA with a tris reagent. Examples of the tris agent include tris(hydroxymethyl)aminomethane (for example, manufactured by Wako Pure Chemical Industries). In the reaction in an aqueous solution, tris(hydroxymethyl)aminomethane chloride may be also used, while tris (hydroxymethyl)aminomethane is preferred.

For example, tris-SMA may be prepared by adding tris to a solution of SMA dissolved in dimethylformamide (DMF) and then reacting with the maleic anhydride residues.

For the complete reaction of SMA with tris, the amount of tris used in the above reaction is the equivalent amount or more, for example, 5 to 100 equivalents, preferably 5 to 10 equivalents based on the maleic anhydride residues.

The above reaction may be performed in an organic solvent system or in an aqueous solution system.

Generally, a certain amount of SMA is dissolved in an organic solvent to obtain a solution. Then, to the solution are added a certain amount of tris powders and the mixture is reacted under stirring. Preferred examples of the organic solvents used in this reaction include dimethylformamide (DMF). To 25 ml of DMF placed in a 200 ml beaker is added 0.1 to 3 g, more preferably 0.2 g to 0.6 g of SMA including maleic anhydride residues is added under stirring and dissolved. The concentration of the SMA solution is not particularly limited. For example, 0.5 g of SMA is added to DMF to be 2% W/V. Preferred amount of SMA to be added to DMF is 0.5 g (2 mmol). To the obtained solution is added 0.05 g to 10 g of tris and then reacted. When 50% of the maleic anhydride residues are to be modified by tris, the amount of tris to be added is 0.13 g (1 mmol). For example, the reaction is performed at room temperature without limitation for 10 to 30 hours, preferably 20 hours. The color of the reaction solution is at first dark yellow to orange, and then turns pale yellow. For the more complete modification of the maleic anhydride residues with tris, tris is needed to be added in an amount of about 0.3 g or more, preferably of 0.5 g to 1 g or more.

After the completion of the reaction, the reaction product is precipitated by adjusting pH to an acidic level (<pH 4) according to the above procedure, and separated. The product is further filtrated, dialyzed, and concentrated, and further subjected to fractional precipitation for removing unreacted tris, unreacted SMA, degradates, and other salts. The obtained product may be lyophilized as required to obtain tris-SMA.

Tris-SMA may be prepared according to the similar procedure with other tris agents.

(6) Aminolevulinate SMA

Aminolevulinate SMA derivative (aminolevulinate SMA) may be prepared by reacting the carboxyl group in SMA with the amino group in δ-aminolevulinic acid according to known amidation reactions. For example, the reaction may be performed under similar conditions to those employed in the preparation of aminated SMA as mentioned above in (4).

The SMA derivative of the present invention has a reduced surface charge (zeta potential). The zeta potential of the SMA surface before derivatization is generally −48 mV to −50 mV, while the zeta potential of the SMA derivative and the conjugate of the present invention is generally −40 mV to −5 mV, preferably −30 mV to −5 mV.

The zeta potential of the SMA derivative within the above range provides suppressed non-specific adsorption of the SMA derivative in the liver and/or the spleen and high concentration in tumors due to the enhanced EPR effect.

The zeta potential of the SMA derivative of the present invention within the above ranges may allow the zeta potential of the conjugate of the present invention described below to fall within the above ranges.

The zeta potential herein refers to a value measured for a solution dissolving of a sample at a concentration of 3 to 10 mg in 0.15 M NaCl (pH 7.4) with the use of a zeta potential measurement device (Phortal Model ELSZ-2, manufactured by Otsuka Electronics Co. Ltd).

Therefore, the SMA derivative of the present invention has a reduced surface potential, and is positively charged at neutral pH. It enables the preparation of a conjugate comprising a SMA chain with a wide range of charge, i.e., weakly negative to neutral to positive.

Further, the surface charge of tris-SMA is more neutral due to the impartment of great hydrophilicity to the side chain (b) in the SMA polymer, the blockade of the COOH group and the addition of the amine component. Consequently, the incorporation of (micellar) SMA into the liver and/or the spleen may be suppressed.

The SMA derivative of the present invention may be conjugated to other modifier than the above modifiers, including amino acids such as D-/L-amino acids, taurine, ornithine, citrulline; carbohydrate chains composed of glucosamine, mannose, mannitol, glucuronic acid and the like; dimaleimide methane; glutaraldehyde; organic acids such as diaminocaproic acid, citric acid, sinapinic acid and fatty acids; and other known cross-linking agents. These modifiers and cross-linking agents may be bound to the SMA derivative of the present invention according to known conventional methods.

For example, when a carbohydrate chain such as glucosamine is added to the SMA polymer as an additional modifier, the SMA may be enhanced with hydrophilicity.

The present invention also provides a conjugate comprising said SMA derivative and an active substance covalently bound to the SMA derivative directly or indirectly.

In the conjugate the present invention, the active substance may be conjugated to the SMA derivative at a moiety in the side chain (b), or a moiety different from the side chain (b) such as the maleic anhydride residue in SMA. For example, when the active substance contains an $NH_2$ group, it may be covalently conjugated to the SMA derivative via amide bond formed by reacting the $NH_2$ group with maleic anhydride residue remaining in the SMA derivative.

The conjugate of the present invention preferably includes above SMA derivative, and an active substance covalently bound directly or indirectly to at least one functional group (a) in the side chain (b) or moiety different from the side chain (b) in the SMA derivative.

Further the above SMA derivative may include at least two functional groups (a) (for example, an amino group and a SH group).

The bond between the SMA derivative and the active substance in the conjugate of the present invention is preferably selected from an amide bond, a hydrazone bond, an ester bond and a disulfide bond.

The active substance may be covalently linked to the SMA derivative directly when the active substance includes a group capable of forming a covalent bond with the functional group (a) in the side chain (b) and a different moiety from the side chain (b) in the SMA derivative (such as the maleic anhydride residue). However, when the active substance does not include a group capable of forming the above covalent bond, or when it is required, the active substance may be indirectly bound to the SMA derivative via a linking group.

The bond between the functional group (a) in the side chain (b) in the SMA derivative, and the active substance in the conjugate of the present invention may be therefore a bond via a linking group represented by the following formula [B]:

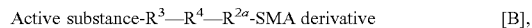

Active substance-$R^3$—$R^4$—$R^{2a}$-SMA derivative    [B], wherein $R^3$ is a group selected from —NH—, —O—, a carbonyl group, an alkylene group and a combination thereof;

$R^4$ is a group selected from —C(CH$_3$)=N— and —C(benzyl)=N—; and $R^{2a}$ is —NH—.

In the above formula [B], $R^{2a}$ is a residue derived from the hydrazide group, which is a functional group (a) in the SMA derivative.

When the functional group (a) in the side chain (b) in the above SMA derivative is a hydrazide group and the moiety used for forming the linking group is —R³—C(CH₃/benzyl)
=O, the bond between the SMA derivative and the active substance via a linking group is formed, for example, as follows:

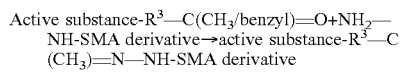
NH-SMA derivative→active substance-R³—C
(CH₃)=N—NH-SMA derivative

The linking group —R³—R⁴— in the above formula [B] is preferably a group selected from the followings:
(1)   —NH—(CH₂)₂—NH—C(=O)—(CH₂)₂—C(CH₃) =N— (for example, a group derived from BOC-ethylene diamine and levulinic acid); and
(2) —NH—CH₂—C(=O)—(CH₂)₂—C(benzyl)=N— (for example, a group derived from aminolevulinic acid benzyl ester).

The "active substance" herein is a substance with an activity such as physiological activity (drug efficacy) without particular limitation. Examples of the active substances include drugs such as anticancer agents, peptide hormones, antibiotics and anti-inflammatory agents, preferably anticancer agents, antibiotics and peptide hormones, more preferably anticancer agents.

Examples of the above anticancer agent include pirarubicin, protoporphyrin, zinc portophyrin, boronomercaptate, boronocysteine (in case of treating cancers with boron derivatives, radiation of thermal neutron is required), epirubicin, aclarubicin, doxorubicin, preferably, zinc protoporphyrin, boronomercaptate, boronocysteine and epirubicin.

Examples of the above antibiotic include streptomycin, amikacin, aminodibenzyl penicillin and vancomycin.

Examples of the above peptide hormone include calcitonin, endorphin, enkephalin, prolactin, lactogenic hormone, parathyroid hormone, prolactin releasing hormone, insulin and adrenocorticotropic hormone (ACTH).

The conjugate of the present invention may be prepared by reacting at least one functional group (a) in the side chain (b) in the SMA derivative with a functional group in the active substance and thereby binding the active substance to the SMA derivative covalently.

The conjugates of the present invention include those with active substances bound to the SMA derivative via amide bond formed by reacting a different moiety from the functional group (a) (for example, the maleic anhydride residue) in the SMA derivative with the functional group in the active substance (for example, amino group).

The process for preparing (1) SMA-hydrazone-THP, (2) SMA-hydrazone-levulinyl-ZnPP, (3) SMA-S—S-active substance and (4) SMA-THP/-tris are illustrated below as examples of the conjugation of the present invention.

(1) SMA-Hydrazone-THP

When the SMA derivative is the hydrazinated SMA and the drug is pirarubicin (THP), the hydrazide residue in the hydrazinated SMA [3] is reacted with the circled part in the carbonyl group in the THP molecule [4] to form the conjugate [4'] comprising THP added to the SMA chain like a Schiff base as shown in the below reaction scheme:

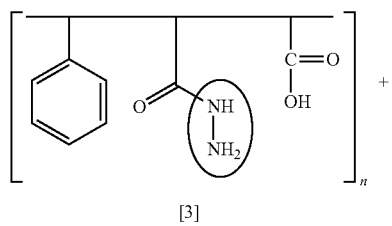

[3]

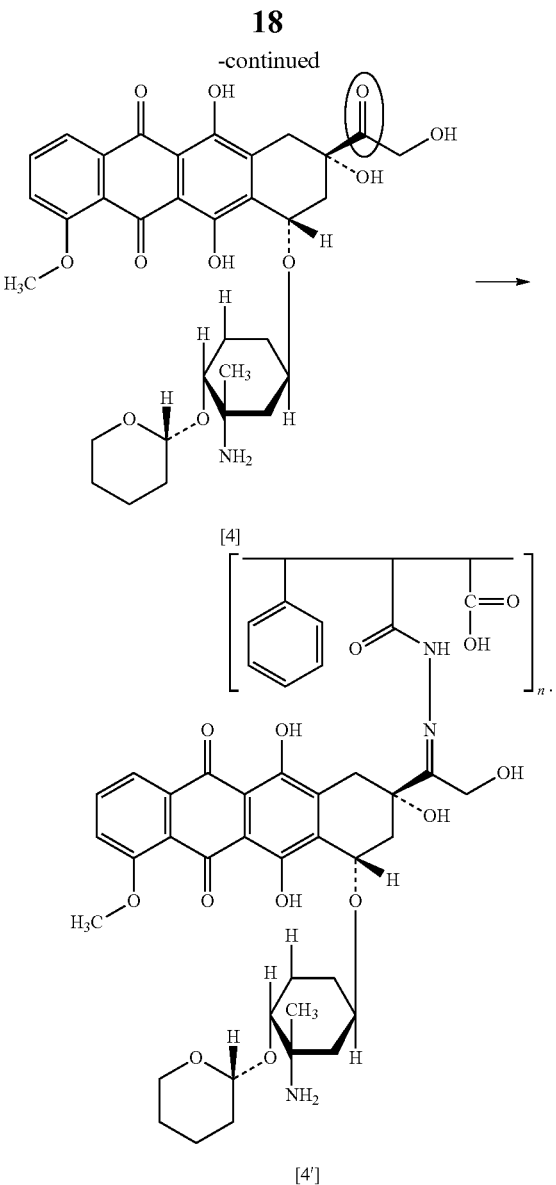

The above reaction is preferably performed in, but not particularly limited to, methanol. The reaction may be performed in a solvent such as DMF, tetrahydrofuran, dimethylformamide and water. This reaction may be performed at to 70° C., preferably at 15 to 37° C., under ultrasound radiation for promoting the reaction, as required. Performing this reaction under stirring for 1 to 50 hours, preferably for 10 to 20 hours may result in the desired product.

The ratio of the hydrazide group [3]:THP [4] in the production of the above conjugate [4'] may be 1 mol:0.2 mol, while the addition of an excessive amount of [4] relative to [3] may increase the loading of THP in the reaction product (SMA-THP). The amount of the hydrazine group is preferably 20 to 50% relative to SMA, which may provide low percentage of hydrazination of SMA and thereby maintain the sufficient solubility. Further, the addition of THP in an amount of 50 to 100% relative to the introduced hydrazine may provide SMA-hydrazone-THP containing 20% or more of THP.

(2) Preparation of SMA-Hydrazone-Levulinyl ZnPP

When the SMA derivative is hydrazinated SMA, and the drug is zinc protoporphyrin (ZnPP), the hydrazinated SMA may be bound to ZnPP via a linking group. In this case, SMA-hydrazon-levulinyl-ZnPP [12] may be obtained, for example, through synthesis of diaminated derivatives [7] of protoporphyrin (PP) [5], synthesis of the levulinate derivative [9] thereof, introduction of zinc ([10]→[11]) and binding of ZnPP to the hydrazinated SMA.
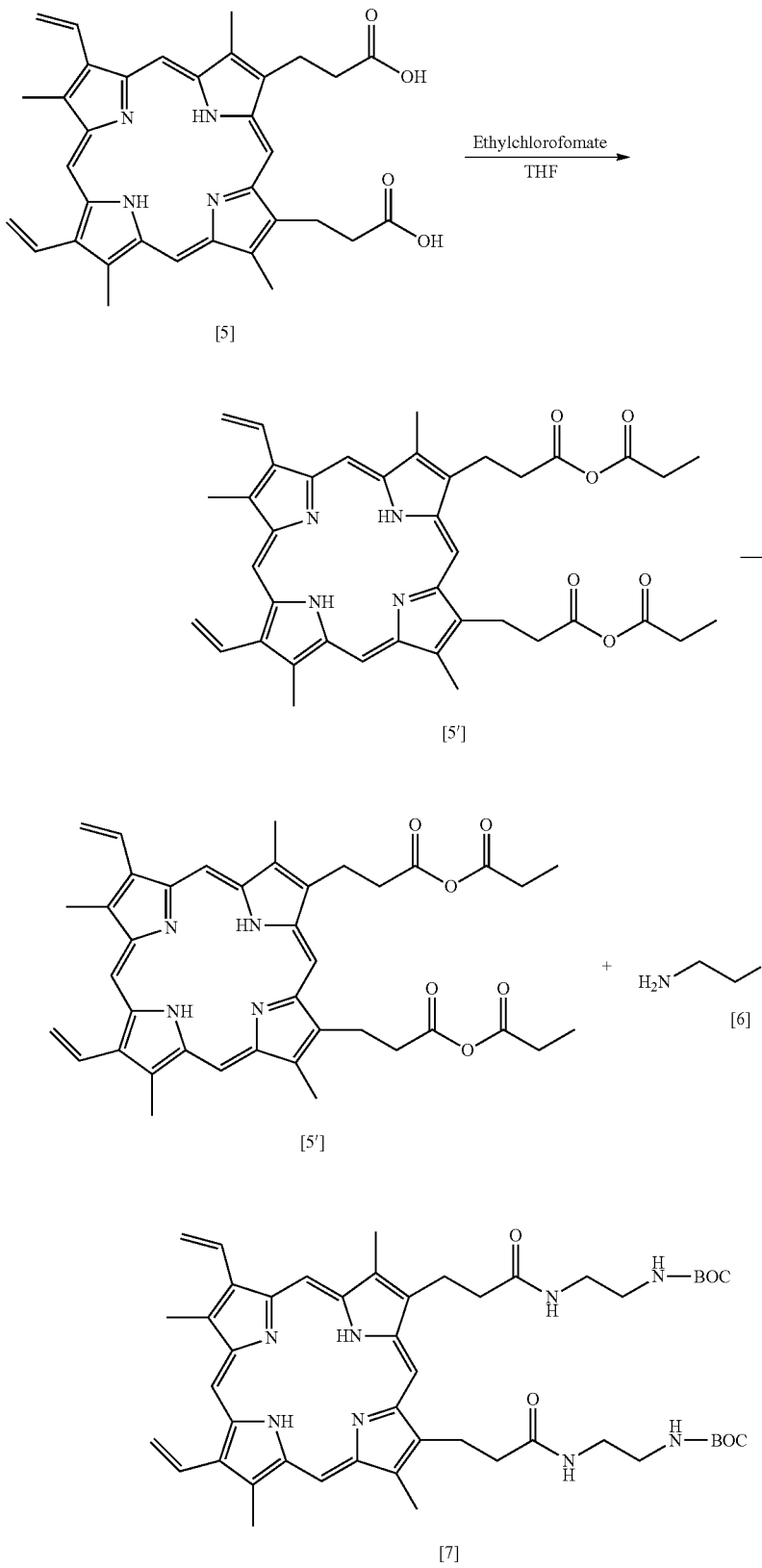

-continued
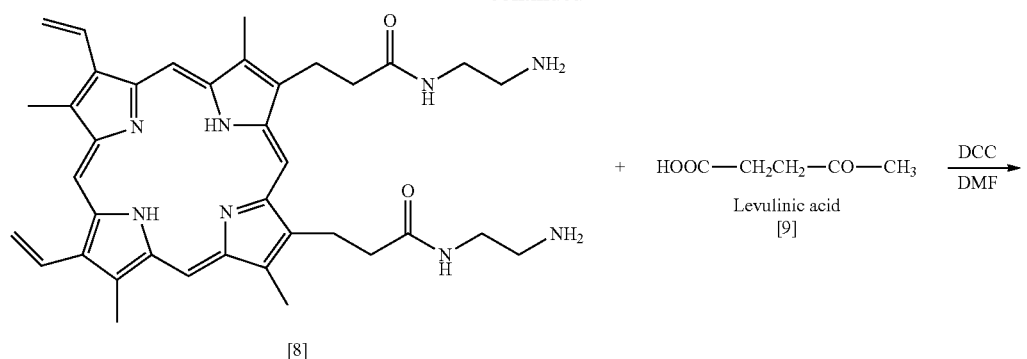
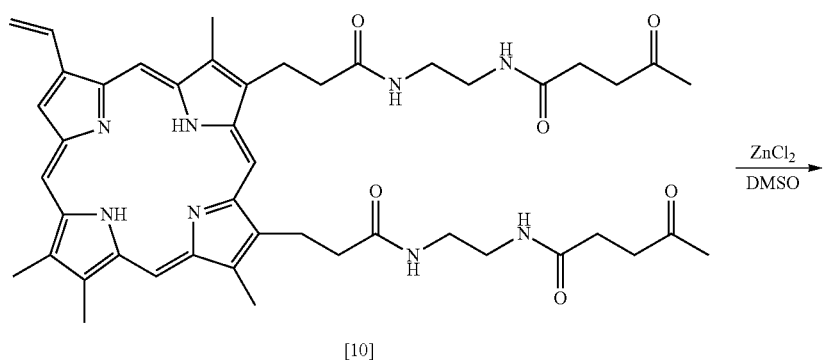
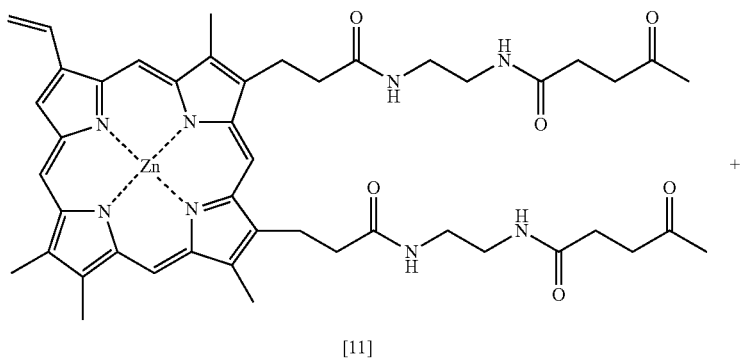
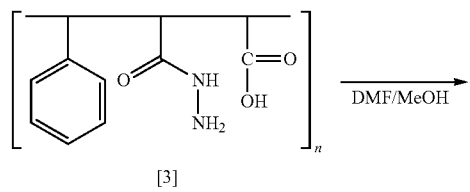

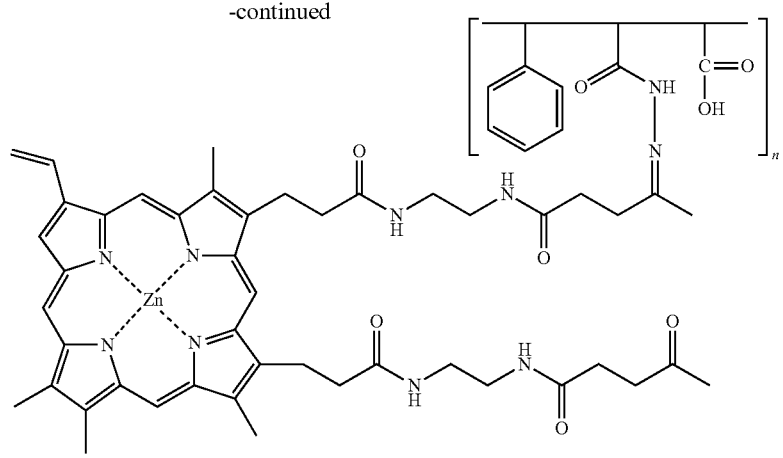

[12]

At the first step in the above reaction, two carboxyl groups in the protoporphyrin (PP) are active-esterified to obtain chloroformate of PP [5']. For example, to 100 mg of protoporphyrin placed in a 100 mL egg-plant shaped flask covered with aluminum foil is added 20 ml of tetrahydrofuran (THF) and then suspended to dissolve. To the PP/THF suspension, about 10 mole excess equivalents of triethylamine (0.25 mL, 1.79 mmol) is added dropwise under stirring. To the reaction solution of PP and triethylamine, 0.34 ml (3.56 mmol) of ethyl chloroformate precooled at 0° C. was added slowly over about 10 minutes and the mixture is reacted under stirring for 20 hours on ice and then for 10 minutes at room temperature (25° C.)

A catalyst such as triethylamine may be added as required. The amount of BOC ethylenediamine to be added is 1.5 to 3 times excess relative to the amount of carboxyl groups in protoprphyrin. The amount of ethylenediamine to be added is 10 to 100 times relative to the amount of carboxyl groups in protoporphyrin. This reaction is performed at room temperature for 30 to 60 minutes.

At the second step, a carboxyl group in the levulinic acid [9] is added to the amino group in the ethylenediamine introduced into PPED [8]. For performing this reaction, PPED is dissolved in DMF, and 2 to 20 mole equivalents excess of levulinic acid and DCC as a catalyst are added to the solution to react at 25 to 50° C. for 6 to 24 hours.

Subsequently, at the third step, SMA-hydrazide [3] is reacted with the ketone group of the levulinic acid added to the PP via a reaction for forming a bond like Schiff base. In this reaction, SMA hydrazide is dissolved in a solvent such as DMF and DMSO, and then 2 to 20 mole equivalents of levulinyl PPED [10] and a catalytic amount of acetic acid or trifluoroacetic acid are added to the solution. The reaction is performed at room temperature to 40° C. for 12 to 24 hours.

Another method for adding levulinic acid to PP comprises employing an aminolevulinic acid ester and reacting the amino group with a carboxyl group in PP (see the reaction formula below). The formula represents the synthesis reaction of protoporphyrin (PP) levulinate with the use of aminolevulininc acid benzyl ester (aminorevulinate Cbz) [13]. This reaction may be performed according to conventional procedures in a solvent such as dimethylformamide (DMF) with the use of EDAC as a condensation agent. Aceto acetate and butoxyethanol may be used instead of levulinic acid. This reaction proceeds as shown in the following scheme:

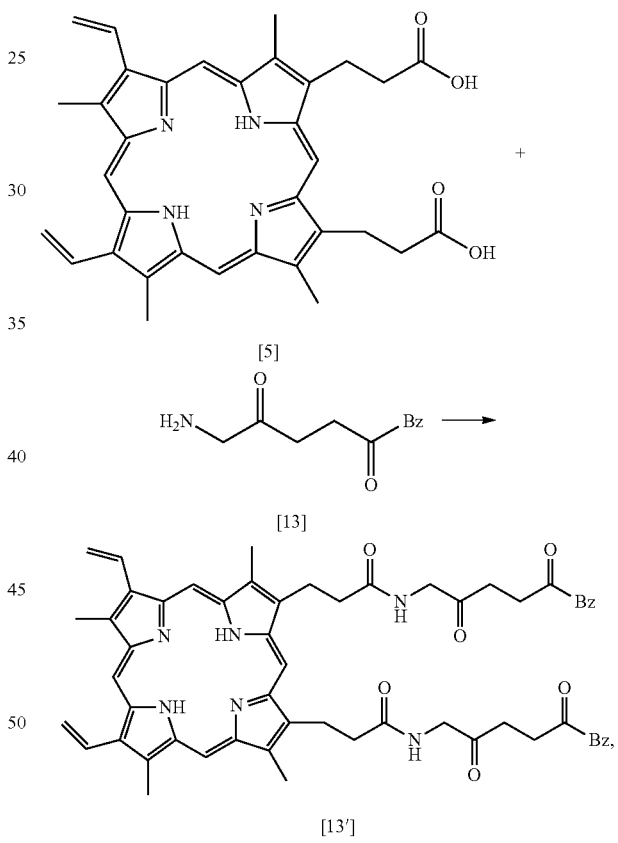

wherein Bz is a benzyl group.

The protoporphyrin (PP) levulinate [13'] synthesized from an aminolevulinic acid benzyl ester (aminolevulinate Cbz) [13] may be bound to a hydrazinated SMA in a similar manner to the binding of a PP levulinate and a hydrazinated SMA.

The use of SMA-hydrazone/tris instead of SMA-hydrazine may provide SMA-hydrazone-levulinyl-ZnPP/tris (see the formula [18'] below).

(3) SMA-S—S-Active Substance

It is generally known that in an aqueous solution, a protein including a SH group and a SH compound (R) perform oxidative S—S bond formation as represented by the following reaction formula A:

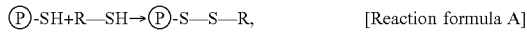
(P)-SH+R—SH→(P)-S—S—R,    [Reaction formula A]

wherein (P) represents a protein, a peptide and a SMA polymer comprising a —SH group.

provided that this reaction is required to be performed under oxygen partial pressure at or near atmospheric pressure, at weak alkaline pH, at 0 to 40° C., particularly 4 to 5° C., for several to several ten hours. A catalyst such as copper sulfate is conveniently added in a concentration of several mmols/L, as required.

The SMA derivative (SMA-SH) introduced with a SH group into SMA may form a S—S bond between the SH group and a borono thiol compound (boronomercaptate, $Na_2B_{12}H_{11}SH$, abbreviated as "BSH") or boronocysteine (BCySH) via air oxidation in an aqueous solution. It may provide a macromolecule bound conjugate represented by SMA-S—S-drug.

As an example, the formation of the S—S bond between the mercapto SMA described in FIG. 1 and boronomercaptate ($Na_2B_{12}H_{11}S_{11}$) as an active substance is illustrated in the following Reaction formula B:

[Reaction formula B]
SMA—SH  +  BSH  →  SMA—S—S—B,
  [14]        [15]           [16]

wherein B is boronomercaptate, a cage shaped compound comprising 12 boron atoms.

The above —S—S— forming reaction may be used to add boronocysteine and other thiol compounds (R—SH) to the SMA chain as a pendant group via —S—S— bond as described below (see the reaction formula C).

This reaction proceeds in a similar manner to the above reaction formula [A].

[Reaction Formula C]

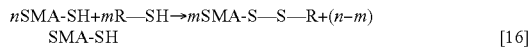
nSMA-SH+mR—SH→mSMA-S—S—R+(n−m) SMA-SH  [16]

wherein R is an active substance; m is the mole number. In the case of the molecular weight of the SMA is about 1200, SMA contains 1 to 6 moles of SH groups and n represents the mole equivalent of the polymerization degree of styrene-maleic acid (n>m).

The SMA-S—S—R obtained by the above reaction behaves as a nanomedicine, shows EPR effect and accumulates efficiently in tumor sites several hours after the intravenous injection. Upon radiating thermal neutrons, alpha ray/Li nuclears are generated from the boron atoms [16] accumulated to the tumor sites due to the EPR effect, and thus exhibit tumor specific cytocidal effects. It is advantageous because the thermal neutrons do not exhibit cytocidal effects (side effects) in normal tissues without the accumulation of boron atoms. The B containing micelles therefore accumulate in a tumor specific manner and thus show desired antitumor effects.

Further, boron atoms may be introduced as a pendant group by reacting the amino group in boronophenylalanine directly with the maleic anhydride residue instead of the reaction using SMA-SH.

The following formula represents the above reaction of SMA-SH and boronomercaptate (BSH) as boronocysteine.

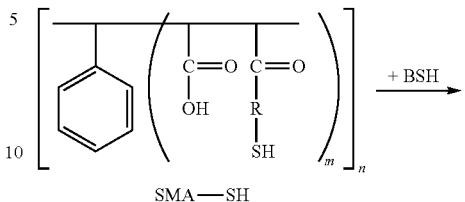

SMA—SH

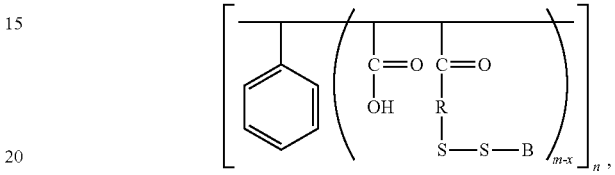

wherein B is boronomercaptate; n>m; and m–x is the number of substitutions.

In the synthesis of SMA-SH, SMA-SH may form SMA-S—S-SMA via the intramolecular cross-linking. The by-products are likely to be insoluble and thus, if necessary, a reducing agent such as sodium borohydride is added at a concentration of about 1 mM (about 30 to 300 mg of powders are added to 1 l of the reaction liquid) and stirred under blocking air with $N_2$ to obtain more purified SMA-SH before starting the reaction represented by [the reaction formula B].

(4) SMA-THP/-Tris

The tris-SMA synthesized above, containing about 50% of maleic anhydride residues is reacted with THP in the presence of a condensing agent such as DCC (dicyclohexylcarbodiimide) and WSCI (water-soluble carbodiimide; for example, EDAC (ethyldimethylaminopropylcarbodiimide)) and a catalyst such as triethylamine to directly form a amide bond between free amino group in THP and maleic anhydride residue, or form an amide bond between COOH in the ring-opened maleic acid and amino group in THP and thereby synthesize SMA-tris-THP conjugate.

The details of the reaction are described as follows. It is noted that the amounts of the respective reagents used are described as an example. About 300 mg of the above tris-SMA (about 0.6 mmol as maleic anhydride residues) is dissolved in 15 ml of DMF. To the solution is added 100 mg of THP (about 0.16 mmol; described above; manufactured by Mercian Corporation KK; MW: 627.64) and the mixture is stirred for 2 hours at room temperature. Then, 0.5 ml of triethylamine (described above) is added and stirred for 17 hours at room temperature. After the completion of the reaction, 1 to 3 times volume of distilled water is added and the obtained product is concentrated and dialyzed with a device for concentration/dialysis with a molecular sieve membrane (Cut off MW: 2000), for example, a Lab. Scale device from Amicon. Distilled water is further added, and dialysis is repeated 2 to 4 times to remove the unreacted substances, reaction degradation products, and then the THP-SMA conjugates of macromolecules synthesized from low molecules. The product is lyophilized to obtain SMA-THP/-tris. The yield efficiency is about 80% based on THP.

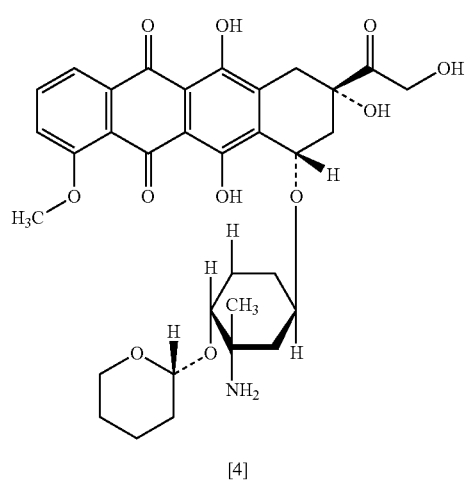

[4]

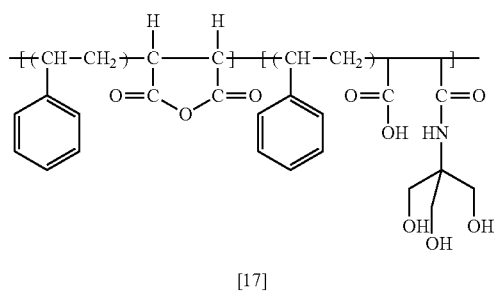

[17]

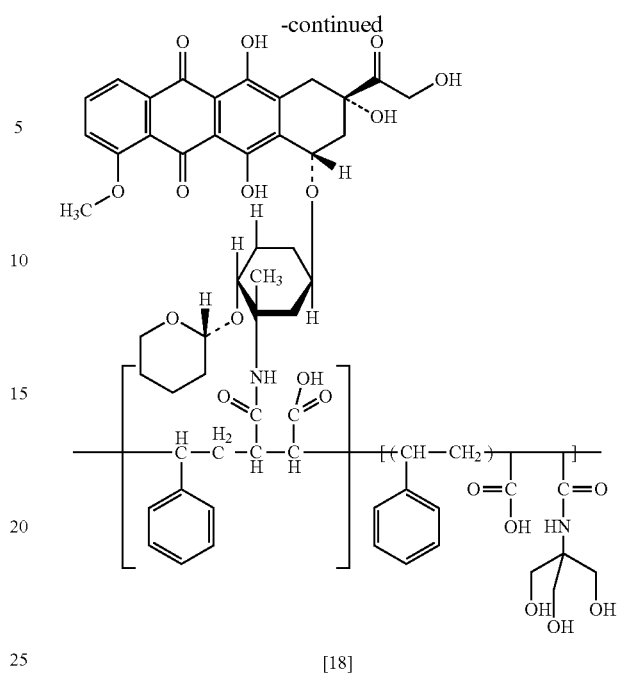

[18]

When the above reaction is performed with SMA-tris-hydrazine and THP, another type of SMA-THP conjugate may be obtained. In this case, SMA is bound to THP via hydrazone bond instead of the amide bond in the conjugate [18] in the above scheme. The product [18'] resembles the compound [4'] but comprises SMA-hydrazine and SMA-tris in the backbone and comprises THP bound to the hydrazine chain (b) as a pendant group instead of via amide bond.

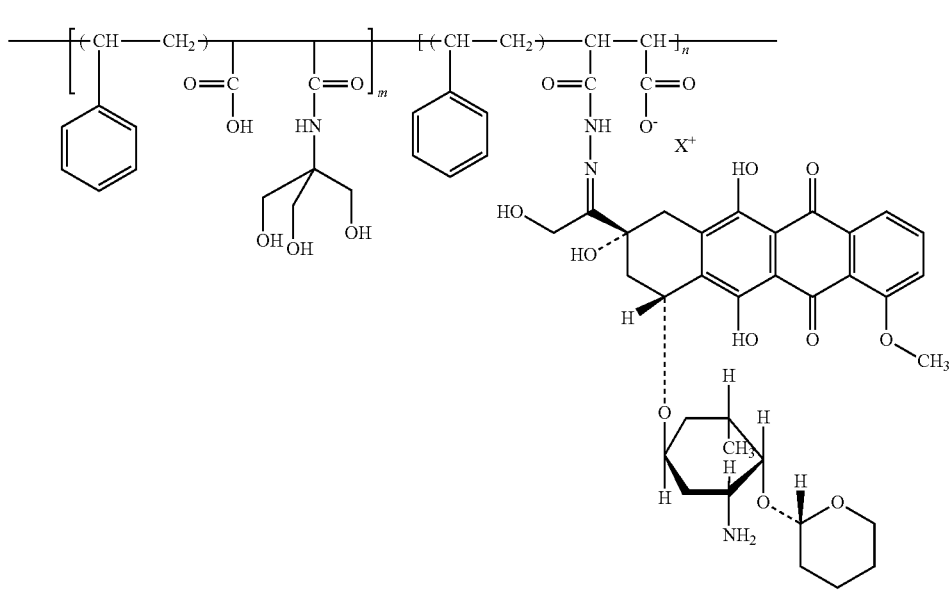

[18']

The conjugate of the present invention has many advantages over the conventional SMA-active substance complex or conjugate.

For example, the conjugate comprising the active substance (drug) conjugated to SMA via hydrazone bond (SMA-hydrazone-drug conjugate) may release the drug at low pH regions such as tumor tissues, because the chemical hydrazone bond is easily cleaved at low pH regions such as tumor tissues (see FIG. 2). The released drug thus may diffuse more freely in vivo and bind to target cells and/or intracellular target molecules. In the meantime, the conjugate behaves as a macromolecular under neutral pH regions such as normal tissues and blood, because the hydrazone bond is not cleaved under such conditions. Consequently, the distribution of the drug in normal tissues without EPR effect is suppressed, and thus the reaction of the drug (side effect) is suppressed in normal tissues where the drug is not accessible. Accordingly the conjugate has advantages in drug efficacy specific to local tumors by EPR effect and secondly by the hydrazone bond being cleaved specifically at acidic pH particular to tumors, and consequently provides reduced adverse effects.

In addition to the tumor-specific accumulation due to the EPR effect, the conjugate comprising the active substance (drug) conjugated to SMA via disulfide bond (SMA-S—S-drug conjugate) releases the drug through the reduction of the S—S bond when incorporated into cells because the intracellular concentration of glutathione is generally as high as 1 mM. Therefore the SMA-S—S—R conjugate does not liberate the active low molecule drug-SH outside of cells. When incorporated into cells, S—S bond is cleaved and drug-SH (active low molecule) is generated, and the drug efficacy is exhibited according to the following reaction formula:

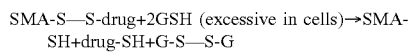

SMA-S—S-drug+2GSH (excessive in cells)→SMA-SH+drug-SH+G-S—S-G

The conjugate of the present invention may have micellar structure in suspension such as blood. When the conjugate of the present invention forms a micelle, the apparent molecular weight in an aqueous solution is higher than that calculated based on the chemical structure formula. For example, the conjugate with molecular weight of 50,000 or more is advantageous in enhancing the tumor selectivity (selective delivery) due to the EPR effect and increasing the drug efficacy.

The conjugate of the present invention can release the active substance in vivo and thus exert various bioactivities based on the active substances. Therefore, when the active substance is a drug, the conjugate may be used as a medicament based on the bioactivity of the drug.

The conjugate of the present invention may suppress the release of the active substance in blood as observed in the previous SMA-active substance complexes and the conjugates, thereby reduces the accumulation of active substances in the liver and/or the spleen by reducing the negative charge on the surface. Thus the conjugate of the present invention solves the above problems and further accomplishes the high concentration in tumors due to the enhanced EPR effect. The conjugate may be thus used very advantageously as a carcinostatic agent, namely in preventing or treating cancers, inhibiting the growth of cancers, suppressing the metastasis of cancers, and/or promoting apoptosis, when the active substance in the conjugate of the present invention is an antitumor agent.

Therefore, the present invention provides a medicament, especially a carcinostatic agent, comprising the conjugate of the present invention.

The conjugate of the present invention may be safely administered to mammals (for example, mice, rats, hamsters, rabbits, cats, dogs, cattle, sheep, monkeys and human) and may be used for preventing or treating various diseases, especially cancers based on the physiological activities of the active substance (drug, especially antitumor agent) used in the conjugate.

Therefore the present invention provides a method for treating or preventing various diseases, especially cancers, comprising administering the conjugate of the present invention to a patient.

The conjugate of the present invention may be administered orally or parenterally to a mammal in combination with a pharmaceutically acceptable carrier as a pharmaceutical composition. When the conjugate of the present invention is administered orally, the examples of the dosage forms include tablets (such as sugar coated tablets, sublingual tablets, and buccal tablets), oily agents (oily preparations), pills, granules, powders, capsules, syrup, emulsions, suspensions, patches for oral mucosa. When the conjugate of the present invention is administered parenterally, the examples of the dosage forms include injections (such as intravenous injections, arterial injections, subcutaneous injections, intradermal injections, intramuscular injections, arterial injections (including oily injections)), infusates, infusions, and depot preparations.

The present invention therefore provides a pharmaceutical composition comprising the conjugate of the present invention and a pharmaceutically acceptable carrier.

The conjugate of the present invention may be prepared in the above dosage forms with appropriate amounts of the additives conventionally used in the pharmaceutical field, such as excipients, binders, disingetrants, lubricants, sweeteners, surfactants, suspending agents, emulsifiers according to known methods conventionally used for preparing the dosage forms, for example, those disclosed in Japanese pharmacopeia.

For example, when the conjugate of the present invention is formulated into injection solutions, the conjugate is dissolved in sterilized aqueous solutions and oily (oil-dissolving) liquid as a pharmaceutically acceptable carrier, suspended and emulsified to obtain aqueous preparations and oily preparations respectively. Oily preparations including preparations for oral administration and enteral depot preparations may be prepared in a similar manner.

Further, the conjugate of the present invention may be formulated as tablets, pills, and granules by the use of excipients, binders, disintegrants and lubricants. The conjugate of the present invention may be formulated as syrup with the use of sweeteners. The conjugate of the present invention may be formulated as emulsions, suspensions, or suspending agents with the use of surfactants and emulsifiers.

Examples of the aqueous solution include saline, isotonic solutions comprising auxiliary agents such as glucose. Solubilizers such as alcohol (including ethanol), polyalcohol (including propylene glycol and polyethylene glycol) and non-ionic surfactants (for example, polysorbate 80 and HCO-50) may be added to the solutions.

Examples of the oily liquid include sesame oil, soybean oil, medium-chain fatty acids, and lipiodol. Solubilizers such as benzyl benzoate and benzyl alcohol may be added to the liquids.

Buffers (such as phosphate buffer and sodium acetate buffer), analgesics (such as benzalkonium chloride and procaine hydrochloride), stabilizers (such as human serum albumin, and polyethylene glycol), preserving agents (such as benzyl alcohol and phenol) may be further blended.

Further, other additives conventionally used in the pharmaceutical field may be added as required.

Examples of the excipient include water, the above aqueous solutions, the above oily liquids, lactose, white soft sugar, glucose, starch, sucrose, microcrystalline cellulose, powdered Glycyrrhiza, mannitol, sodium bicarbonate, calcium phosphate and calcium sulfate.

Examples of the binder include starch paste, arabic gum, gelatin, tragacanth, caboxymethylcellulose, sodium alginate and glycerin.

Examples of the disintegrant include starch and calcium carbonate.

Examples of the lubricant include magnesium stearate, stearic acid, calcium stearate and talc.

Examples of the sweetener include glucose, fructose, invert sugar, sorbitol, xylitol, glycerin, simple syrup and saccharin.

The present invention therefore provides the use of the conjugate of the present invention for manufacturing a pharmaceutical composition.

While the content of the conjugate of the present invention in the above pharmaceutical composition varies depending on the types of drugs suitable for the conjugate and the dosage forms, the content is generally about 0.01 to 99 wt %, preferably about 3.0 to 60 wt % based on the total weight of the pharmaceutical composition.

The dosage of the conjugate of the present invention depends on the condition and weight of the patient, the type of the drug used in the conjugate, the administration route and the like. For example, when the conjugate is administered for treating cancers in the form of an injection, the single dose is conveniently about 1.0 to 60 mg, preferably about 2.0 to 50 mg per kg of body weight as the active ingredient, for example, in the form of an injection for intravenous administration or administration as an infusion. When the conjugate is polymerized, the dose may be 100 mg to 10 g or more. The doses do not always need to be daily administered, but may be administrated, for example, once per 1 to 3 weeks.

EXAMPLES

The invention is further described in detail by reference to the following experimental examples.

(Example 1) Synthesis of Hydrazinated SMA (SMA/Hydrazine Ratio=1

To 20 ml of distilled water, 0.13 ml of hydrazine monohydrate ($H_2N-NH_2.H_2O$; MW=50.06; Wako Pure Chemical Industries, Osaka; 2.6 mmol as $NH_2-NH_2$) and then 263 mg of SMA (300 mg as maleic anhydride; manufactured by Sartomer, Exton, Pa., USA; trade name: SMA-Base Resin SMA1000; average molecular weight: 1000 to 1500; 1.3 mmole equivalents as maleic anhydride residues in total) were added, and the mixture was stirred to react at room temperature for 5 to 40 hours, preferably for 24 hours with a magnetic stirrer. The reaction mixture was cloudy immediately after the addition of SMA and became clear after several hours, and the pH was about 9.0. After the reaction for hours, the reaction liquid was filtered through a glass filter. Then 100 ml of distilled water was added and stirred to dilute and dissolve. Subsequently, the filtrate was warmed to to 40° C. in a rotary evaporator, dried under reduced pressure, and concentrated to ¼ volume. The obtained product was diluted in 200 ml of distilled water to obtain an aqueous solution. The solution was dialyzed through a molecular sieve membrane with cut off MW of 1000 for 1 to 2 days and concentrated repeatedly to ⅕ volume with an Amicon Lab. Scale device. Unreacted hydrazine, unreacted substances, degradates and other salts were removed and the product was lyophilized to obtain about 212 mg of white to slightly yellow powders. Table 1 shows the results of the elementary analysis.

(Example 2) Synthesis of Hyrazidated SMA (SMA/Hydrazine=1/2): Reaction of Maleic Anhydride Residues with 2 Mole Equivalents Excess to Hydrazine in Water [Anhydride Ring:Hydrazine=1:2 (Mole Ratio)]

To 20 ml of water, 127 μl of hydrazine monohydrate (Wako Pure Chemical Industries, Osaka; 2.61 mmol as $NH_2NH_2$) was added and mixed. To the mixture was added 300 mg of SMA-maleic anhydride copolymer powders (1.3 mmole equivalents as maleic anhydride) and stirred with a magnetic stirrer for 23 hours at room temperature. Separately, 3 batches of similar reactions were carried out with 300 mg of SMA-maleic anhydride copolymer powders (1.3 mmole equivalents as maleic anhydride) and 127 μl of hydrazine monohydrate (2.61 mmol as $NH_2NH_2$). After the reaction for 23 hours, each product was filtered (through a glass filter N05B) and concentrated in a rotary evaporater. Subsequently, 4 batches of the products were combined and then diluted with distilled water, dialyzed through a dialysis membrane with a molecular weight cut-off of 1000 [Manufactured by Spectrum Laboratories] (the procedure was repeated 2 to 3 times) and lyophilized to obtain white powders (about 676.9 mg). Table 1 shows the result of elemental analyses.

(Examples 3 to 6) Synthesis of Hydrazinated SMA

A hydrazinated SMA was prepared in a similar reaction to that of Example 2 except that hydrazine was added in an amount of 5 equivalents (Example 3), 20 equivalents (Example 5) and 50 equivalents (Example 6) relative to the maleic anhydride residues. Consequently, SMA derivatives with all the maleic anhydride residues hydrazinated with almost the same elemental analysis values as shown in Table 1 were obtained quantitatively.

(Example 7) Synthesis of Hydrazinated SMA: Reaction of Maleic Anhydride Residues with 1/4 Mole Equivalents of Hydrazine in Water [Anhydride Ring:Hydrazine=1:1/4 (Mole Ratio)]

To 20 ml of water, 15.9 μl of hydrazine monohydrate (0.33 mmol as $NH_2NH_2$; Wako Pure Chemical Industries, Osaka) was added and mixed, and then 300 mg of SMA-maleic acid copolymer powders (1.3 mmole equivalents as maleic anhydride) were added. The mixture was stirred at room temperature for 24 hours with a magnetic stirrer. Distilled water was added to dilute the reaction liquid which maintained to be cloudy through the reaction. The crude product was dialyzed through a dialysis membrane with a molecular weight cut-off of 1000 [manufactured by Spectrum Laboratories] (the procedure was repeated 2 to 3 times)

and lyophilized to obtain white powders (about 238.3 mg). Table 1 shows the result of elemental analyses.

(Example 8) Synthesis of Hydrazinated SMA: Reaction of Maleic Anhydride Residues with 1/2 Mole Equivalents of Hydrazine in Water [Anhydride Ring:Hydrazine=1:1/2 (Mole Ratio)]

To 20 ml of water was added 32.1 µl of hydrazine monohydrate (0.66 mmol as $NH_2NH_2$; Wako Pure Chemical Industries, Osaka) and mixed. Subsequently, 300 mg of SMA-maleic anhydride copolymer powders (1.3 mmole equivalents as maleic anhydride) were added and the mixture was stirred for 24 hours at room temperature with a magnetic stirrer. Distilled water was added to the reaction liquid which maintained to be cloudy through the reaction. The crude product was dialyzed through a dialysis membrane with a molecular weight cut-off of 1000 [manufactured by Spectrum Laboratories] (the procedure was repeated 2 to 3 times) and lyophilized to obtain white powders (about 185.9 mg). Table 1 shows the result of elemental analyses.

(Example 9) Synthesis of Hydrazinated SMA: Reaction of SMA with Mole Equivalent of Hydrazine in Water [Anhydride Ring:Hydrazine=1:1 (Mole Ratio)]

To 20 ml of water, 63.7 µl of hydrazine monohydrate (1.31 mmol as $NH_2NH_2$; Wako Pure Chemical Industries, Osaka) was added and mixed. Subsequently, 300 mg of SMA-maleic anhydride copolymer powders (1.3 mmole equivalents as maleic anhydride) were added and the reaction mixture was stirred for 24 hours at room temperature with a magnetic stirrer. The reaction liquid, which maintained to be cloudy through the reaction, was diluted with distilled water. The crude product was dialyzed with a dialysis membrane with a molecular weight cut-off of 1000 [manufactured by Spectrum Laboratories] (the procedure was repeated 2 to 3 times), and lyophilized to obtain white powders (about 240.2 mg). Table 1 shows the result of elemental analyses.

As described above, the amount of hydrazine groups introduced may be increased or decreased by adjusting the amount of hydrazine. When the amount of hydrazine added is ¼, ½ and 1 equivalent based on maleic anhydride residues, the nitrogen content derived from hydrazine was decreased (Table 1).

(Example 10) Synthesis of Hydrazinated SMA: Reaction of Maleic Anhydride Residues with 2 Mole Equivalents of Hydrazine in an Organic Solvent DMF [Anhydride Ring:Hydrazine=1:2 (Mole Ratio)]

SMA-maleic anhydride 300 mg (1.31 mmol as anhydride ring) was dissolved in 15 ml of DMF. To the solution, hydrazine monohydrate (0.127 µl of $NH_2$—$NH_2$—$H_2O$; 2.6 mmol) was added and reacted under stirring for 48 hours at room temperature. Immediately after the addition of hydrazine, the reaction white cloud was generated in the reaction solution and was remained after 48 hours. The reaction liquid was concentrated in a rotary evaporator and 1 to 3 ml of 0.1 M NaOH was added to dissolve the cloud. After the additional reaction for 24 hours, the solution was concentrated to ⅓ to ¼ volume, neutralized, dialyzed through a dialysis membrane with a MW cut-off of 1000 and lyophilized. Table 1 shows the result of elemental analyses.

(Example 11) Synthesis of Hydrazinated SMA: Reaction of Maleic Anhydride Residues with 5 Mole Equivalents of Hydrazine in an Organic Solvent [Anhydride Ring:Hydrazine=1:5 (Mole Ratio)]

In a similar manner, the reaction was performed under stirring except for adding 0.318 ml (6.54 mmol) of hydrazine. Immediately after the addition, the upper part of the reaction liquid was solated and got clouded by stirring. The reaction was continued under stirring for 48 hours, and then concentrated to ⅓ to ¼ volume in an evaporator. The product was dialyzed against distilled water and then lyophilized. Table 1 shows the result of elemental analyses.

TABLE 1

| Novel SMA derivative | Reaction System | Enzyme | Example | Ratio of the Modifier Based on the Maleic Anhydride Residues (mol excess) | Form of Unreacted Maleic Anhydride Residues (a: Anhydride Ring b: Carbonate) | Elemental Analysis Values (wt %) | | | | | | Introduction Rate into SMA (%) |
|---|---|---|---|---|---|---|---|---|---|---|---|---|
| | | | | | | N | C | S | H | C/N | S/N | |
| Hydrazidated SMA Derivatives | Aqueous Solution System | — | 7 | 1/4 | a | 1.4 | 70.8 | — | 5.5 | 51.6 | — | |
| | | | | | | 1.4 | 71.6 | — | 5.5 | 52.3 | — | 11 |
| | | — | 8 | 1/2 | a | 5.7 | 67.7 | — | 5.7 | 11.8 | — | |
| | | | | | | 5.7 | 68.0 | — | 5.9 | 11.9 | — | 48 |
| | | — | 1 | 1 | a | 7.7 | 66.9 | — | 5.8 | 8.7 | — | |
| | | | | | | 7.7 | 66.3 | — | 6.0 | 8.6 | — | 66 |
| | | — | 2 | 2 | a | 11.9 | 63.1 | — | 6.2 | 5.3 | — | |
| | | | | | | 11.1 | 63.5 | — | 6.3 | 5.7 | — | 100 |
| | | — | 3 | 5 | a | 11.6 | 63.1 | — | 6.2 | 5.4 | — | |
| | | | | | | 11.1 | 63.5 | — | 6.3 | 5.7 | — | 100 |
| | | — | 4 | 10 | a | 11.9 | 63.2 | — | 6.2 | 5.3 | — | |
| | | | | | | 11.1 | 63.5 | — | 6.3 | 5.7 | — | 100 |
| | | — | 5 | 20 | a | 11.3 | 64.1 | — | 6.1 | 5.7 | — | |
| | | | | | | 11.1 | 63.5 | — | 6.3 | 5.7 | — | 100 |
| | | — | 6 | 50 | a | 11.5 | 64.3 | — | 6.2 | 5.6 | — | |
| | | | | | | 11.1 | 63.5 | — | 6.3 | 5.7 | — | 100 |
| | Organic Solvent System (DMF) | — | 10 | 2 | b | 9.8 | 58.4 | — | 6.1 | 6.0 | — | |
| | | | | | | 9.8 | 58.3 | — | 5.4 | 6.0 | — | 96 |
| | | — | 11 | 5 | b | 9.8 | 58.6 | — | 6.1 | 6.0 | — | |
| | | | | | | 9.8 | 58.3 | — | 5.4 | 5.9 | — | 95 |

TABLE 1-continued

| Novel SMA derivative | Reaction System | Enzyme | Example | Ratio of the Modifier Based on the Maleic Anhydride Residues (mol excess) | Form of Unreacted Maleic Anhydride Residues (a: Anhydride Ring b: Carbonate) | Elemental Analysis Values (wt %) | | | | | | Introduction Rate into SMA (%) |
|---|---|---|---|---|---|---|---|---|---|---|---|---|
| | | | | | | N | C | S | H | C/N | S/N | |
| Amidated SMA Derivatives | Aqueous Solution System | — | 12 | 167 | a | 7.1 | 60.3 | — | 6.7 | 8.5 | — | (partially containing ammonium salts) |
| | | | | | | 5.9 | 67.5 | — | 6.3 | 11.4 | — | 100 |
| | Organic Solvent System (DMF) | — | 18 | 1 | a | 2.6 | 56.9 | — | 6.1 | 25.6 | — | |
| | | | | | | 2.6 | 70.4 | — | 5.8 | 27.0 | — | 43 |
| | | — | 19 | 5 | a | 5.2 | 63.1 | — | 6.6 | 12.1 | — | |
| | | | | | | 5.2 | 68.1 | — | 6.2 | 13.0 | — | 87 |
| | | — | 20 | 10 | a | 5.5 | 62.7 | — | 6.7 | 11.3 | — | |
| | | | | | | 5.5 | 67.8 | — | 6.2 | 12.2 | — | 93 |
| | | — | 17 | 50 | a | 5.4 | 63.9 | — | 6.6 | 11.8 | — | |
| | | | | | | 5.4 | 68.0 | — | 6.2 | 12.6 | — | 90 |
| Tris-SMA Derivatives | Organic Solvent System (DMF) | — | 32 | 1/2 | a | 2.4 | 60.9 | — | 6.5 | 25.1 | — | |
| | | | | | | 2.4 | 65.8 | — | 6.2 | 27.1 | — | 48 |
| | | — | 33 | 1 | a | 3.5 | 57.3 | — | 6.8 | 16.5 | — | |
| | | | | | | 3.5 | 62.8 | — | 6.5 | 18.1 | — | 78 |
| | | — | 31 | 5 | a | 3.9 | 56.3 | — | 7.0 | 14.3 | — | |
| | | | | | | 3.9 | 61.5 | — | 6.7 | 15.6 | — | 94 |
| | | — | 34 | 5 | b | 3.8 | 55.4 | — | 6.9 | 14.6 | — | |
| | | | | | | 3.8 | 63.3 | — | 4.1 | 16.7 | — | 86 |
| Mercapto SMA Derivatives [ethanethiol] [L-Cysteine] | Organic Solvent System (DMF) | — | 21, 22 | 5 | a | 6.8 | 54.3 | 15.5 | 6.7 | 8.0 | 2.3 | (S-S bond) |
| | | | | | | 4.7 | 61.9 | 10.8 | 6.4 | 13.1 | 2.3 | 100 |
| | | TEA | 23 | 5 | a | 6.8 | 54.0 | 15.6 | 6.6 | 8.0 | 2.3 | (S-S bond) |
| | | | | | | 4.7 | 61.9 | 10.8 | 6.4 | 13.1 | 2.3 | 100 |
| | Organic Solvent system (DMF) | — | 24 | 5 | a | 0.7 | 63.8 | 1.6 | 5.8 | 93.8 | 2.3 | |
| | | | | | | 0.7 | 70.2 | 1.6 | 5.4 | 101.7 | 2.3 | 11 |
| | | — | 25 | 5 | b | 2.9 | 42.8 | 6.0 | 5.2 | 14.7 | 2.1 | |
| | | | | | | 2.9 | 52.1 | 6.7 | 4.3 | 17.9 | 2.3 | 74 |
| | | | | | | 2.6 | 52.5 | 6.0 | 4.3 | 20.0 | 2.3 | 66 |
| | | TEA | 26 | 5 | a | 3.8 | 57.2 | 7.7 | 5.9 | 15.1 | 2.0 | |
| | | | | | | 3.8 | 58.6 | 8.7 | 5.5 | 15.5 | 2.3 | 88 |
| | Organic Solvent System (DMAc) | — | 27 | 5 | a | 1.3 | 62.7 | 2.8 | 5.8 | 47.2 | 2.1 | |
| | | | | | | 1.3 | 67.8 | 3.1 | 5.4 | 51.0 | 2.3 | 24 |
| | | | | | | 1.2 | 68.2 | 2.8 | 5.4 | 55.9 | 2.3 | 21 |
| | | — | 28 | 5 | b | 3.0 | 44.2 | 5.9 | 5.3 | 14.8 | 2.0 | |
| | | | | | | 3.0 | 51.9 | 6.8 | 4.4 | 17.4 | 2.3 | 77 |
| | | | | | | 2.6 | 52.6 | 5.9 | 4.3 | 20.2 | 2.3 | 64 |
| | | TEA | 29 | 5 | a | 3.6 | 56.9 | 7.6 | 5.6 | 15.9 | 2.1 | |
| | | | | | | 3.6 | 59.5 | 8.2 | 5.5 | 16.7 | 2.3 | 81 |
| | | | | | | 3.3 | 60.4 | 7.6 | 5.5 | 18.1 | 2.3 | 73 |

The result of the elementary analysis shown in Table 1 was obtained with the use of Model Vario MICRO Cube provided by Elementar Analytical (Hanau city, Germany) according to the manual provided by the manufacturer.

(Example 12) Synthesis of SMA-Hydrazone-Pirarubicin Conjugate

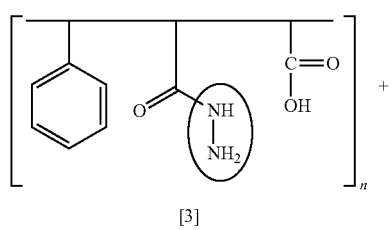

[3]

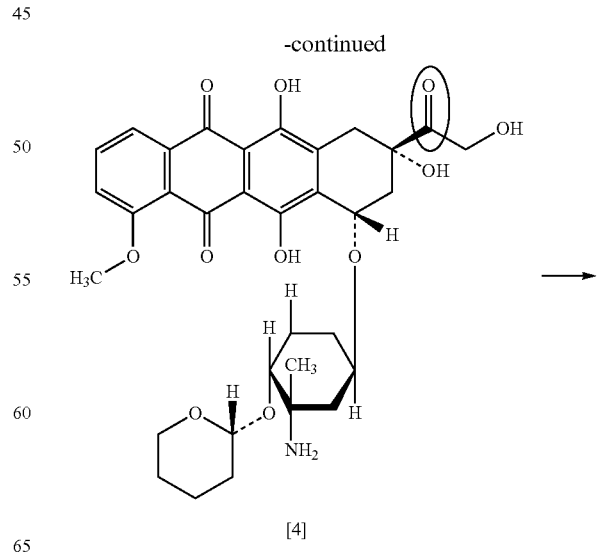

[4]

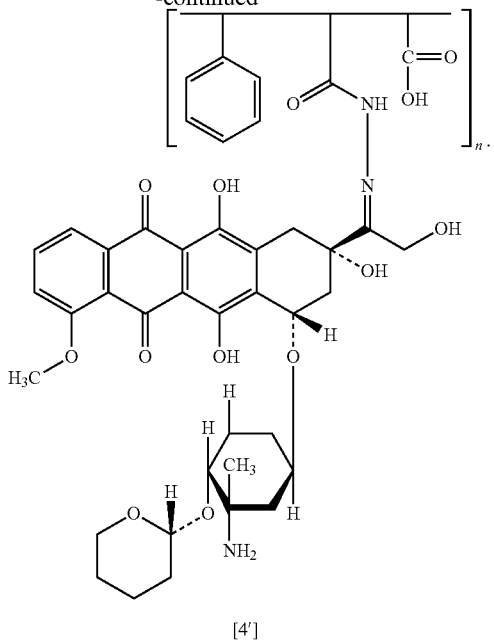

[4']

The hydrazinated SMA (500 mg) prepared in Example 1 was respectively dissolved in 50 ml of methanol or dimethylformamide (DMF) in a 150 ml beaker, and to the solution was added 100 mg of pirarubicin (tetrahydropyranyldoxorubicin from Mercian Corporation, Tokyo; hereinafter, referred to as "THP") [4] was added and reacted under stirring with a magnetic stirrer at 37° C. in the dark overnight.

Methanol in the reaction was removed in a rotary evaporator under reduced pressure to obtain orange powders. The product was dissolved in 50 ml of distilled water under stirring at room temperature with intermittent ultrasonic treatment. The solution was applied to column chromatography according to the conventional procedure as required, for example, with Sephadex G-50 or G-70 to observe the peaks of the conjugate. Alternatively, the aqueous solution was dialyzed and concentrated to remove unreacted small molecules and degradates with Lab. Scale from Amicon in a similar manner to Example 1 and then lyophilized to obtain powders of a SMA-hydrazone-THP [formula 4'] (yield: about 85% relative to THP).

Test Example 1

The antitumor effect of the SMA-hydrazone-THP conjugate (hereinafter referred to as "SMA-THP") synthesized in Example 12 was investigated in a mouse colon cancer (C26) model. The $LD_{50}$ was 150 mg/kg or more, which indicates that the toxicity was reduced to 1/10 or less compared to the $LD_{50}$ of free THP (14.4 mg/kg). Further, the size of 5180 tumor in mice was significantly suppressed by two administrations of SMA-THP respectively at a dose of 10 mg and 30 mg/kg.

The single administration at a dose of 30 mg/kg also completely inhibited the lung metastasis of the colon cancer C26 inoculated in the back and 100% of the animals survived (Table 2). Administration at doses and 10 mg and 0 mg showed the reduction of the effects in proportion to doses (Table 2).

SMA-THP and pirarubicin (THP) were administered intravenously to mice at the respective dose shown in Table 2 at Day 10 from the inoculation of cancer in mice, and the antitumor effect was evaluated at Day 50. Subsequently, $5 \times 10^5$ colon cancer (C26) cells were inoculated in the back in Balb mice and the model animals with tumor size of 5 to 6 mm at about Day 7 to 9 were treated. Single administration of 30 mg/kg of SMA-THP inhibited completely the lung metastatic cancer (referred to as daughter nodes), which is in general easily detectable 40 to 60 days after the tumor inoculation (Table 2). The maximum tolerated dose of SMA-THP was 120 mg/kg, and the dose of 30 mg/kg did not show any adverse toxicity. On the contrary, free THP was almost ineffective on the metastatic cancers at the maximum tolerated dose of 3 mg/kg (Table 2). Further, conventional carcinostatic agents are unknown for such potent antimetastatic effects.

TABLE 2

Antitumor effects on the lung cancerous nodes metastasized from colon cancer (C26)

| | | Number of Metastatic Cancerous Nodes/Mouse* | | |
|---|---|---|---|---|
| Drug | Dose (mg/kg) | No Metastasis (−) | (1~5) (+) | (>6)† (++) |
| Control (no drug) | 0 | 0/5 | 1/5 | 4/5 |
| SMA-THP | 10 | 2/5 | 2/5 | 1/5 |
| | 30 | 5/5 | 0/5 | 0/5 |
| THP | 3# | 0/5 | 2/5 | 3/5 |

*The denominator is the number of the mice in a group; the numerator is the number of the mice showing metastasis.
†Grouping of mice based on the number of tumoric nodes in a mouse.
MTD amount.

Test Example 2

Cytotoxicity of the SMA-THP synthesized in Example 12 was tested in mouse colon cancer cell line, C26 cells. The viability of the cancer cells was evaluated with MTT assay according to the conventional procedure. The cells were treated with SMA-THP in media for 48 to 72 hours at 37° C. The toxicity of SMA-THP was reduced to about 1/20 at pH 7.4, which is a phenomenon observed generally in macromolecular-conjugated drugs. When the cells were treated with the drug at a lower pH of 6.9, 6.5, 6.0 and 5.5, the toxicity was increased. At pH of 6.5 or less similar to that of tumor tissues, the drug exhibited toxicity comparative to free THP. It indicates that under the condition, the hydrazone bond is cleaved to generate free THP, which is efficiently transported into cells by a transporter and thereby exhibits medicinal effects. Further, the toxicity of the drug is reduced to about 1/20 at pH of the normal tissue, which makes the drug more advantageous.

Table 3 shows that the cytotoxicity of SMA-THP was reduced to 1/20 relative to free THP under neutral pH of normal tissue, while the cytotoxicity was significantly increased at acidic pH conditions (for example, pH 6.5).

TABLE 3

Evaluation of cytotoxicity of SMA-THP to mouse colon cancer cells (C26) in vitro

| Test Drug/Treatment Condition | Viability of Colon Cancer $C_{26}$ Cells in in vitro Culture System (% of viable cells based on the cell number of no drug as 100%) (50% Inhibition; free drug equiv.) | Viability Compared to Control |
|---|---|---|
| No Drug | $IC_{50}$ (μg/ml) | 100% |
| Free THP | 1.2 | |
| SMA-THP (hydrazone conjugates) | | |
| pH 7.4 ⎫ | 23.2 | |
| pH 6.9 ⎪ treated for 48 hours | 9.4 | 50% |
| pH 6.5 ⎬ at each pH | 2.1 | |
| pH 6.0 ⎪ | 1.8 | |
| pH 5.5 ⎭ | 1.0 | |

Viability was analyzed by MTT methods using spectroscopic methods (Maeda et al., unpublished data).

FIGS. 5 and 6 show the antitumor activities of the SMA-THP on S-180 tumors in mouse models in vivo. Intravenous injection of SMA-THP at a dose of 30 mg/kg twice provided the antiproliferative effect of tumors at Day 40 almost completely. Further, 60% of mice in the both group administered with 10 mg/kg and 30 mg/kg survived when bred over 120 days (10 animals/group). Considering that all the mice in the control group died before Day 80, SMA-THP was evidently effective (FIGS. 5 and 6).

FIG. 5. S-180 tumor cells were subcutaneously inoculated in the back of ddY mice with $5 \times 10^5$ cells. When the tumor size reached 6 to 7 mm (Day 12) and Day 16, the drug solution (comprising SMA-THP) at doses of 10 mg/kg and 30 mg/kg of body weight, and saline solution as control were respectively (0.1 ml per mouse) administered intravenously and the volume (V) of the inoculated tumor in the back was measured every 2 days. The tumor volume V was calculated by (the length of large axis of the tumor)×(the length of short axis)×(the length of short axis)/2.

FIG. 6 shows the survival rate of the mice in each group mentioned in FIG. 5. Administration of SMA-THP at doses of 10 mg and 30 mg both greatly improved the survival rate for a long period compared to no drugs.

(Example 13) Synthesis of SMA-Hydrazone-Levulinyl Zinc Protoporphyrin Conjugate

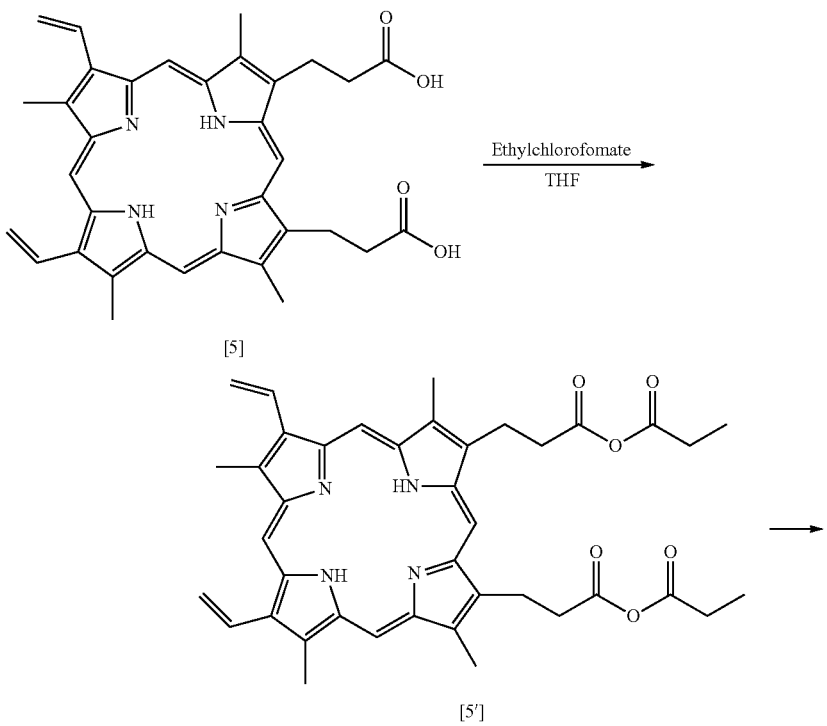

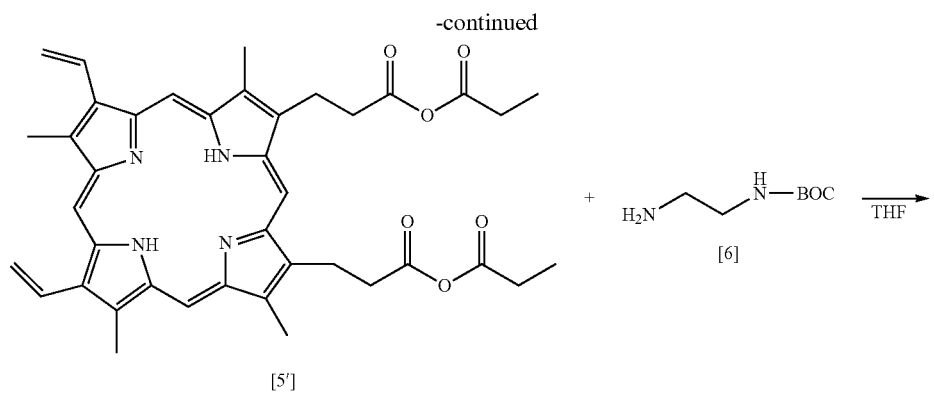
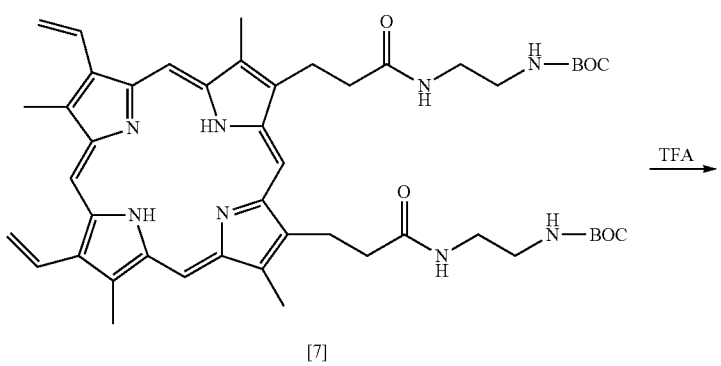
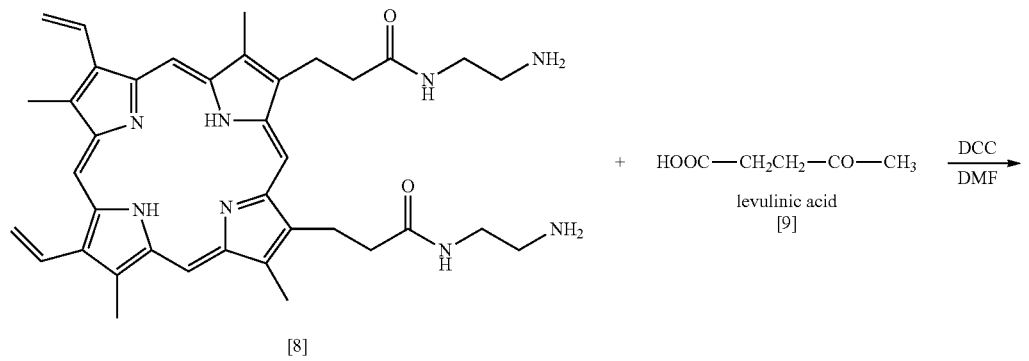
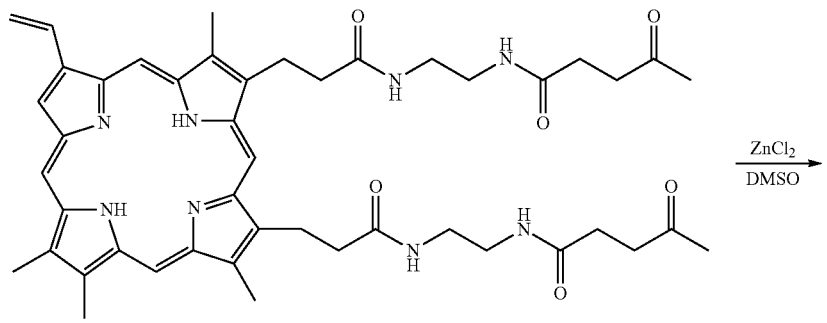

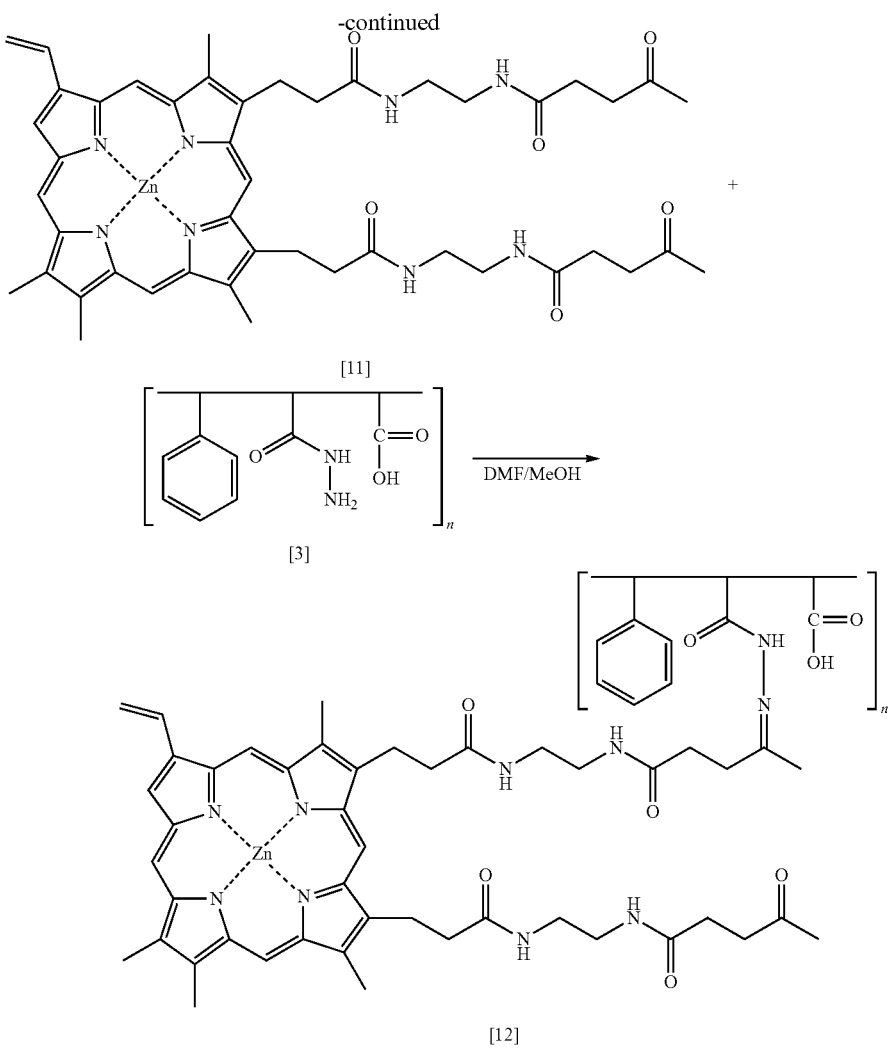

(Example 13-1) Synthesis of PP-ED-BOC (t-Butoxycarbonyl): Aminoethylation of PP by Ethylenediamine PP (protoporphyrin IX) (Sigma Aldrich, St. Louis, Mo., USA) [5] 100 mg was weighted in a 100 ml beaker and dissolved in 20 ml of tetrahydrofuran. Triethylamine 0.25 ml (Wako Pure Chemical Industries) and ethyl chloroformate 0.34 ml (Tokyo Chemical Industry Co., Ltd, Tokyo) were further added under stirring on ice and reacted for 10 minutes. Tetrahydrofuran and ethyl chloroformate were removed under reduced pressure in a rotary evaporator at 20 to 50° C. Subsequently, 20 ml of tetrahydrofuran was added to redissolve the active esters of PP (formyl esters of PP). BOC-ethylene diamine hydrochloride (ED-BOC, BOC-amino ethylamine, 105 mg; manufactured by Tokyo Chemical Industry Co., Ltd) was added and reacted for 1 to 2 hours at room temperature to obtain PPED-BOC. As described above, tetrahydrofuran was removed in a rotary evaporator and then 50 ml of ice-cooled distilled water was added. After suspending and washing, the product was centrifuged to obtain PPED-BOC as precipitates.

(Example 13-2) Synthesis of PPED from PPED-BOC: Elimination of Boc (t-Butoxycarbonyl) Group In a 50 ml beaker, 5 ml of trifluoroacetic acid (Wako Pure Chemical Industries) was placed and PPED-BOC (t-butoxycarbonyl) [6] (100 mg) was added under stirring at room temperature. The mixture was reacted for 10 to 60 minutes to eliminate the Boc group. Trifluoroacetic acid was removed in a rotary evaporator to obtain PPED (accurately, PP-bis (aminoethylamine) [8]).

(Example 13-3) Synthesis of PPED-LA

In a similar manner to the reaction in Example 13-1, the amino group in the PPED (100 mg) was condensed with the carboxyl group in the levulinic acid [9] (50 mg; Tokyo Chemical Industry Co., Ltd) in 10 ml of dimethylformamide. In detail, the reaction was in a similar manner to the preparation of PPED BOC from PP (see Example 13-1). DCC or EDAC (94 mg), and then levulinic acid (50 mg; Tokyo Chemical Industry Co., Ltd, Tokyo) were added under stirring and reacted for 6 to 12 hours at 40° C. Distilled water (100 ml) was added to obtain the PPED-levulinic acid conjugate (levulinyl PPED) [10] as precipitates, which were dissolved in 30 ml of 0.05 M NaOH. To the solution was added 300 ml of distilled water. The obtained solution was dialyzed against distilled water with an ultrafiltration device from Amicon with a molecular sieve membrane with a molecular weight cut-off of 5000 or 8000 and concentrated to ⅕ volume (×3), and then lyophilized.

(Example 13-4) Synthesis of Zn (Zinc) PPED-LA [11]: Chelation of PP with Zinc

Levulinyl PPED (100 mg) [10] was dissolved in 10 ml of DMSO. Zinc chloride (1 g; Wako Pure Chemical) was added to the solution under stirring at 60° C. for chelating PPED with zinc for 3 to 6 hours to obtain levulinyl ZnPPED [11]. Ice-cooled distilled water (500 ml) was added to obtain ZnPPED as precipitates. ZnPPED was washed with 50 ml of ice-cooled distilled water three times to remove excessive zinc chloride and the product was lyophilized to obtain about 95 mg of ZnPPED [11]. The chelation of PP with zinc was confirmed by measuring the UV-VIS spectrum (λmax changed from 406 nm to 422 nm).

(Example 13-5) Conjugation of Levulinyl Zn Protoporphyrin and Hydrazinated SMA

This reaction was performed in a similar manner to the synthesis of SMA-hydrazone-THP in Example 6. Reaction for conjugating hydrazide in SMA chain and carbonyl group in levulinyl PP was performed in methanol for 1 to 10 hours, preferably 5 hours at room temperature in a similar manner to the formation of Schiff base. To this reaction product was added 100 to 200 ml of distilled water under stirring and then this mixture was concentrated to ¹/₁₀ volume and dialyzed repeatedly with dialysis/concentration device, Lab. Scale from Amicon. In detail, the addition of 100 to 200 ml of distilled water, concentration and dialysis were repeated 3 to 4 times to obtain a concentrated solution. This concentrated solution (50 ml) was applied to gel filtration with Biogel P10 or Sephadex G-100 column (φ 3×80 cm) to obtain SMA-levulnil [Zn] PP. The fraction with absorption at 450 nm was collected and lyophilized to obtain the desired SMA-hydrazone-levulinyl [Zn] PP (yield: about 450 mg; 90% based on hydrazinated SMA; 95 mg as [Zn] PP; yield efficient: about 90%).

Example 14

A PP-aminolevulinate (PP-ALA-Et) was synthesized in accordance with the method for synthesizing PPED from PP described in Example 13-1

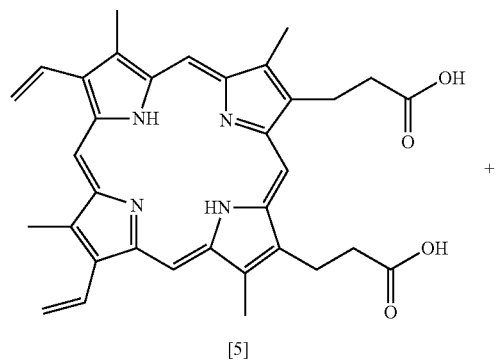

[5]

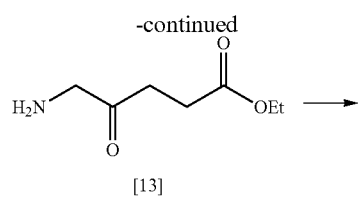

[13]

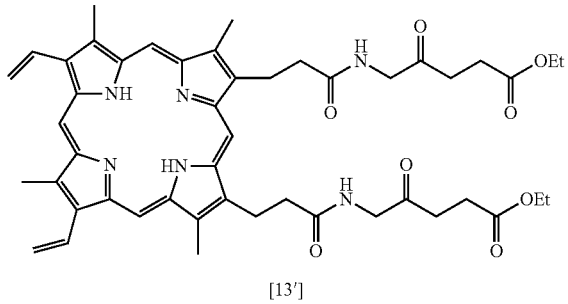

[13']

In a 150 ml beaker, PP [5] (100 mg) was placed and dissolved in 20 ml of tetrahydrofuran. In a similar manner to the condensation reaction in the synthesis of PPED-BOC in Example 13-1, 0.25 ml of triethylamine and 0.34 ml of ethyl chloroformate were added to the solution on ice under stirring and the mixture was reacted for 10 minutes. Tetrahydrofuran and ethyl chloroformate were removed at 20 to 50° C. under reduced pressure in a rotary evaporator. To the reaction product was added 20 ml of tetrahydrofuran to redissolve the active esters of PP. Aminolevulinic acid ethyl ester (ALA-Et) [13] (70 mg) was added and the mixture was reacted for 30 to 60 minutes to obtain PP-ALA-Et. Tetrahydrofuran was removed in a rotary evaporator. After adding 50 ml of distilled water, the reaction liquid was suspended washed, and then centrifuged to obtain PP-ALA-Et as precipitates.

The reaction was confirmed by high performance liquid chromatography (HPLC; column: GF-310HQ Shodex; separating solvent: DMSO/MeOH=30/70 further added with trifluoroacetic acid at a concentration of 10 μl/L; Elution time: about 12 minutes).

(Example 15) Reaction for Conjugating Protoporphyrin (PP) Levulinate and Hydrazinated SMA The reaction for conjugating above protoporphyrin (PP) levulinate with hydrazinated SMA was particularly performed as follows.

The above ingredients were both dissolved in DMF or methanol and reacted at room temperature for 1 to 12 hours, preferably for 3 to 5 hours under stirring with a magnetic stirrer. A hydrazinated SMA compound (300 mg) was mixed with 650 mg of PP-levulinate (1 mmol). The types of PP-levulinate cross-linked may vary depending on the introduction rate of hydrazine into SMA and the length of the SMA chain. After the reaction, the solvent was removed in a rotary evaporator. The product was then dialyzed against neutral to weak alkaline water and lyophilized to obtain SMA-hydrazone-levulinate [Zn]-PP (yield: about 580 mg; 85% based on the hydrazinated SMA; about 560 mg as [Zn] PP; yield efficiency: about 80%).

(Example 16) Synthesis of Amidated SMA in Aqueous Solution

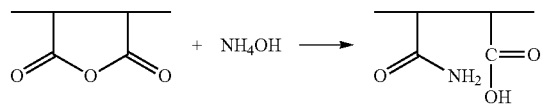

To 20 ml of distilled water placed in a 50 ml beaker, SMA-maleic anhydride copolymer powders (100 mg, 0.5 mmole as maleic anhydride residues; average molecular weight 1000-1500) were added. To the suspension stirred with a magnetic stirrer at 50 to 60° C., concentrated aqueous ammonia (25%; about 5 ml) was added to perform ammonolysis for 5 hours to 5 days. In general, the reaction is performed at 56° C. for about 40 hours to open the rings of maleic anhydride residues completely. For maintaining 1 to 4 maleic anhydride residues, the reaction is performed for 5 to 10 hours. In this case, the reaction is performed at about room temperature when required and the amount of ammonia is appropriately reduced, for example, to 80% mole equivalent.

The reaction liquid was then cooled at room temperature. 0.5M HCl was slowly added dropwise under stirring. The reaction liquid became cloudy when the pH decreased to 5 to 3. When white precipitates were formed, the reaction solution was left for about 6 hours at 4 to 6° C. to settle white precipitates of amidated SMA. The precipitates were filtered through a glass filter and then washed with 30 ml of 0.01 M ice-cooled HCl three times. To the obtained product, 20 ml of distilled water was added several times to collect the precipitates in a 100 ml beaker. Then pH was adjusted to about 8 with 50 ml of 5% sodium bicarbonate. The precipitates were then dissolved under stirring and the solution was dialyzed against distilled water and lyophilized (yield: 95 mg).

(Example 17) Synthesis of Amidated SMA in Organic Solvent System

In a 200 ml beaker, 300 mg of the above SMA maleic anhydride copolymer powders (1.5 mmole equivalents as maleic anhydride, from Sartomer) was placed and 15 ml of dimethylformamide (DMF) was added to dissolve the powders. Then, 4.46 ml of 25% aqueous ammonia (concentrated ammonia; 65.5 mmol as $NH_3$) was added and the mixture was stirred with a magnetic stirrer for 24 hours at room temperature to perform ammmonolysis (amidation). Ammonia was evaporated in a rotary evaporator. Distilled water (100 mg) was added to redissolve the obtained product and the solution was concentrated to ¼ volume with an ultra-filtration device (Amicon, Lab. Scale). Then 5 times amount of water was added and the solution was again concentrated to ¼ volume. The steps were repeated further two to three times and then the obtained aqueous solution was lyophilized to obtain amidated SMA (yield: 316 mg).

In both Examples 16 and 17, amidated SMA-maleic acid was obtained quantitatively. Table 1 shows the result of elemental analyses of the products.

Example 18

In the organic solvent system of Example 17, amidated-SMA was prepared under similar conditions except that ammonia was added in an amount of 1 mol/l equivalent of the anhydride ring. The amount of the amide N in the obtained amidated SMA was about half of that in amidated SMA obtained in Example 17. Namely, about 50% of maleic anhydride residues remained intact (indicated by an IR peak value of 1850 $cm^{-1}$).

Examples 19 to 20

In the organic solvent of Example 17, amidated-SMA was prepared under similar reaction conditions except that the ammonia was added in an amount of 5 mol/l equivalent of the anhydride ring (Example 19) or 10 mol/l equivalent of anhydride ring (Example 20). In the amidated SMA obtained in these Examples, 90% or more maleic anhydride rings were amidated (Table 1).

(Example 21) Synthesis of Thiolated SMA Derivative

In a 300 ml beaker, 200 mg of SMA maleic anhydride copolymer (about 1 mmole equivalent as maleic anhydride) was placed and 0.1 M $NaHCO_3$/0.1 M $Na_2CO_2$ buffer or tris HCl buffer with pH 8.0 to 9.5, preferably pH 8.5 (50 ml) was added and stirred with a magnetic stirrer. To the reaction mixture was added 200 mg of 2-aminoethanethiol ($H_2N$—$CH_2CH_2$—SH) powders (about 1 mmole equivalent) to react maleic anhydride residues in SMA with amino group. This reaction was continued at room temperature for 3 to 50 hours, preferably 8 hours. Then 200 ml of distilled water was added and the product was dialyzed through a molecular sieve membrane with a molecular weight cut-off at 1000 Da with Amicon, Lab. Scale and dialyzed and concentrated to ⅕ volume. Distilled water (200 ml) was further added and the same steps were repeated 4 times. The product was lyophilized to obtain the reaction product (yield: 220 mg). The introduction rate of mercaptan (SH) was about 1 residue of ethyl mercaptan per 6 maleic anhydride residues when calculated based on the sulfur content in the mercapto SMA.

(Example 22) Reaction of Maleic Anhydride Residues with 5 Mole Excess Equivalents of 2-Amino-Ethanthiol in DMF [Anhydride Ring:2-Aminoethanethiol=1:5 (Mole Ratio)]

To 300 mg of SMA-maleic acid copolymer powders (1.3 mmole equivalents as maleic anhydride) was added 15 ml of dimethylformamide (DMF) to dissolve the powders. Then 505.3 mg (6.6 mmol) of 2-aminoethanethiol (Wako Pure Chemical Industries, Osaka) was added and stirred for 24 hours at room temperature with a magnetic stirrer. After the reaction for 24 hours, the clouded liquid was filtered under reduced pressure (glass filter No. 5C) and concentrated in a rotary evaporator. Precipitates were generated by diluting with distilled water. The crude product was dialyzed through a dialysis membrane with a molecular weight cut-off at 1000 Da [manufactured by Spectrum Laboratories] 2 to 3 times. The filtrates and the precipitates were separated by decantation, and then the suspensions were lyophilized to obtain white powders (about 221.9 mg). The yield was about 70.3% based on the original SMA conjugate. Table 1 shows the result of elemental analyses.

(Example 23) Reaction of with Maleic Anhydride Residues with 5 Mole Excess Equivalents of 2-Aminoethanthiol in the Presence of a Catalyst in DMF [Anhydride Ring:2-Aminoethanethiol=1:5 (Mole Ratio)]

To 300 mg of SMA-maleic acid copolymer powders (1.3 mmole equivalents as maleic anhydride) was added 15 ml of dimethylformamide (DMF) to dissolve the powders. Then 505.3 mg (6.6 mmol) of 2-aminoethanethiol (Wako Pure Chemical Industries, Osaka) was added. After stirring for 2 to 3 minutes with a magnetic stirrer, 500 µl of triethylamine (Wako Pure Chemical Industries, Oosaka) was added and stirred for another 24 hours at room temperature with a magnetic stirrer. After the reaction for 24 hours, the clouded liquid was filtered under reduced pressure (glass filter No. 5C) and concentrated in a rotary evaporator. Precipitates were generated by diluting with distilled water. The crude product was dialyzed with a dialysis membrane with a MW cut-off at 1000 Da [Spectrum Laboratories] 2 to 3 times. The filtrates and the precipitates were separated by decantation, and then the precipitates were lyophilized to obtain white powders (about 248.1 mg). The yield was about 80% based on the original SMA conjugate. Table 1 shows the result of elemental analyses.

(Example 24) Reaction of with Maleic Anhydride Residues with 5 Mole Equivalents of L-Cysteine in DMF [Anhydride Ring:L-Cysteine=1:5 (Mole Ratio)]

To 300 mg of SMA-maleic acid copolymer powders (1.3 mmole equivalents as maleic anhydride) was added 15 ml of dimethylformamide (DMF) to dissolve the powders. Then 793.6 mg (6.6 mmol) of L-cysteine (Sigma Aldrich) was added and stirred for 19 hours at room temperature with a magnetic stirrer. After the reaction for 19 hours, the clouded liquid was filtered under reduced pressure (glass filter No. 5C) and concentrated in a rotary evaporator. Precipitates were generated by diluting with distilled water. The crude product was dialyzed with a dialysis membrane with a molecular weight cut-off at 1000 Da [manufactured by Spectrum Laboratories] 2 to 3 times and lyophilized to obtain white powders. The yield was about 85% based on the amount of SMA used. Table 1 shows the result of elemental analyses.

(Example 25) Reaction of Maleic Anhydride Residues with 5 Mole Excess Equivalents of L-Cysteine in DMF [Anhydride Ring:L-Cysteine=1:5 (Mole Ratio)]

To 300 mg of SMA-maleic anhydride copolymer powders (1.3 mmole equivalents as maleic anhydride) was added 15 ml of dimethylformamide (DMF) to dissolve the powders. Then 793.6 mg (6.6 mmol) of L-cysteine (Sigma Aldrich) was added and stirred with a magnetic stirrer for 19 hours at room temperature. After reaction for 19 hours, the clouded solution was concentrated in a rotary evaporator. Then the reaction liquid was stirred for 4 days at room temperature to open the ring of maleic anhydride and pH was maintained to be stabilized with a pH indicator meter by adding aqueous NaOH. The obtained colorless clear solution was dialyzed with a dialysis membrane with a molecular weight cut-off at 1000 Da [manufactured by Spectrum Laboratories] 2 to 3 times and lyophilized to obtain white powders (about 245.3 mg). Table 1 shows the result of elemental analyses.

(Example 26) Reaction of Maleic Anhydride Residues with 5 Mole Excess Equivalents of L-Cysteine in DMF in the Presence of a Catalyst [Anhydride Ring:L-Cysteine=1:5 (Mole Ratio)]

To 300 mg of SMA-maleic anhydride copolymer powders (1.3 mmole equivalents as maleic anhydride) was added 15 ml of dimethyleformamide (DMF) to dissolve the powders. Then 793.6 mg (6.6 mmol) of L-cysteine (Sigma Aldrich) was added. The reaction mixture was stirred with a magnetic stirrer for 2 hours at room temperature, and then 500 µl of trimethylamine (Wako Pure Chemical Industries, Oosaka) was added and stirred with a magnetic stirrer for 17 hours at room temperature. After the reaction for 17 hours, the reaction liquid was filtered under reduced pressure (glass filter No. 5C) and concentrated in a rotary evaporator. Precipitates were generated by diluting with distilled water. The crude product was dialyzed through a dialysis membrane with molecular cut off at 1000 Da [Manufactured by Spectrum Laboratories] 2 to 3 times and then lyophilized to obtain white powders (about 360.5 mg). Table 1 shows the result of elemental analyses.

(Example 27) Reaction of Maleic Anhydride Residues with 5 Mole Equivalents of L-Cysteine at 50° C. in Dimethylacetamide (DMAC) [Anhydride Ring:L-Cysteine=1:5 (Mole Ratio)]

To 300 mg of SMA-maleic anhydride copolymer powders (1.3 mmole equivalents as maleic anhydride) was added 15 ml of dimethylacetamide (DMAC) to dissolve the powders. Then 793.6 mg (6.6 mmol) of L-cysteine (Sigma Aldrich) was added and the mixture was stirred for 19 hours at 50° C. with a magnetic stirrer. After the reaction for 19 hours, the clouded liquid was filtered under reduced pressure (glass filter No. 5C) and concentrated in a rotary evaporator. Precipitates were generated by diluting with distilled water. The crude product was dialyzed through a dialysis membrane with a molecular weight cut off at 1000 Da [manufactured by Spectrum Laboratories] 2 to 3 times and lyophilized to obtain white powders (about 320.7 mg). Table 1 shows the result of elemental analyses.

(Example 28) Reaction of Maleic Anhydride Residues with 5 Mole Excess Equivalents of L-Cysteine at 50° C. in DMAC [Anhydride Ring:L-Cysteine=1:5 (Mole Ratio)]

To 300 mg of SMA-maleic anhydride copolymer powders (1.3 mmole equivalents as maleic anhydride) was added 15 ml of dimethylacetamide (DMAC) to dissolve the powders. Then 793.6 mg (6.6 mmol) of L-cysteine (Sigma Aldrich) was added and the mixture was stirred for 19 hours at 50° C. with a magnetic stirrer. After the reaction of 19 hours, the clouded liquid was concentrated in a rotary evaporator. The liquid was stirred for days at room temperature to open the rings of maleic anhydride and pH was maintained with a pH meter by adding aqueous NaOH. The obtained colorless clear solution was dialyzed with a dialysis membrane with a molecular weight cut-off at 1000 Da [Manufactured by Spectrum Laboratories] 2 to 3 times and lyophilized to obtain white powders (about 286.5 mg). Table 1 shows the result of elemental analyses.

(Example 29) Reaction of the Maleic Anhydride Residues with 5 Mole Excess Equivalents of L-Cysteine in the Presence of Catalyst at 50° C. in DMAC [Anhydride Ring:L-Cysteine=1:5 (Mole Ratio)]

To 300 mg of SMA-maleic anhydride copolymer powders (1.3 mmole equivalents as maleic anhydride) was added 15 ml of dimethylacetamide (DMAC) to dissolve the powders. Then 793.6 mg (6.6 mmol) of L-cysteine (Sigma Aldrich)

was added. The reaction mixture was stirred for 2 hours at 50° C. with a magnetic stirrer and then 500 μl of trimethylamine (Wako Pure Chemical Industries, Osaka) was added and stirred for 17 hours at 50° C. with a magnetic stirrer. After the reaction for 17 hours, the reaction liquid was filtered under reduced pressure (glass filter No. 5C) and concentrated in a rotary evaporator. Precipitates were generated by diluting with distilled water. The crude product was dialyzed through a dialysis membrane with a molecular weight cut off at 1000 Da [manufactured by Spectrum Laboratories] 2 to 3 times and lyophilized to obtain white powders (about 383.3 mg). Table 1 shows the result of elemental analyses.

(Example 30) Synthesis of SMA-S—S—X Via the S—S Exchange Reaction Between BSH (Boronomercaptate; $Na_2B_{12}H_{11}SH$; Abbreviated as BSH) and Mercapto SMA SMA-SH prepared in Example 21 or 22 is reacted with a SH compound, for example, boron hydride ($B_{12}SH$, boron mercaptate) according to the following formula:

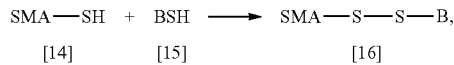

wherein B represents a boron mercaptate, a cage compound having 12 boron atoms.

In a 150 ml beaker, 100 mg of SMA-SH was placed and 50 ml of sodium bicarbonate (pH 7 to 11, preferably about 8.5) or tris buffer was added. To this reaction was added 10 to 50 mg of BSH. $CuSO_4$ was added to the system at a concentration of 0.1 to 10 mM as a catalyst for oxidizing the B—SH group for 1 to 100 hours at room temperature. The SH group was preferably oxidized to form SS in the presence of 1 to 2 mM $CuSO_4$. To the solution of the reaction mixture air is introduced under stirring in an amount of 50 to 100 ml per minute as air bubbles through a vinyl tube to promote the oxidation reaction for forming SS bond under aeration as represented by the above formula. After the completion of the reaction for 10 to 40 hours at room temperature, the product was concentrated to about 20 ml and eluted with distilled water through a Sephacryl 200 column (φ2.5×100 cm) to purify and separate the product. The absorption peaks at 260 nm were pooled and the fraction was dialyzed against distilled water and lyophilized to obtain the product SMA-S—S—B (yield: 109 mg).

(Example 31) Synthesis of SMA-Tris Derivative

To 300 mg of SMA-maleic anhydride copolymer powders (1.5 mmole equivalents as maleic anhydride) was added 15 ml of dimethylformamidz (DMF) to dissolve the powder. Then 793.5 mg (6.6 mmol) of tris(hydroxymethyl)aminomethane (Sigma Aldrich, St. Louis, Mo., USA; hereinafter, referred to as "tris") was added. The reaction mixture was stirred for 48 hours at room temperature with a magnetic stirrer. After the reaction for 48 hours, the reaction liquid was filtered and the filtrate was concentrated in a rotary evaporator. Then the reaction liquid was stirred for 24 hours at room temperature to open the ring of maleic anhydride while maintaining pH constant with a pH indicator by adding 1 mmol/l aqueous NaOH (20 ml). The reaction liquid was again concentrated in a rotary evaporator and diluted with distilled water, dialyzed with a dialysis membrane with a molecular membrane cut-off at 1000 Da and lyophilized to obtain white powders (about 369 mg). Table 1 shows the result of elemental analyses.

(Example 32-1) Reaction of Maleic Anhydride Residues with 1/2 Mole Equivalents of Tris in DMF [Anhydride Ring:Tris=1:1/2 (Mole Ratio)]

To 500 mg of SMA-maleic anhydride copolymer powders (2.2 mmole equivalents as maleic anhydride) was added 25 ml of dimethyleformamide (DMF) to dissolve the powders. Then 132.7 mg (1.1 mmol) of tris(hydroxymethyl)aminomethane (Sigma Aldrich, St. Louis, Mo., USA; hereinafter, referred to as "tris") was added. The reaction mixture was stirred for 24 hours at room temperature with a magnetic stirrer. Separately, 500 mg of SMA-maleic anhydride copolymer powders (2.2 mmole equivalents as maleic anhydride) were reacted with 132.7 mg (1.1 mmol) of tris and 132.6 mg (1.1 mmol) of tris in the same manner. After the reaction for 24 hours, 3 batches were combined and concentrated in a rotary evaporator. Precipitates were generated by diluting with distilled water. The crude product was dialyzed through a dialysis membrane with a molecular weight cut-off at 1000 Da [Manufactured by Spectrum Laboratories] 2 to 3 times and lyophilized to obtain white powders (about 1795.1 mg). Table 1 shows the result of elemental analyses.

(Example 32-2) Synthesis of SMA-Tris-Hydrazine Derivative and ZnPP Conjugate Comprising the Derivative The SMA-tris derivative synthesized in Example 32-1 maintains about half of maleic anhydride. Hydrazine may be added to the remaining maleic anhydride in a similar manner to Example 1 to introduce further hydrazone residues and thereby obtain a SMA-tris-hydrazine.

SMA-tris-hydrazine has high solubility in water and DMSO and DMF, and is reactive with ketone groups. Thus it may be used in conjugating ZnPP with SMA in a similar manner to Example 13 to obtain a SMA-tris-hydrazyl ZnPP as a product.

SMA-tris-hydrazine may enable the synthesis of conjugates comprising THP and levulinyl ZnPP. In particular, 300 mg of the SMA-tris in Example 32-1 is dissolved in 20 ml of water. To the mixture is added 2 to 20 mole equivalents (for example 0.6 ml) of hydrazine monohydrate per 1 mol of maleic anhydride residues. The mixture is then stirred for 24 hours at room temperature for hydrazination. After the completion of the reaction, the reaction liquid was concentrated at 30 to 40° C. in a rotary evaporator, and then dialyzed to obtain lyophilized samples (yield: about 290 mg; yield efficiency: 95%; the chemical structure of the product is illustrated in the following reaction scheme).

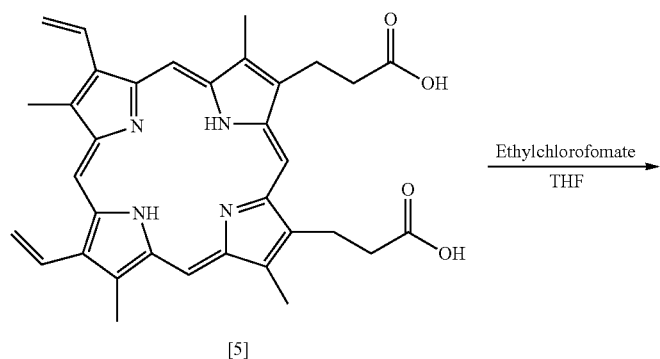
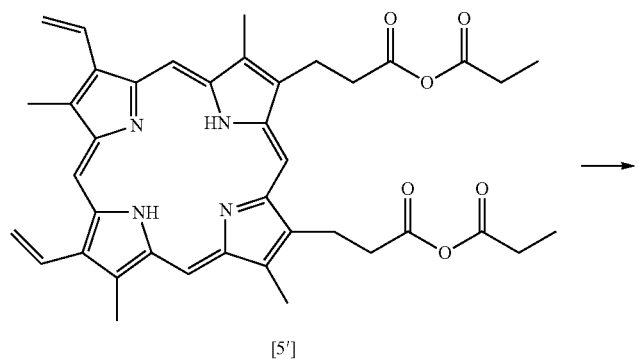
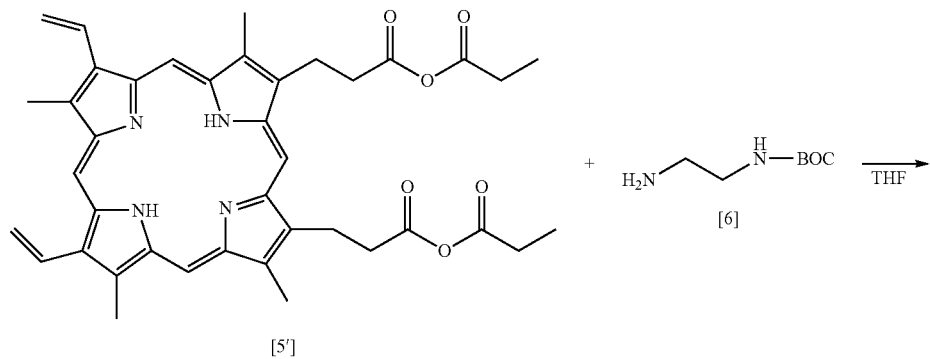
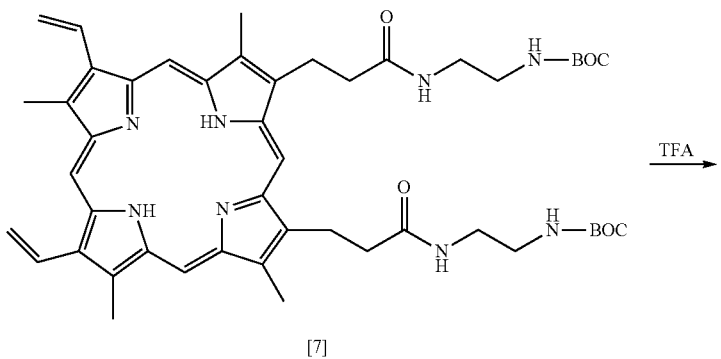

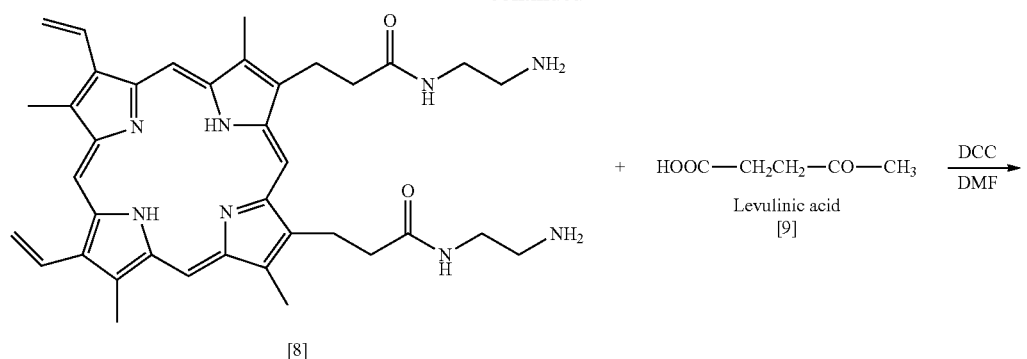
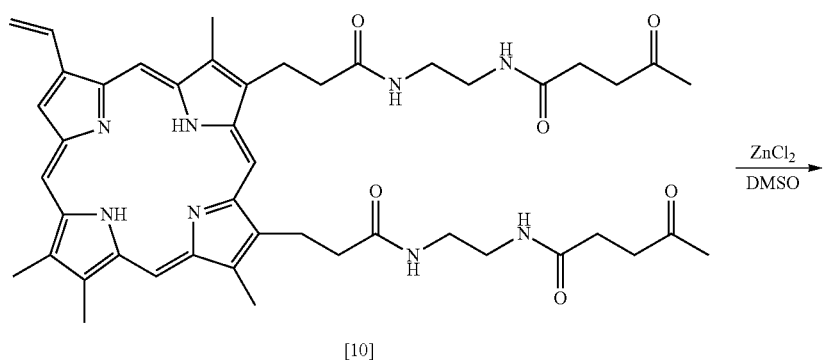
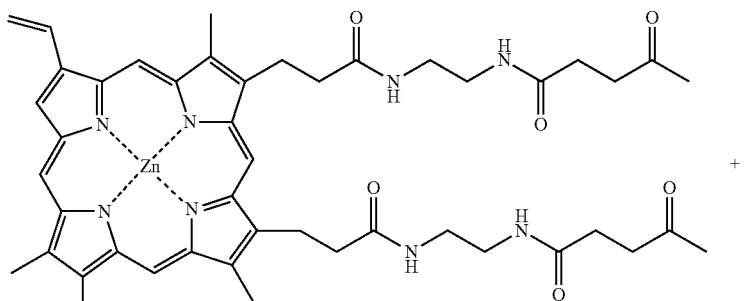
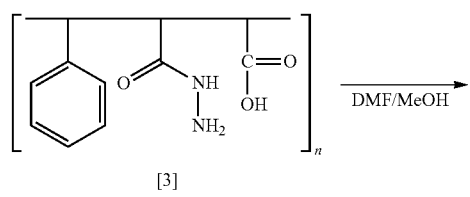

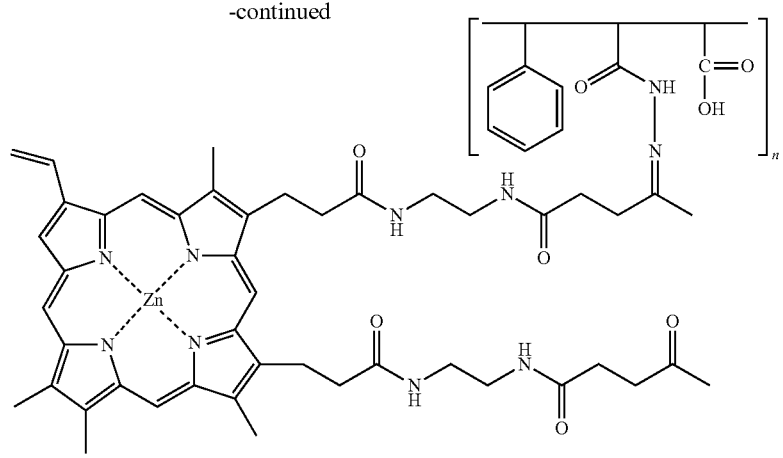

[12]

(Example 33) Reaction of Maleic Anhydride Residues with 1 Mole Equivalent of Tris in DMF [Anhydride Ring:Tris=1:1 (Mole Ratio)]

To 500 mg of SMA-maleic anhydride copolymer powders (2.2 mmole equivalents as maleic anhydride) was added 25 ml of dimethylformamide (DMF) to dissolve the powders. Then 265.3 mg (2.2 mmol) of tris(hydroxymethyl)aminomethane (Sigma Aldrich, St. Louis, Mo., USA; hereinafter, referred to as "tris") was added. The reaction mixture was stirred for 24 hours at room temperature with a magnetic stirrer. Dissolved SMA-maleic anhydride copolymer powders (500 mg, 2.2 mmole equivalents as maleic anhydride) were reacted with 265.3 mg (2.2 mmol) of tris under stirring for 24 hours and then concentrated in a rotary evaporator. The reaction liquid became slightly cloudy by addition of distilled water. The crude product was dialyzed with a dialysis membrane with a molecular membrane cut-off at 1000 Da [Manufactured by Spectrum Laboratories] 2 to 3 times and lyophilized to obtain white powders (about 639.4 mg; the product was decreased due to the loss during dialysis). Table 1 shows the result of elemental analyses.

(Example 34) Reaction of Maleic Anhydride Residues with 5 Mole Equivalents of Tris in DMF [Anhydride Ring:Tris=1:5 (Mole Ratio)]

To 304 mg of SMA-maleic anhydride copolymer powders (1.3 mmole equivalents as maleic anhydride) was added 15 ml of dimethylformamide (DMF) to dissolve the powder. Then 796.4 mg (6.6 mmol) of tris(hydroxymethyl)aminomethane (Sigma Aldrich, St. Louis, Mo., USA; hereinafter, referred to "tris") was added. The reaction mixture was stirred for 24 hours at room temperature with a magnetic stirrer. Separately, 300 mg of SMA-maleic anhydride copolymer powders (1.3 mmole equivalents as maleic anhydride) were reacted with 792.8 mg (6.6 mmol) of tris, and 299 mg of SMA-maleic anhydride copolymer powders (1.3 mmole equivalents as maleic anhydride) were reacted with 794.0 mg (6.6 mmol) of tris; and 300 mg of SMA-maleic anhydride copolymer powders (1.3 mmole equivalents as maleic anhydride) was reacted with 792.4 mg (6.6 mmol) in a similar manner. After the reaction for 24 hours, 4 batches were combined, filtered (glass filter No. 5C) and concentrated in a rotary evaporator. The reaction liquid was diluted with distilled water and dialyzed with a dialysis membrane with a molecular weight cut-off at 1000 Da [Manufactured by Spectrum Laboratories] 2 to 3 times. Then the soluble solution was lyophilized to obtain white powders (about 520.1 mg). Table 1 shows the result of elemental analyses.

Test Example 3

The releasing rate of THP (pirarubicin) from the SMA-hydrazone-THP obtained in Example 12 at various pH conditions was measured in the following manner.

The SMA-Hyd-THP was dissolved at a concentration of 1 mg/ml and the solution was incubated in a phosphate buffer comprising 0.15M NaCl at pH 5.5, 6.8 and 7.4. Then free THP released from the macromolecule was separated by high performance liquid chromatography (HPLC) and the elution from the column was quantified at 470 nm. The used HPLC device was manufactured by Shimadzu Corporation and the column was Asahipack GF310HQ (Showa Denko, Tokyo, OHpak SB-804: HQ column 300 mm×8.0 mm). The product was eluted with dimethyl sulfoxide at a rate of 0.5 ml/min. The hydrazine bond was cleaved and THP was released at about 10 fold faster rate at pH 5.5 compared to that observed at a neutral pH 7.4. FIG. 2 shows the result of this experiment.

Test Example 4

The change of the surface charge (zeta potential) of the SMA-derivatives obtained in Examples 1, 31 and other examples and the SMA-drug conjugate obtained in Example 12 was measured in the following manner.

In the measurement, a zeta potential measurement device (manufactured by Otsuka Electronics co. ltd; Phortal Model ELSZ-2) was used under the conditions described in the below table. The concentration of each sample was 3 to 10 mg/ml. Table 4 shows the result of the measurement.

TABLE 4

Change of surface charge (zeta potential) of the SMA derivatives and the SMA-drug conjugate

| Example | SMA Derivative | Character | Zeta Potential (mV)* |
|---|---|---|---|
|  | Styrene-Maleic Acid Copolymer (SMA) | drug substance | −48 to −50 |
| 1 | SMA - hydrazide derivative | hydrazine | −32 to −27 |
| 12 | SMA - hydrazone - THP | SMA - THP | −24 to −10 |

TABLE 4-continued

Change of surface charge (zeta potential) of the
SMA derivatives and the SMA-drug conjugate

| Example | SMA Derivative | Character | Zeta Potential (mV)* |
|---|---|---|---|
| 16 | SMA - amidated derivative | adduct amine | −30 to −20 |
| 21 | SMA - cysteine derivative | cysteine | −20 |
| 13-5 | SMA - hydrazone - ZnPP | ZnPP | −20 to −10 |
| 31 | SMA - tris derivative | enhanced water-solubility | −38 |

*Measured at 25° C. in 0.15M NaCl (pH 7.4).

Test Example 5

Infrared absorption spectra/KBr of the SMA derivatives obtained in Examples 1, 16, 31 and the like and the SMA-drug conjugates obtained in Examples 12 and 13-5 were measured in a following manner.

A KBr disk was obtained with FT-IR-6200, an infrared spectrograph from JASCO Corporation according to the conventional procedure. The disappearance of (maleic) anhydride rings is characterized by 1860 $cm^{-1}$ and 1780 $cm^{-1}$. FIG. 3 shows the result of this measurement.

Test Example 6

The Raman absorption spectra of the SMA derivative obtained in Example 21 and the SMA-drug conjugates obtained in Examples 26 and 28 were measured in the following manner.

Figure 4A:
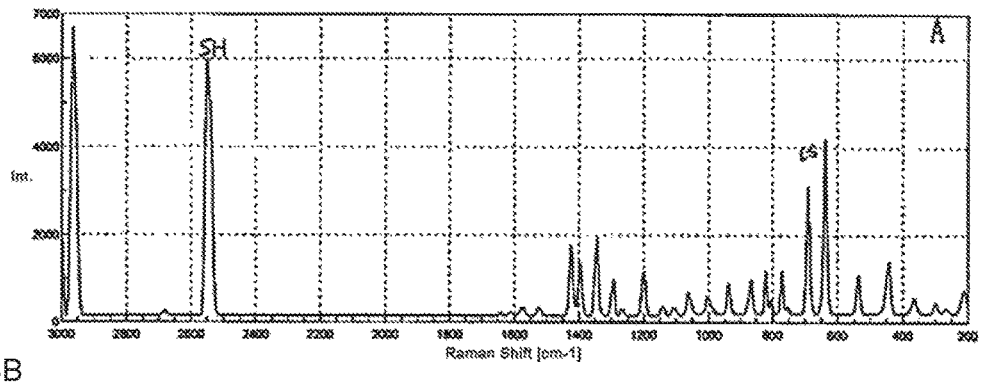
FIGS. 4A-C shows the Raman absorption spectra of the following substances.
Figure 4B:
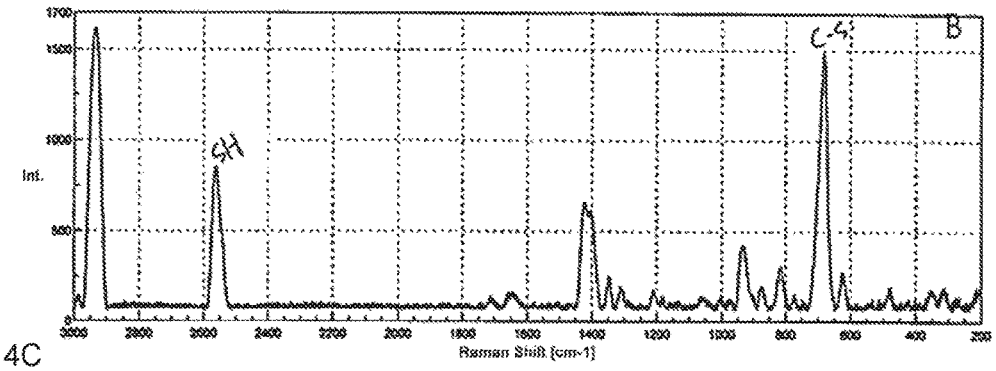
Figure 4C:
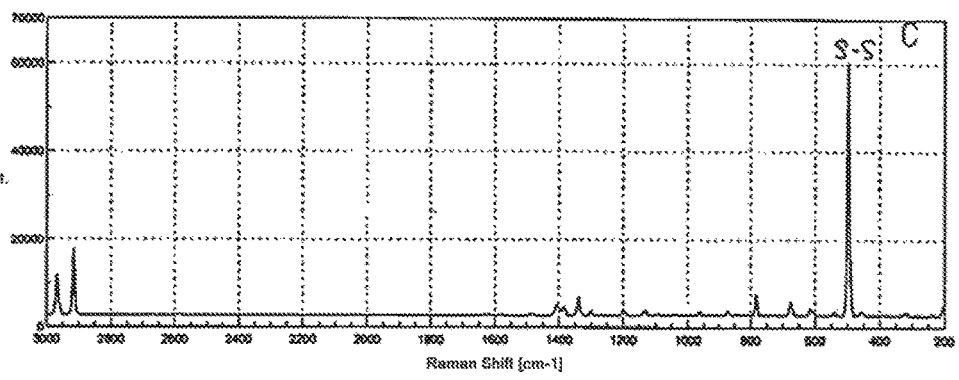

In brief, 10 to 100 mg of samples were placed on slides as powders and analyzed with NRS-5100 manufactured by JASCO Corporation. The SS group and SH group respectively show a specific peak around 500 $cm^{-1}$ and around 2590 $cm^{-1}$ respectively. FIG. 4 shows the result of this measurement.

The invention claimed is:

1. A conjugate comprising
  a. a styrene-maleic acid copolymer (SMA) derivative comprising:
    (i) a styrene-maleic acid copolymer (SMA) and
    (ii) a side chain (b) containing a functional group (a) introduced into the carboxyl group in the maleic anhydride residue in SMA and selected from —$NH_2$, —SH, —OH, —COOH, —NH—(C=NH)—$NH_2$ and —C($CH_2$—OH)$_3$ via an amide bond or an ester bond, wherein when a plurality of side chain (b) is introduced to SMA, the side chains (b) may be identical or different; and
  b. an active substance covalently bound directly or indirectly to the SMA derivative, wherein the active substance is selected from the group consisting of endorphin and enkephalin.

2. The conjugate according to claim 1 comprising the SMA derivative and an active substance covalently bound directly or indirectly to at least one functional group (a) in the side chain (b) or moiety different from the side chain (b) in the SMA derivative.

3. The conjugate according to claim 1, wherein the bond between the SMA derivative and the active substance is selected from an amide bond, an ester bond, a hydrazone bond and a disulfide bond.

4. The conjugate according to claim 1, wherein the bond between the functional group (a) in the side chain (b) in the SMA derivative and the active substance is a bond via a linking group —$R^3$—$R^4$— as represented by the following formula [B]:

Active substance-$R^3$—$R^4$—$R^{2a}$-SMA derivative [B],
  wherein $R^3$ is a group selected from —NH—, —O—, carbonyl group, alkylene group and combination thereof;
  $R^4$ is a group selected from —C($CH_3$)=N— and —C(benzyl)=N—; and
  $R^{2a}$ is —NH—,
  wherein the side chain (b) is represented by the following formula [A]:

—C(=O)—NH—$R^1$—$R^2$   [A]

wherein —$R^1$—$R^2$ in the formula [A] is —$NH_2$;
  wherein the SMA derivative includes a plurality of groups represented by the formula [A],
  wherein $R^{2a}$ is a residue derived from the hydrazide group in the formula [A].

5. The conjugate according to claim 4, wherein the linking group —$R^3$—$R^4$— in the formula [B] is a group selected from the following groups:
  (1) —NH—$(CH_2)_2$—NH—C(=O)—$(CH_2)_2$—C($CH_3$)=N—, and
  (2) —NH—$CH_2$—C(=O)—$(CH_2)_2$—C(benzyl)=N—.

6. A medicament comprising the conjugate according to claim 1.

7. The medicament according to claim 6, which is a carcinostatic agent.

8. A pharmaceutical composition comprising the conjugate according to claim 1 and a pharmaceutically acceptable carrier.

* * * * *